US010010596B2

(12) United States Patent
Galen et al.

(10) Patent No.: US 10,010,596 B2
(45) **Date of Patent: *Jul. 3, 2018**

(54) BACTERIAL LIVE VECTOR VACCINES EXPRESSING CHROMOSOMALLY-INTEGRATED FOREIGN ANTIGENS

(71) Applicants: James E. Galen, Eldersburg, MD (US); Jin-Yuan Wang, Silver Spring, MD (US)

(72) Inventors: James E. Galen, Eldersburg, MD (US); Jin-Yuan Wang, Silver Spring, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/234,703

(22) Filed: Aug. 11, 2016

(65) Prior Publication Data

US 2016/0339095 A1 Nov. 24, 2016

Related U.S. Application Data

(63) Continuation of application No. 14/687,463, filed on Apr. 15, 2015, now Pat. No. 9,446,113, which is a continuation-in-part of application No. PCT/US2013/064872, filed on Oct. 14, 2013.

(60) Provisional application No. 61/713,806, filed on Oct. 15, 2012.

(51) Int. Cl.

| | |
|---|---|
| ***A61K 39/02*** | (2006.01) |
| ***A61K 39/08*** | (2006.01) |
| ***C12N 15/74*** | (2006.01) |
| ***A61K 39/112*** | (2006.01) |
| *A61K 39/00* | (2006.01) |

(52) U.S. Cl.

CPC ...... *A61K 39/0275* (2013.01); *A61K 39/0291* (2013.01); *A61K 39/08* (2013.01); *C12N 15/74* (2013.01); *A61K 2039/522* (2013.01); *A61K 2039/523* (2013.01)

(58) Field of Classification Search

CPC ........ A61K 2039/522; A61K 2039/523; A61K 39/0275; A61K 39/0291; A61K 39/08; C12N 15/74

See application file for complete search history.

(56) References Cited

U.S. PATENT DOCUMENTS

| | | | |
|---|---|---|---|
| 9,446,113 B2 * | 9/2016 | Galen .................... | C12N 15/74 |
| 2008/0233094 A1 | 9/2008 | Vindurampulle et al. | |
| 2010/0112674 A1 | 5/2010 | Galen et al. | |

FOREIGN PATENT DOCUMENTS

| | | |
|---|---|---|
| WO | 00/32047 | 6/2000 |
| WO | 03/097838 | 11/2003 |
| WO | 2011/060431 | 5/2011 |

OTHER PUBLICATIONS

Houghten et al. Vaccines, 1986, Edited by Fred Brown: Cold Spring Harbor Laboratory.*

Galen, J. et al., A new generation of stable, nonantibiotic, low-copy-number plasmids improves immune responses to foreign antigens in *Salmonella enterica* Serovar Typhi live vectors, Infection and Immunity, 2010, vol. 78, No. 1, pp. 337-347.

Galen, J. et al., Mucosal immunization with attenuated *Salmonella* Typhi expressing anthrax PA83 primes monkeys for accelerated serum antibody responses to parenteral PA83 vaccine, J. Infect. Dis., 2009, vol. 199, No. 3, pp. 326-335.

Wang, J.Y. et al., Novel methods for expression of foreign antigens in live vector vaccines, Human Vaccines & Immunotherapeutics, 2013, vol. 9, No. 6, pp. 1-7.

Galen, J. et al., A bivalent typhoid live vector vaccine expressing both chromosome- and plasmid-encoded Yersinia pestis antigens fully protects against murine lethal pulmonary plague infection, Infection and Immunity, 2015, vol. 83, No. 1, pp. 161-172.

Wang, J.Y. et al., Novel methods for expression of foreign antigens in live vector vaccines, Human Vaccines & Immunothempeutics, 2013, vol. 9, No. 7, pp. 1558-1564.

International Search Report for PCT/US2013/064872, dated Jan. 28, 2014.

Extended European Search Report dated May 2, 2016 in corresponding European Application No. 13847433.3.

Wang et al., "Construction, Genotypic and Phenotypic Characterization, and Immunogenicity of Attenuated Δ*guaBA Salmonella enterica* Serovar Typhi Strain CVD 915", Infection and Immunity, vol. 69, No. 8, Aug. 2001, pp. 4734-4741.

* cited by examiner

*Primary Examiner* — Padmavathi Baskar

(74) *Attorney, Agent, or Firm* — Wenderoth, Lind & Ponack, L.L.P.

(57) ABSTRACT

Bacterial live vector vaccines represent a vaccine development strategy that offers exceptional flexibility. In the present invention, genes encoding protective antigens of unrelated bacterial, viral, parasitic, or fungal pathogens are expressed in an attenuated bacterial vaccine strain that delivers these foreign antigens to the immune system, thereby eliciting relevant immune responses. Rather than expressing these antigens using only low copy expression plasmids, expression of foreign proteins is accomplished using both low copy expression plasmids in conjunction with chromosomal integrations within the same live vector. This strategy compensates for the inherent disadvantage of loss of gene dosage (versus exclusive plasmid-based expression) by integrating antigen expression cassettes into multiple chromosomal sites already inactivated in an attenuated vector.

14 Claims, 7 Drawing Sheets

24 hr @ 37°C

BACTERIAL LIVE VECTOR VACCINES EXPRESSING CHROMOSOMALLY-INTEGRATED FOREIGN ANTIGENS

STATEMENT OF FEDERALLY SPONSORED RESEARCH AND DEVELOPMENT

This invention was made with government support under Grant Number AI077911 and Grant Number AI095309 awarded by the National Institutes of Health. The government has certain rights in the invention.

SEQUENCE LISTING

A sequence listing in electronic (ASCII text file) format is filed with this application and incorporated herein by reference. The name of the ASCII text file is "2016_0626_ST25.txt"; the file was created on Aug. 11, 2016; the size of the file is 92 KB.

TECHNICAL FIELD

The invention generally relates to the provision of live vector vaccines that can be used to vaccinate a subject against bacterial, viral or parasitic pathogens. In particular, the invention relates to bacterial live vector vaccines that express chromosomally-integrated antigen expression cassettes encoding selected antigens, such as protective antigens of unrelated bacterial, viral or parasitic pathogens.

BACKGROUND OF INVENTION

Excellent progress has been made over the past twenty years in the adaptation of attenuated bacterial vaccine strains for expression of foreign antigens to create multivalent live vector vaccines. This has included a devotion of significant effort to the creation of expression technologies which either directly or indirectly address the important problem of metabolic stress often associated with expression of foreign immunogens.[1,2] It is recognized that inappropriate synthesis of high levels of foreign protein in an effort to induce an antigen-specific protective immune response can adversely affect the fitness and growth rate of an already attenuated vaccine strain, resulting in over-attenuation and loss of immunity directed at both the live vector and foreign antigen. If these target immunogens are encoded by multicopy expression plasmids, these undesirable metabolic fluxes can result in plasmid loss in the absence of selective pressure, which ultimately defeats the strategy of live vector-mediated delivery of vaccine antigens.

Effective genetic stabilization systems have been developed for enhancing the retention of multicopy plasmids encoding regulated synthesis of foreign antigens, without the further requirement to select with antibiotics.[3,4,5] Antigen export systems have also been developed to reduce proteolytic degradation of foreign antigens within the cytoplasm and more effectively deliver these antigens to the immune system to enhance immunogenicity. [6,7,8,9] Thus, a variety of genetic techniques and technologies are now available for efficient delivery of one or more antigens using live vector vaccines. However, significant problems remain associated with this technology. For example inclusion of more than one gene encoding a foreign antigen of interest within a single multicopy plasmid can lead to large plasmids which ultimately prove to be genetically unstable, reducing both antigen synthesis and the ensuing immune responses. [10]

Novel strategies for engineering live vector vaccines to express high levels of a foreign antigen or to express two or more different antigens are needed.

BRIEF SUMMARY OF INVENTION

The present invention is based on a novel strategy of engineering live vector vaccines to have antigen expression cassettes encoding an antigen of interest integrated into two or more different chromosomal locations, and optionally carrying a plasmid-based expression system. Live vector vaccines engineered in this manner can deliver sufficiently immunogenic levels of the chromosomally encoded antigens to a subject. The strategic integration of antigen expression cassettes into multiple locations within the chromosome of the selected live vector results in production of sufficient levels of the encoded antigen, while avoiding adverse effects on the fitness and growth rate of the vector.

In a first embodiment, the invention is directed to an attenuated strain of *Salmonella enterica* serovar *Typhi* (hereinafter "*S. Typhi*") having disruptions of two or more chromosomal locations selected from the group consisting of the guaBA locus, the htrA locus, the clyA locus, the rpoS locus, and the ssb locus. In one aspect of this embodiment, the attenuated strain of *S. Typhi* is the strain CVD 910 which has disruptions of the guaBA locus, the htrA locus, and the rpoS locus.

In a second embodiment, the invention is directed to an antigen-encoding attenuated strain of *S. Typhi*, wherein the strain comprises:

(a) disruptions of two or more chromosomal locations, wherein the chromosomal locations are selected from the group consisting of the guaBA locus, the htrA locus, the clyA locus, the rpoS locus, and the ssb locus, and (b) chromosomal-based expression systems integrated into the locations of the chromosomal disruptions, wherein each chromosomal-based expression system comprises an antigen expression cassette encoding an antigen of interest.

In one aspect of this embodiment, the antigen of interest is a protective antigen of, for example, an unrelated bacterial, viral, parasitic, or fungal pathogen. In a particular aspect, the antigen of interest is one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, each chromosomal-based expression system comprises an antigen expression cassette encoding a different antigen of interest.

In another aspect of this embodiment, the antigen-encoding attenuated strain of *S. Typhi* is the strain CVD 910 which has disruptions of the guaBA locus, the htrA locus, and the rpoS locus, and which has a chromosomal-based expression system integrated into each site of disruption that encodes one or more antigens of interest. In a particular aspect, the antigen-encoding attenuated strain of *S. Typhi* is the strain CVD 910-3A which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A.

In a third embodiment, the invention is directed to an antigen-encoding attenuated strain of *S. Typhi*, wherein the strain comprises:

(a) disruptions of two or more chromosomal locations, wherein the chromosomal locations are selected from the group consisting of the guaBA locus, the htrA locus, the clyA locus, the rpoS locus, and the ssb locus, (b) chromosomal-based expression systems integrated into the locations of the chromosomal disruptions, wherein each chromosomal-based expression system comprises an antigen expression cassette encoding an antigen of interest, and (c) one or more plasmid-based expression systems, wherein each plasmid-based expression system encodes an antigen of interest.

In one aspect of this embodiment, the antigens of interest are individually protective antigens of, for example, unrelated bacterial, viral or parasitic pathogens. In a particular aspect, the antigens of interest are individually one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, the antigens of interest are different.

In another aspect of this embodiment, the antigen-encoding attenuated strain of *S. Typhi* is the strain CVD 910-3A which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A, a further disruption in the ssb locus, and which has an SSB-stabilized plasmid-based expression system. In a particular aspect, the antigen-encoding attenuated strain of *S. Typhi* is the strain CVD 910-3Assb(pSEC10-CBD/B) which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A, a further chromosomal deletion of the ssb locus, and an SSB-stabilized plasmid-based expression system encoding the cell binding domain of *C. difficile* toxin B.

In a fourth embodiment, the invention is directed to an antigen-encoding attenuated strain of *S. Typhi*, wherein the strain comprises:

(a) disruptions of four chromosomal locations, wherein the chromosomal locations are selected from the group consisting of the guaBA locus, the htrA locus, the clyA locus, and the rpoS locus, (b) chromosomal-based expression systems integrated into the locations of the chromosomal disruptions, wherein each chromosomal-based expression system comprises an antigen expression cassette encoding an antigen of interest, and (c) a plasmid-based expression system, wherein the plasmid-based expression system encodes an antigen of interest.

The antigens of interest may be the same or different in a single strain, and a single copy or multiple copies of the same antigen can be expressed in a single strain. In one aspect of this embodiment, the antigens of interest are protective antigens of, for example, unrelated bacterial, viral or parasitic pathogens. In a particular aspect, the antigens of interest are one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, the attenuated strain of *S. Typhi* expresses three different antigens of interest.

In another aspect of this embodiment, the antigen-encoding attenuated strain of *S. Typhi* is the strain CVD 910-3A which has disruptions of the guaBA locus, the htrA locus, the rpoS locus and the clyA locus, and which comprises antigen expression cassettes integrated into the locations of chromosomal disruption, wherein at least one of the antigen expression cassettes encodes the cell binding domain of *C. difficile* toxin A (CBD/A), wherein at least one of the antigen expression cassettes encodes the binary toxin (BT) of *C. difficile*, which has a further disruption in the ssb locus, and which has an SSB-stabilized plasmid-based expression system expressing the cell binding domain of *C. difficile* toxin B (CBD/B). In a particular embodiment, three of the antigen expression cassettes encode the cell binding domain of *C. difficile* toxin A (CBD/A) and one of the antigen expression cassettes encodes the binary toxin (BT) of *C. difficile*. In a further particular embodiment, two of the antigen expression cassettes encode the cell binding domain of *C. difficile* toxin A (CBD/A) and two of the antigen expression cassettes encode the binary toxin (BT) of *C. difficile*.

In a particular aspect, the antigen-encoding attenuated strain of *S. Typhi* is the strain CVD 910-3A-GB2ssb (pSEC10-CBD/B) which comprises (i) disruptions of the guaBA locus, the htrA locus, the rpoS locus and the clyA locus, and which comprises antigen expression cassettes integrated into the locations of chromosomal disruption, wherein antigen expression cassette located in guaBA chromosomal disruption encodes the binary toxin (BT) of *C. difficile*, wherein antigen expression cassettes located in htrA, rpoS and clyA chromosomal disruptions encode the cell binding domain of *C. difficile* toxin A (CBD/A), (ii) a disruption in the ssb locus, and (iii) an SSB-stabilized plasmid-based expression system encoding the cell binding domain of *C. difficile* toxin B (CBD/B.

In a fifth embodiment, the invention is directed to a live vector vaccine comprising an antigen-encoding attenuated strain of *S. Typhi* as defined herein, and a pharmaceutically-acceptable carrier or diluent.

In a sixth embodiment, the invention is directed to methods of inducing an immune response to an antigen of interest in a subject, comprising administering to a subject an antigen-encoding live vector vaccine as defined herein that expresses an antigen of interest.

In a seventh embodiment, the invention is directed to methods of vaccinating a subject with a protective antigen, comprising administering to a subject an antigen-encoding live vector vaccine as defined herein that expresses a protective antigen.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of use, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
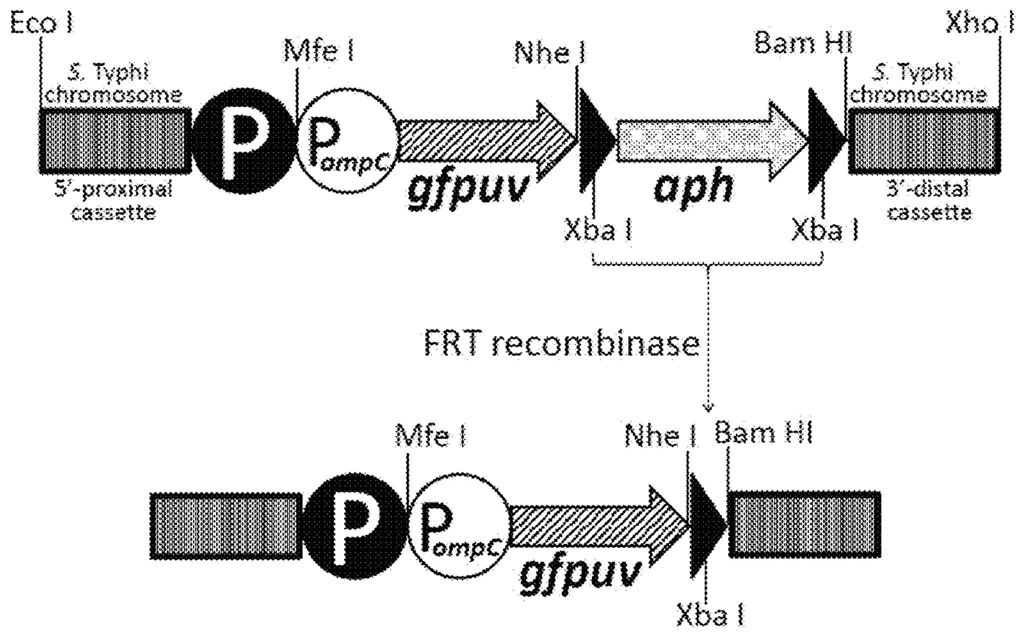
FIG. 1. Schematic depiction of the strategy for chromosomal integration of the antigen expression cassette $P_{ompC}$-gfpuv, encoding the model fluorescent antigen GFPuv. An osmotically-controlled GFPuv-encoding cassette (tandem white circle and hatched thick arrow) was constructed and linked to an aph marker encoding resistance to kanamycin (shaded thick arrow), flanked by FRT recombination sites (black triangles). The incoming $P_{ompC}$-gfpuv-aph cassette was integrated into the live vector chromosome using the λ Red recombination system, followed by removal of the aph marker using FLP recombinase, to yield the final live vector strain bearing no genes encoding resistance to antibiotics. The bacterial chromosome is represented by 5'-proximal and 3'-terminal darkened rectangles, and the black circle labeled with a "P" represents the wild-type chromosomally-encoded promoter of the deleted target open reading frame (e.g., guaBA or htrA).

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Live vectors engineered for delivery of foreign antigens to the host immune system have performed well in experimental animal models, but have been only modestly successful in clinical trials. [20] Given the advances in the development of powerful plasmid-based expression technologies designed to deliver ample levels of foreign protein, it is unlikely that the lack of antigen-specific immunity observed in clinical trials is due to insufficient antigen synthesis following immunization. To the contrary, it is likely that inappropriate antigen synthesis occurring in vivo results in sufficient shock to the metabolism of the live vector to over-attenuate the strain and destroy immunogenicity. Although various attempts have been made to control the timing of foreign protein synthesis, using tightly regulated promoters to control transcription of genes in response to host environmental signals for example, improved immunogenicity in animals has not translated into improvements in clinical trials.[12,21,22]

A novel and elegant solution to this dilemma is presented here, wherein over-attenuation is circumvented by linking antigen synthesis to the growth rate of the live vector vaccine, such that synthesis is initially low after immunization, but steadily increases as the vaccine strain adjusts to prevailing environmental conditions and undergoes limited replication within the host. This expression strategy allows for efficient expression of one or even multiple foreign antigens within a single live vector vaccine strain. It can also be used in conjunction with plasmid-based methods by distributing the location of antigen expression cassettes between the chromosome and an expression plasmid. The approach presented herein thus offers the flexibility of independently adjusting the copy number of potentially toxic foreign genes by integrating a designated number of copies into the chromosome. By appropriate integration of foreign genes into chromosomal loci whose induction of expression is intimately associated with the physiology and growth rate of the vaccine strain, it becomes possible to "tune" foreign antigen synthesis to the metabolic state of the live vector.

The present invention is therefore based on the discovery that delivery of sufficiently immunogenic levels of chromosomally-encoded antigens to a subject can be accomplished through strategic integration of antigen expression cassettes into multiple locations within the live vector chromosome, thereby compensating for loss of copy number afforded by systems using stable low copy plasmids, while avoiding further attenuation of the vaccine strain. Integration of multiple cassettes also avoids the need for strong constitutive promoters to enhance antigen synthesis from a single gene copy, an approach which does not necessarily lead to adequate antigen synthesis or immune responses.[11,12]

The present invention is directed to several related embodiments, including (i) an attenuated strain of *S. Typhi* having disruptions of two or more chromosomal locations selected from the group consisting of the guaBA locus, the htrA locus, the clyA locus, the rpoS locus, and the ssb locus, and (ii) antigen-expressing attenuated strains of *S. Typhi* having a chromosomal-based expression system which comprises an antigen expression cassette integrated into two or more locations of chromosomal disruptions, (iii) antigen-expressing attenuated strains of *S. Typhi* having a chromosomal-based expression system which comprises an antigen expression cassette integrated into two or more locations of chromosomal disruptions as well as a plasmid-based expression system, (iv) a live vector vaccine comprising an antigen-expressing attenuated strain of *S. Typhi* as defined herein, and a pharmaceutically-acceptable carrier or diluent, (v) methods of inducing immune responses to an antigen of interest in a subject using the live vector vaccines as defined herein, and (vi) methods of vaccinating a subject using the live vector vaccines as defined herein.

Attenuated Strains of *S. Typhi*

As suggested above, in one embodiment the present invention is directed to attenuated strains of *Salmonella enterica* serovar *Typhi* having disruptions of two or more chromosomal locations. *S. Typhi* is a well-tolerated live vector that can deliver multiple unrelated immunogenic antigens to the human immune system. *S. Typhi* live vectors have been shown to elicit antibodies and a cellular immune response to an expressed antigen. *S. Typhi* is characterized by enteric routes of infection, a quality which permits oral vaccine delivery. *S. Typhi* also infects monocytes and macrophages and can therefore target antigens to professional APCs.

The genetic disruptions are sufficiently extensive to ensure that active forms of the protein(s) encoded by the locus harboring the disruption are not produced by the bacteria. While the skilled artisan will understand that the characteristics and scope of the disruptions can vary widely, in one non-limiting aspect the disruptions are sufficiently extensive to ensure that neither the protein(s) encoded by the locus, nor fragments thereof, can be detected in bacteria having the disruptions.

The skilled artisan will recognize that strains of bacteria having the disruptions can be readily produced via several techniques known in the art, including the λ Red-mediated site-directed mutagenesis method. [16] Other, less efficient, chromosomal deletion/integration technologies used in the past involve the use of suicide plasmids. These suicide plasmids exhibit replication which is exclusively dependent on the pir protein; successful deletions/integrations are dependent on recA-mediated homologous chromosomal crossovers, and counter-selection with sacB. [29]

The chromosomal locations having the two or more disruptions are the guaBA locus, the htrA locus, the clyA locus, the rpoS locus, and the ssb locus. The disruptions of these loci can be disruptions of the endogenous coding sequences, non-coding control sequence, promoter sequences, or a combination thereof. In the case of the guaBA locus, for example, the coding region can be disrupted without damaging the promoter sequence for the loci.

The chromosomal disruptions can include any combination of deletions or insertions of sequences comprising the disrupted loci.

The attenuated strains of *S. Typhi* may have disruptions in any combination of two, three or four of the loci and sites, or even all five of the loci.

Specific examples of such attenuated strains of *S. Typhi* including strain CVD 910, which contains disruptions in the guaBA locus and the htrA locus. Because the parent Ty2 strain used in the production of CVD 910 has the rpoS locus naturally inactivated, CVD 910 also contains a disruption of the rpoS locus. Thus, CVD 910 contains disruptions in three chromosomal locations: the guaBA locus, the htrA locus, and the rpoS locus.

Antigen-Encoding Attenuated Strains of *S. Typhi*

As suggested above, in a related embodiment the invention is directed to antigen-encoding attenuated strains of *S. Typhi* having a chromosomal-based expression system integrated into two or more of the disrupted chromosomal locations within the bacteria. Thus, the invention includes the attenuated strains of *S. Typhi* as defined herein, including strain CVD 910, which have been engineered to have antigen expression cassettes integrated into the locations of chromosomal disruptions.

The chromosomal-based expression systems used in the antigen-encoding attenuated strains of *S. Typhi* are simple in nature in that they comprises a genetic cassette (antigen expression cassette) comprising the coding sequence of an antigen of interest and, optionally, an exogenous promoter to direct transcription of the coding sequence. In some circumstances and depending on the identity of the coding sequence and/or promoter, additional 5' and/or 3' non-coding sequence associated with the coding sequence of the antigen of interest can be included in the cassette. Together, these sequences make up an antigen expression cassette that can be inserted into one or more disrupted bacterial chromosomes. Because the attenuated strains of *S. Typhi* defined herein have at least two chromosomal disruptions, antigen expression cassettes encoding different antigens can be used in the same strain of bacteria. In those strains of *S. Typhi* having three chromosomal disruptions, up to three different antigens may be expressed, with up to four different antigens in those strains of *S. Typhi* having four chromosomal disruptions, and up to five different antigens in those strains of *S. Typhi* having five chromosomal disruptions. The skilled artisan will also recognize that different combinations of antigens can be expressed in a given strain depending on the number of disruptions and the selected antigen expression cassettes. For example, where a strain has three disruptions, the same antigen expression cassette (encoding antigen A, for example) can be inserted into each of the three sites. Alternatively, an antigen expression cassette encoding antigen A could be inserted into two of the sites, while an antigen expression cassette encoding antigen B could be inserted into the third site. In a further alternative, an antigen expression cassette encoding antigen A could be inserted into one of the sites, an antigen expression cassette encoding antigen B could be inserted into the second site, and an antigen expression cassette encoding antigen C could be inserted into the third site. Thus, the identity of the antigen encoded by each antigen expression cassette is individually selected and any combination of antigens may be used. This expressly includes instances where a particular antigen is encoded by two or more cassettes as well as instances where a particular antigen is encoded by only one cassette.

Antigens

The antigen expression cassettes of the present invention preferably express an antigen for presentation to a host to elicit an immune response resulting in immunization and protection from disease. The antigens of interest that may be expressed in the attenuated strains of *S. Typhi* of the present invention are unlimited in identity and include, but are not limited to, antigens from foreign bacteria (e.g., proteins not already expressed by *S. Typhi*), viruses, and parasitic organisms. Exemplary antigens are protective antigens (i.e., an antigen that when bound by an antibody, result in the death of the organism expressing the antigen). Because the attenuated strains of *S. Typhi* may be used as live vector vaccines, one practicing the invention will be motivated, in one aspect, to use antigens suspected of or known to induce a protective immune response in a subject. As another example, antigens suspected of or known to induce an active immune response in a subject to pre-existing infection may also be used.

Exemplary antigens that can be used to induce a protective immune response include detoxified versions of enterotoxin A (TcdA), enterotoxin B (TcdB), and binary toxin (transferase; Cdt) of *Clostridium difficile*, and fragments thereof, such as the cell-binding domains of TcdA and TcdB, and the binding domain of Cdt (CdtB). These antigens can be used to produce a mono-, bi- or multivalent live vector vaccine that in turn can be used to vaccinate a subject against infections caused by *C. difficile*. With the ability to impart immunity that recognizes both toxins and putative colonization factors, a subject can be vaccinated against disease that occurs at two critical stages of infection—colonization and toxin production.

Additional exemplary antigens include the LcrV antigen and the capsular F1 antigen of *Yersinia pestis*, which are required for secretion of virulence effectors proteins and are virulence factors themselves. Additional *Yersinia pestis* antigens include pH 6 antigen (Psa), a putative colonization factor, and Yop B/YopD, two essential proteins comprising the translocon region of the type 3 secretion (T3SS) needle.

Given the ease with which antigen expression cassettes can be produced, and the straightforwardness of inserting and removing the cassettes from locations of chromosomal disruptions in bacteria, it will be clear to the skilled artisan that a very wide range of different antigens can be expressed using the chromosomal-based expression systems of the attenuated strains of *S. Typhi* defined herein. These same antigens can also be expressed in the bacteria using the plasmid-based expression systems discussed below.

Plasmid-Based Expression Systems

In a related embodiment, the invention is also directed to antigen-encoding attenuated strains of *S. Typhi* having the chromosomal-based expression system discussed above, as well as a plasmid-based expression system. The inclusion of a plasmid-based expression system within the bacteria provides additional flexibility for expressing antigens of interest in the attenuated strains of *S. Typhi* of the invention. The plasmid-based expression system allows expression of additional copies of an antigen expression cassette that is integrated into the bacterial chromosome or an antigen expression cassette encoding an antigen of different identity. Thus, as defined herein the antigen expression cassettes can be inserted to both the locations of chromosomal disruptions (in terms of the chromosomal-based expression systems) and expression plasmids (in terms of the plasmid-based expression systems).

SSB-Stabilized Plasmid-Based Expression System

Examples include the plasmid-based expression systems disclosed in U.S. Pat. Nos. 6,703,233, 6,969,513, 6,977,176, 7,141,408, 7,125,720 and 7,138,112, each of which is incorporated herein by reference in their entirety. The systems described in these patents are multicopy expression plasmids into which plasmid maintenance systems have been incorporated. Such multicopy expression plasmids produce a gene dosage effect which enhances the level of expression of the antigen of interest. In a specific example, a plasmid-based expression system has been developed in which a low copy expression plasmid has been engineered to encode an essential single-stranded binding protein (SSB) which has been deleted from the bacterial vaccine strain. Since SSB is essential for DNA replication, recombination, and repair, ssb-deleted bacteria must maintain the expression plasmid to enable survival. Therefore, if SSB-stabilized plasmids are used to encode one or more foreign antigens, then bacteria become committed to foreign antigen synthesis. If expression of foreign antigens in the cytoplasm of the bacteria becomes toxic, antigen export systems can be further introduced into these SSB-stabilized plasmids to export fusion proteins out of the cytoplasm and minimize metabolic disruption.

ClyA Fusion Protein Plasmid-Based Expression Systems

A further example of a suitable plasmid-based expression system is disclosed in WO 09/149083, incorporated herein by reference in its entirety, which makes use of the *S. Typhi* HlyE family of export proteins, including the cryptic hemolysin (ClyA), encoded by the cytolysin A gene (clyA). ClyA from *S. Typhi* was first described by Wallace et al. who also reported the crystal structure for the homologous hemolysin from *E. coli*. [26] This hemolysin has been described previously and variously referred to as ClyA, HlyE, or SheA.

The crystal structure of ClyA in *E. coli* has been resolved. [26] The unique structure can be roughly divided into several domains, a head domain, a body domain and a tail domain. The body domain consists of a bundle of helixes (A, B, C, D, F). The tail domain is a helix G which extends to half the length of the body. The head domain consists of a short β hairpin (β-tongue) and two small helices (D and E), each flanking the β-tongue. It was suggested that the β-tongue might be critical for pore formation and hence for the hemolytic activity. [26] Through site directed mutagenesis, it was found that many regions of ClyA were important for the hemolytic activity. [27]

The ClyA protein is exported from both *E. coli* and *S. Typhi* and it is capable of exporting passenger proteins (and antigens of interest) that have been genetically fused to the 3'-terminus of the clyA open reading frame. It is demonstrated that the proper folding of these fusion proteins occurs such that the inherent biological activity of the domains involved is maintained.

The amino acid and nucleotide sequence for the isolated *S. Typhi* clyA gene and ClyA protein (from *Salmonella* serovar *Typhi* strain Ty2) are provided as SEQ ID NO:39 and SEQ ID NO:38, respectively. A synthetic codon-optimized version of the *S. Typhi* clyA gene, as described and utilized herein, is provided in SEQ ID NO:40. Other HlyE family members that may be utilized as export proteins herein are also available and known to those of ordinary skill in the art. The family members include a second *S. Typhi* cytolysin A (the clyA gene is set forth in SEQ ID NO:41 and it is available under GENBANK Accession No. AJ313034); *Salmonella paratyphi* cytolysin A (the clyA gene sequence for cytolysin A is set forth in SEQ ID NO:42 and it is available under GENBANK Accession No. AJ313033); *Shigella flexneri* truncated HlyE (the hlyE gene sequence is set forth in SEQ ID NO:43 and it is available under GENBANK Accession No. AF200955); *Escherichia coli* HlyE (the hlyE gene sequence is set forth in SEQ ID NO:44 and it is available under GENBANK Accession No. AJ001829).

As indicated above, the HlyE family of proteins typically causes cytolysis of target cells, including hemolysis of erythrocytes. Because cytolysins/hemolysins may be considered to be virulence factors, the present invention encompasses the use of variants of HlyE family members that have been mutated such that they lack, or have reduced, hemolytic activity. The ability of these variants to be exported from a bacterial cell producing them, alone or in the context of fusion to a protein of interest, has been maintained. Thus, the non-hemolytic variants of HlyE family members have reduced or no hemolytic activity, and yet are fully functional in the plasmid-based expression systems of the present invention. Such variants include the *S. Typhi* cytolysin A (ClyA) protein of SEQ ID NO:38 having a single mutation selected from the group consisting of an 5195N mutation, an I198N mutation, an A199D mutation, an E204K mutation, and a C285W mutation; an I198N, C285W double mutation; and an I198N, A199D, E204K triple mutation. The *S. Typhi* cytolysin A (ClyA) protein may also have the amino acid sequence set forth in SEQ ID NO:38 and a C285W mutation, as well as one additional mutation selected from the group consisting of an I198N mutation, an A199D mutation, and an E204K mutation.

The plasmid-based expression systems comprising ClyA fusion proteins described herein can be used to express and export a wide variety of fusion proteins comprising an export protein and an antigen of interest. The export protein::antigen of interest fusion protein construct is present in an antigen expression cassette, which in turn is present in an expression plasmid to facilitate the recombinant production of the protein of interest. Typically the expression plasmid will comprise an origin of replication and other structural features that control and regulate the maintenance of the expression plasmid in the host cell. Exemplary expression plasmids are well known to the skilled artisan.[7,23,28] The key aspect of such expression plasmids is copy number, which can range from several hundred per chromosomal equivalent to one per chromosomal equivalent. Preferably the copy number of the expression plasmids is between 5 and 15 copies per chromosomal equivalent.

Live Vector Vaccines

As suggested above, and in a related embodiment, the invention is directed to a live vector vaccine comprising one or more of the antigen-encoding attenuated strains of *S. Typhi* as defined herein, and a pharmaceutically-acceptable carrier or diluent.

It is contemplated that the live vector vaccines of the present invention will be administered as pharmaceutical formulations for use in vaccination of individuals, preferably humans. In addition to the strains of *S. Typhi*, the vaccines will thus include pharmaceutically-acceptable carriers, and optionally, may include other therapeutic ingredients, such as various adjuvants known in the art.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the compounds which are desirable and efficacious for the vaccination application. However, the live vector vaccines are delivered in an amount capable of eliciting an immune reaction in which it is effective to increase the subject's immune response to the antigen(s) of interest. An immunogenic amount is an amount which confers an increased ability to prevent, delay or reduce the severity of the onset of a disease, as compared to such abilities in the absence of such immunization. It will be readily apparent to one of skill in the art that this amount will vary based on factors such as the weight and health of the recipient, the type of antigen(s) being expressed, the type of infecting organism being combatted, and the mode of administration of the vaccines.

The vaccines may be formulated for any suitable means and/or methods for delivering the live vector vaccines to a corporeal locus of the subject where the live vector vaccines are intended to be effective in triggering an immune response, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), and intramuscular (i.m.). Any known device useful for parenteral injection or infusion of vaccine formulations can be used to effect such administration. In preferred aspects of each of the embodiments on the invention, the vaccines are administered to a subject as an oral formulation, in particular, to the oral mucosa.

The dose rate and suitable dosage forms for the live vector vaccines of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

Formulations of the vaccines can be presented, for example, as discrete units such as capsules, cachets, tablets or lozenges, each containing a predetermined amount of the vaccine; or as a suspension.

Depending on the means of administration, the vaccines may be administered all at once, such as with an oral formulation in a capsule or liquid, or slowly over a period of time, such as with an intramuscular or intravenous administration. The vaccines may also be administered to the subject more than once, as boosters, for example, where administration of separate doses of the vaccines may be separated in time by hours, days, weeks or months.

In each embodiment and aspect of the invention, the subject is a human, a non-human primate, bird, horse, cow, goat, sheep, a companion animal, such as a dog, cat or rodent, or other mammal.

Manners of Use

As indicated above, it is intended that the antigen-encoding attenuated strains of *S. Typhi* defined herein will be grown under conditions that may induce expression of the antigens of interest prior to immunization, and formulated as a live vector vaccine for administration to a subject, whereupon an immune response to the antigens of interest, inter alia, will be induced in the subject.

The invention therefore includes methods of inducing an immune response to an antigen of interest in a subject, comprising administering to a subject a live vector vaccine as defined herein and that expresses an antigen of interest. The invention also includes methods of vaccinating a subject with a protective antigen, comprising administering to a subject a live vector vaccine as defined herein that expresses a protective antigen.

The methods contemplate and include administering the live vector vaccine to the subject only once, or more than once, such as 2, 3, 4, 5 or more times.

A non-limiting example of the manner in which the vaccines may be used includes use of the vaccine as a nosocomial oral vaccine, administered to patients seven days after antibiotic treatment for *Clostridium difficile* infection (CDI) to block recurrent disease by eliciting a vigorous and rapid anamnestic response in patients primed by the initial *C. difficile* infection.

IV. Examples

Materials and Methods

Bacterial Strains and Culture Conditions.

The attenuated *S. enterica* serovar *Typhi* (*S. Typhi*) live vector vaccine strain CVD 910 used in these studies is an auxotrophic derivative of wild-type strain Ty2, with deletions in guaBA and htrA. To improve the clinical acceptability of the live vector vaccine strains, all genetic and bacteriologic manipulations of the live vectors were performed using an animal product-free medium equivalent to Luria-Bertani medium, comprised of 10 g/liter of Soytone (Teknova; S9052), 5 g/liter Hy-Yest 412 (Sigma; Y1001), and 3 g/liter NaCl (American Bioanalytical; AB01915), supplemented with 0.002% guanine (Sigma; G6779).

Construction of Chromosomal Integrations.

Deletion cassettes were constructed for use with the λ Red-mediated site-directed mutagenesis method [16] to delete either guaBA, htrA, or clyA from wild-type *S. Typhi* Ty2. Cassettes encoding upstream and downstream flanking chromosomal sequences were constructed using primer pairs listed in Table 1 and purified chromosomal DNA from Ty2 as the template DNA.

TABLE 1

Primers used in the construction and testing of live vector strains expressing chromosomally-encoded GFPuv.

| Primer (SEQ ID NO:) | Sequence[a] |
|---|---|
| 5guaBA-for SEQ ID NO: 1 | 5'- GAATTCTAGCTGCTCATACTTCTGCTGCA -3' |
| 5guaBA-rev SEQ ID NO: 2 | 5'- GCTAGCCAATTGGGGCAATATCTCACCTGG -3' |
| 3guaBA-for SEQ ID NO: 3 | 5'- GGATCCACTAGTGTCGATAACCCTTCCTGTGT -3' |
| 3guaBA-rev SEQ ID NO: 4 | 5'- CTCGAGACAGCACCTACAAGTCTGGCATG -3' |
| guaBA PCR-for SEQ ID NO: 5 | 5'- GCGCTGACCACCGGAATACGGCTG -3' |
| guaBA PCR-rev SEQ ID NO: 6 | 5'- CATGGCATGGATGAGGCAACCGCGAAGC -3' |
| 5htrA-for SEQ ID NO: 7 | 5'- GAATTCGTACCTTCAATCAGGCGTTACTGGAAGATG -3' |
| 5htrA-rev SEQ ID NO: 8 | 5'- GCTAGCCAATTGCGATTAACAGGTAACGCAAAATTGCTGTGTACGTCAG -3' |
| 3htrA-for SEQ ID NO: 9 | 5'- GGATCCACTAGTCTGCGTAAGATTCTCGACAGCAAGCCGTCGGT -3' |
| 3htrA-rev SEQ ID NO: 10 | 5'- CTCGAGCCAGCATCATTTCGGCAGTCATACACACCAGTTCGC -3' |
| htrA PCR-for SEQ ID NO: 11 | 5'- GTGTCGCCGATCTTGAAGACGCGGTAGAG -3' |
| htrA PCR-rev SEQ ID NO: 12 | 5'- CTATCGACGCCAAGCTGGCCGCTGTCGAC -3' |
| 5clyA-for SEQ ID NO: 13 | 5'- TAGTAATGAGAATTCGCTGGTATTGATCGGCTCTCCGGTAGAGATTAGCGA -3' |
| 5clyA-rev SEQ ID NO: 14 | 5'- GCTAGCCAATTGTGCCTCTTTAAATATATAAATTGCAATTAAGTACCTG -3' |

TABLE 1-continued

Primers used in the construction and testing of live vector strains expressing chromosomally-encoded GFPuv.

| Primer (SEQ ID NO:) | Sequence[a] |
|---|---|
| 3clyA-for SEQ ID NO: 15 | 5'- GGATCCACTAGTGATACATTTTCATTCGATCTGTGTACTTTTAACGCCCGAT AGCG -3' |
| 3clyA-rev SEQ ID NO: 16 | 5'- TGATAGTAACTCGAGACAATCCATAAGAAAGGTCAGGCACACTGGGAAGG CGACATC -3' |
| clyA PCR-for SEQ ID NO: 17 | 5'- CATGATGGTATCCAGTATGGCACAAGC -3' |
| clyA PCR-rev SEQ ID NO: 18 | 5'- GTAATCGACAACATGCTACATCCATCG -3' |
| 5FRT-aph-for SEQ ID NO: 19 | 5'- GAATTCGCTAGCGCTGGAGCTGCTTCGAAGTTC -3' |
| 3FRT-aph-rev SEQ ID NO: 20 | 5'- CTCGAGTTCCGGGGATCCGTCGACCTGCAGTTC -3' |
| 5gfpuv SEQ ID NO: 21 | 5'- CAATTGTGTGGTAGCACAGAATAATGAAAAGT -3' |
| 3gfpuv SEQ ID NO: 22 | 5'- GCTAGCTCATTATTTGTAGAGCTCATCCAT -3' |

[a]Relevant restriction sites are underlined.

These cassettes were used to exchange chromosomal targets with a Tn5 neomycin phosphotransferase cassette (aph), encoding resistance to kanamycin, and recombined into the chromosome using the λ Red recombination system encoded by pKD46. Final removal of the kanamycin resistance cassette was accomplished using FLP recombinase encoded by pCP20. The integrity of the intended chromosomal deletion mutations was confirmed by DNA sequence analysis of the chromosomal locus from each strain using PCR primers listed in Table 3. For chromosomal expression of GFPuv, an antigen expression cassette in which an osmotically regulated ompC promoter ($P_{ompC}$ [23]) was linked to gfpuv was selected and inserted 5'-proximal to the aph resistance marker of chromosomal deletion cassettes. As shown in FIG. 1, care was taken to preserve the natural chromosomal promoters controlling transcription of chromosomally encoded targets, with the intent that synthesis of GFPuv would ultimately be controlled both by osmolarity (via $P_{ompC}$) as well as growth rate in the case of the guaBA locus,[15] heat shock/environmental stress in the case of the htrA locus,[18] or possibly low pH for clyA. [19]

Flow Cytometry.

GFPuv-expressing strains were grown overnight at 37° C. on rich solid medium supplemented with guanine. 2-3 fluorescing colonies were then inoculated into 20 ml of supplemented liquid medium and incubated with shaking at 250 rpm overnight at 37° C. Overnight starter cultures were then diluted 1:100 into fresh supplemented liquid medium and incubated at 37° C., 250 rpm. For growth curve studies, 5 ml volumes were periodically removed from incubating cultures, from which bacteria from 4 ml were pelleted, while the remaining 1 ml volume was used to measure the optical density at 600 nm ($OD_{600}$). Pelleted bacteria were resuspended in 1 ml of PBS, and cells then diluted 1:1,000 in PBS prior flow analysis. Quantitation of GFPuv fluorescence was analyzed using a MoFlo Legacy flow cytometer/cell sorter system (Beckman Coulter) with the argon laser exciting bacteria at 488 nm and emissions detected at 525 nm. Forward versus side light scatter, measured with logarithmic amplifiers, was used to gate on bacteria. A minimum of 50,000 events were acquired from each sample at a collection rate of approximately 3,500 events per second. The mean fluorescence intensity was determined using Summit software (Beckman Coulter). Background autofluorescence was determined using the negative control *S. Typhi* vaccine strain CVD 910.

Results

Construction of CVD 910.

The attenuated vaccine candidate CVD 908-htrA, derived from Ty2 and carrying deletions in aroC, aroD, and htrA, was previously constructed and proved to be safe and highly immunogenic in Phase 2 clinical trials.[13] Here, a new vaccine strain, CVD 910, was constructed that carries deletions in guaBA and htrA. The ΔaroC ΔaroD was replaced with the single deletion ΔguaBA for two important reasons: 1) previous work by the inventors showed that ΔguaBA alone sufficiently attenuates Ty2, resulting in a live vector strain capable of eliciting impressive humoral immunity to a plasmid-encoded foreign antigen using the murine intranasal model of immunogenicity;[14] and 2) transcriptional control of the guaBA locus is controlled by growth rate, independent of guanine-mediated repression,[15] allowing expression of properly integrated antigen expression cassettes to be increased as the live vectors grow in the host. In order to reduce the risk of reversion to virulence by the unlikely acquisition of wild type guaBA genes, a secondary deletion of htrA which encodes a heat shock-induced serine protease was further engineered.

Deletion cassettes targeting guaBA and htrA were constructed for use with the λ Red-mediated site-directed mutagenesis method,[16] and each cassette was used to successfully delete either guaBA or htrA from wildtype *S. Typhi* Ty2. Introduction of both deletion mutations into a single strain resulted in the creation of CVD 910. A preliminary assessment of attenuation of CVD 910 was carried out by comparing the minimum lethal dose causing death in 50% of a group of BALB/c mice (LD50) for CVD 910 versus CVD 908-htrA, using the hog gastric mucin intraperitoneal murine challenge model. For this model, the guidelines recommended in the Code of Federal Regulations for Food and Drugs, Title 21, Part 620.13 (c-d), 1986 for intraperitoneal challenge of mice with *S. Typhi* were broadly followed. Using this method, the LD50 for both CVD 910 and CVD 908-htrA was determined to be approximately $5\times10^5$ CFU (data not shown), versus an LD50 of ~10 CFU for wild-type Ty2,[17] demonstrating construction of a novel live vaccine strain with a safety profile equivalent to that of CVD 908-htrA.

Chromosomal Integration of Gfpuv Cassettes into CVD 910.

Figure 2:
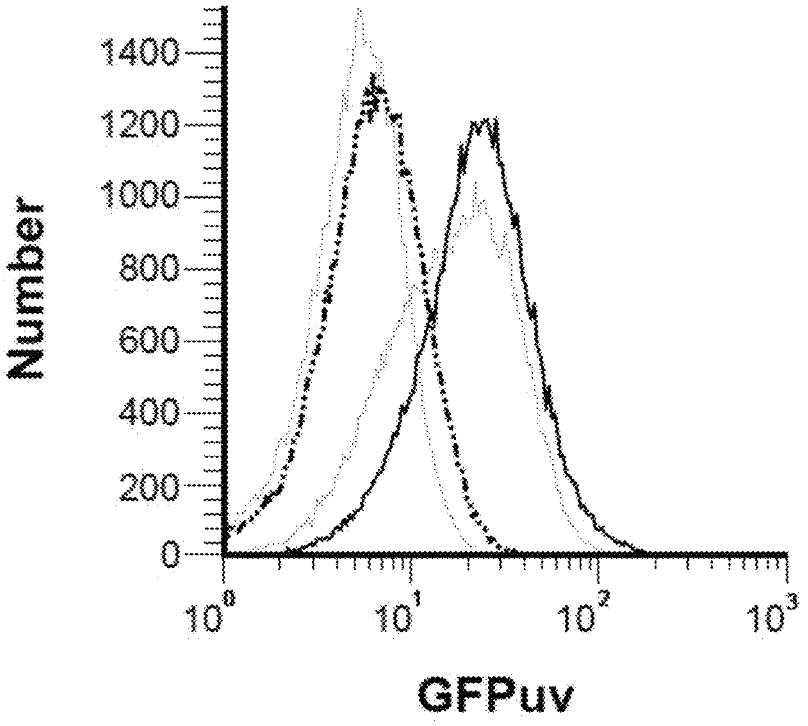
FIG. 2. Flow cytometry histograms of GFPuv-mediated fluorescence encoded by $P_{ompC}$-gfpuv gene cassettes integrated into either the guaBA (thick solid line), htrA (thin hatched line), or clyA (thick broken line) sites of the attenuated *S. Typhi* live vector vaccine candidate CVD 910, compared to the vaccine strain alone (thin dotted line). Fluorescence intensities are measured for individual bacterial cells grown under inducing conditions of 200 mM NaCl in rich medium at 37° C./250 rpm for 16 hr.

GFPuv was expressed from independently controlled cassettes in CVD 910 (containing the guaBA and htrA chromosomal gene deletions) in the following manner. The osmotically regulated $P_{ompC}$ promoter was genetically fused to a promoterless gfpuv gene. The resulting $P_{ompC}$-gfpuv cassette was integrated into either the guaBA or htrA loci such that only the open reading frame was replaced, but the original promoters for both chromosomal loci were preserved, as depicted schematically in FIG. 1. For example, integration of $P_{ompC}$-gfpuv into the guaBA locus to create CVD 910-GG resulted in transcription of gfpuv controlled both by osmolarity (via $P_{ompC}$) and growth rate (via $P_{guaBA}$). Similarly, integration of the same cassette into htrA to create CVD 910-HG resulted in synthesis of GFPuv controlled both by osmolarity ($P_{ompC}$) and heat shock/environmental stress ($P_{htrA}$).[18] In addition, a third chromosomal integration was prepared, CVD 910-CG, in which $P_{ompC}$-gfpuv replaced clyA, encoding a cryptic hemolysin from Ty2 whose transcription is normally controlled by low pH.[19] Interestingly, when the resulting strains were grown overnight at 37° C. in liquid cultures and analyzed for fluorescence by flow cytometry, observed fluorescence intensity was found to be strongly influenced by the site of integration, regardless of osmotic induction of $P_{ompC}$. As shown in the fluorescence histograms of FIG. 2, under inducing conditions of 200 mM NaCl, strains with $P_{ompC}$-gfpuv integrated into either guaBA or htrA displayed remarkably uniform bacterial populations with mean fluorescence intensities of 28.65 and 21.59 respectively, while integration into clyA resulted in a very low mean fluorescence intensity of 7.53, barely above the background autofluorescence of 5.94 detected for CVD 910 alone. Having established substantial expression of GFPuv from two independent chromosomal loci, the hypothesis that integration of $P_{ompC}$-gfpuv into both guaBA and htrA together would result in additive expression of fluorescence was then tested. Analysis of fluorescence from the resulting strain, CVD 910-2G, revealed an uninduced (50 mM NaCl) mean fluorescence intensity of 36.01, which increased to 48.21 after induction with 200 mM NaCl. In this experiment, uninduced fluorescence intensities for CVD 910-GG and CVD 910-HG were 25.35 and 15.85 respectively, while induced fluorescence levels were 32.46 and 24.03 respectively. It is immediately evident that for overnight liquid cultures, cumulative fluorescence observed with two copies of gfpuv integrated into CVD 910-2G is approximately equivalent to the combined fluorescence levels for individual copies of integrated gfpuv observed in CVD 910-GG and CVD 910-HG, under both uninduced and induced osmotic conditions.

Growth-Phase Regulated Expression of GFPuv in CVD 910-2G.

Regulated, but sustained, expression of foreign antigens delivered by live vectors is expected to reduce any metabolic burden associated with antigen synthesis, thereby allowing live vectors to persist longer in immunized hosts and prolong delivery of candidate vaccine antigens to the immune system. [20] However, and despite recent improvements, tightly regulated and appropriately timed antigen expression using plasmid-based expression technologies still remains elusive in many cases, with leaky expression potentially contributing to over-attenuation of live vector vaccine strains. Therefore, one of the goals of the current work was to investigate the feasibility of linking foreign antigen expression to the growth phase of the live vector, such that expression would be reduced when bacteria are adapting to a significant change in environmental conditions (i.e. lag phase), but would be strongly induced after bacteria have successfully adapted their metabolism to new energy sources and environmental conditions (i.e. exponential growth transitioning into stationary phase).

To meet this goal, chromosomally-encoded GFPuv expression in CVD 910-2G was first compared to a previously described live vector CVD 908-htrAssb(pGEN206) [3], in which GFPuv was expressed independently of growth phase from a low copy (~5 copies per chromosomal equivalent) stabilized expression plasmid. Overnight starter cultures of CVD 910-2G and CVD 908-htrAssb(pGEN206) were grown at 37° C. for approximately 16 hrs and then diluted 1:100 into 100 ml of fresh medium in 250 ml baffle flasks. To reduce the influence of osmolarity on growth phase and more clearly establish any link between observed fluorescence and induction of $P_{guaBA}$ and $P_{htrA}$ during growth, all strains were grown under non-inducing conditions of 50 mM NaCl. Fresh cultures were incubated at 37° C./250 rpm, and 5 ml aliquots were removed every hour for 6 hours to measure both $OD_{600}$ and fluorescence intensities by flow cytometry. As expected, plasmid-based expression in CVD 908-htrAssb(pGEN206) significantly slowed the growth kinetics of the live vector when compared to either CVD 910 or CVD 910-2G, even under non-inducing conditions of 50 mM NaCl (Table 2). Initial fluorescence intensities in lag phase started out quite high at 1262.66, dipped during exponential phase to 686.27, and then rose again to 1131.59 in stationary phase. In sharp contrast, the kinetics of GFPuv expression in CVD 910-2G was closely linked to the growth phase of the culture, with a low mean fluorescence intensity of 81.19 measured in the lag phase, which gradually increased with cell density to a maximum fluorescence intensity of 200.06 as the culture reached stationary phase. The observed variation of fluorescence with growth phase, as quantitated by flow cytometry, is not an aggregate effect of increasing cell numbers, but instead reflects the level of GFPuv synthesis within individual bacteria in a growth-rate dependent manner. These data support the feasibility of chromosomal expression of a foreign antigen from multiple integration sites, and the possibility of antigen expression synchronized with growth-rate, a possibility not supported by plasmid-based expression in these experiments.

TABLE 2

Chromosomal versus plasmid-based expression of GFPuv in attenuated *Salmonella Typhi* live vectors.

| Time | CVD 910 | | CVD 910-2G (guaBA::gfpuv htrA::gfpuv) | | CVD 908htrAssb (pGEN206S2) | |
|---|---|---|---|---|---|---|
| (hr) | $OD_{600}$[a] | MFI[b] | $OD_{600}$ | MFI | $OD_{600}$ | MFI |
| 0 | 0.04 | ND[c] | 0.04 | ND | 0.04 | ND |
| 1 | 0.07 | ND | 0.08 | 81.19 | 0.06 | 1262.66 |
| 2 | 0.27 | ND | 0.3 | 96.77 | 0.14 | 1196.59 |
| 3 | 0.71 | ND | 0.71 | 105.59 | 0.38 | 721.34 |
| 4 | 1.36 | ND | 1.36 | 182.77 | 0.72 | 686.27 |
| 5 | 1.88 | ND | 1.86 | ND | 1.25 | ND |
| 6 | 2.18 | 6.34 | 2.18 | 169.87 | 1.67 | 891.53 |
| 7 | 2.29 | ND | 2.29 | 200.06 | 1.95 | 1131.59 |

[a]Cultures grown under non-inducing conditions in 50 mM NaCl.
[b]Mean Fluorescence Intensity.
[c]Not Determined.

This experiment was repeated to compare GFPuv expression from double integrations in CVD 910-2G to single integration expression levels in CVD 910-GG and CVD 910-HG. As summarized in Table 3, growth phase-dependent expression of fluorescence intensity was again observed, increasing from an initial lag phase level of 32.90 to a high of 161.65 in stationary phase. Interestingly, fluorescence levels during the 3 hr lag phase for the double integration did not reflect the sum of fluorescence observed with single integrations during this period, but became additive as the cultures progressed into exponential and stationary phases. Fluorescence intensities from single integrations did not seem to reflect the same dependence on growth phase as observed for the double integration; intensities for the guaBA integration in CVD 910-GG progressed from 74.94 to 96.31 during growth while htrA-controlled fluorescence in CVD 910-HG progressed from 32.90 to 68.94. Despite this anomaly, the data reported here suggest that integration of antigen expression cassettes into multiple loci within a live vector chromosome can be accomplished without further attenuation of the vaccine strain, and that this multiple integration strategy results in superior expression levels of foreign antigens versus conventional integration into a single locus.

TABLE 3

Growth-phase regulated chromosomal expression of GFPuv in CVD 910 attenuated *Salmonella Typhi* live vectors.

| Time | CVD 910 | | CVD 910-GG (guaBA::gfpuv) | | CVD 910-HG (htrA::gfpuv) | | CVD 910-2G (guaBA::gfpuv htrA::gfpuv) | |
|---|---|---|---|---|---|---|---|---|
| (hr) | $OD_{600}$[a] | MFI[b] | $OD_{600}$ | MFI | $OD_{600}$ | MFI | $OD_{600}$ | MFI |
| 0 | 0.04 | ND[c] | 0.04 | ND | 0.03 | ND | 0.02 | ND |
| 1 | 0.09 | ND | 0.09 | 74.94 | 0.06 | 32.9 | 0.06 | 38.31 |
| 2 | 0.33 | ND | 0.3 | 71.03 | 0.24 | 49.08 | 0.24 | 72.53 |
| 3 | 0.81 | ND | 0.72 | 70.58 | 0.68 | 56.12 | 0.6 | 95.41 |
| 4 | 1.45 | ND | 1.31 | 75.26 | 1.29 | 60 | 1.36 | 121.95 |
| 5 | 1.96 | ND | 1.86 | 84.81 | 1.84 | 66.55 | 1.86 | 138.01 |
| 6 | 2.24 | 5.87 | 2.17 | 96.31 | 2.19 | 68.94 | 2.16 | 161.65 |

[a]Cultures grown under non-inducing conditions in 50 mM NaCl.
[b]Mean Fluorescence Intensity.
[c]Not Determined.

Construction and Testing of CVD 910-3A.

Figure 3:
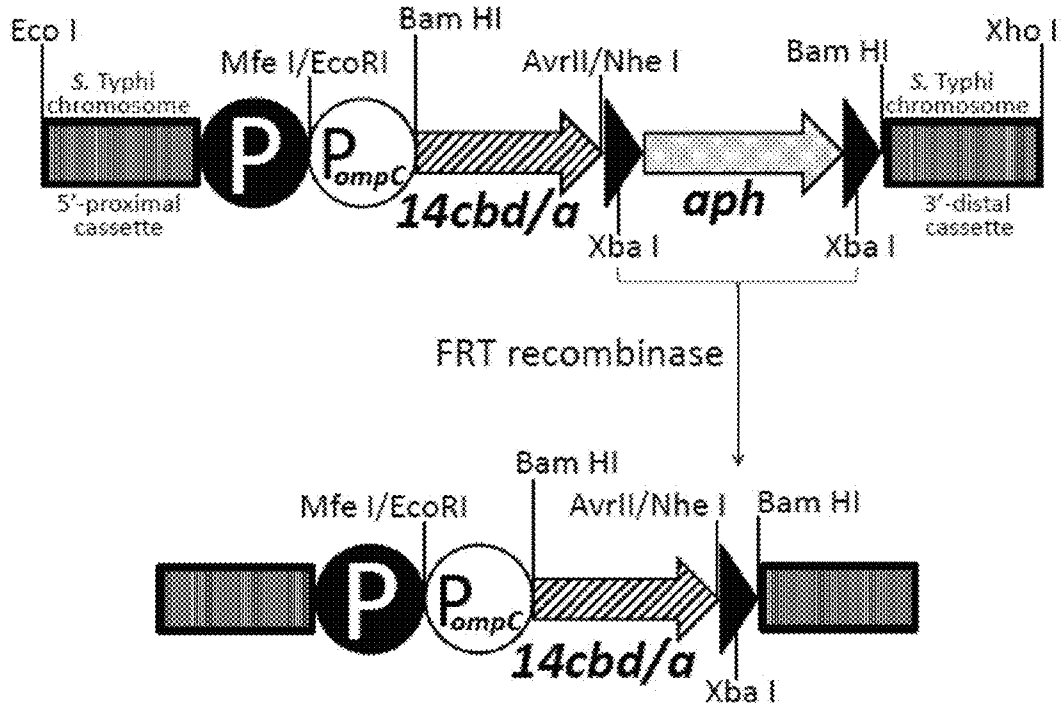
FIG. 3. Schematic depiction of the strategy for chromosomal integration of the cell binding domain from toxin A of *C. difficile*. A synthetic codon-optimized gene cassette encoding the cell binding domain from toxin A designated 14cbd/a was prepared where the osmotically regulated $P_{ompC}$ promoter was genetically fused to a promoterless 14cbd/a gene (tandem white circle and hatched thick arrow) and linked to an aph marker encoding resistance to kanamycin (shaded thick arrow), flanked by FRT recombination sites (black triangles). The incoming $P_{ompC}$-14cbd/a-aph cassette was integrated into the live vector chromosome using the λ Red recombination system, followed by removal of the aph marker using FLP recombinase, to yield the final live vector strain bearing no genes encoding resistance to antibiotics. The bacterial chromosome is represented by 5'-proximal and 3'-terminal darkened rectangles, and the black circle labeled with a "P" represents the wild-type chromosomally-encoded promoter of the deleted target open reading frame (e.g., guaBA, htrA or rpoS).

An additional strain of CVD 910 was prepared that expresses the cell binding domains from toxin A (CBD/A) or from toxin B (CBD/B) of *C. difficile*. A synthetic codon-optimized gene cassette encoding the cell binding domain from toxin A designated 14cbd/a was prepared where the osmotically regulated $P_{ompC}$ promoter was genetically fused to a promoterless 14cbd/a gene. All $P_{ompC}$-controlled antigen cassettes encoding *C. difficile* antigens were constructed by inserting synthetic codon-optimized genes (encoding the cell binding domains of either 14CBD/A (SEQ ID NO:23) or CBD/B (SEQ ID NO:24)) as NheI-AvrII fragments into pSEC10 digested either with SpeI-NheI to generate the unfused $P_{ompC}$-14cbd/a encoding 14CBD/A, or pSEC10 cleaved only with NheI to generate the fused $P_{ompC}$-clyA::cbd/b encoding ClyA-CBD/B. In the case of $P_{ompC}$-14cbd/a, the resulting cassette was then excised from pSEC10 as an EcoRI-AvrII fragment and inserted into chromosomal integration cassettes in preparation for crossing into the chromosome using previously published λ Red integration technologies (see FIG. 3) [3,16]. All integration cassettes were integrated such that only the open reading frame of either guaBA or htrA was replaced, but the original promoters for both chromosomal loci were preserved, as depicted schematically in the chromosomal integration strategy of FIG. 3. For example, integration of $P_{ompC}$-14cbd/a into the guaBA locus resulted in transcription of 14CBD/A controlled both by osmolarity (via $P_{ompC}$) and growth rate (via $P_{guaBA}$). Similarly, integration of the same cassette into htrA resulted in synthesis of 14CBD/A antigen controlled both by osmolarity ($P_{ompC}$) and heat shock/environmental stress ($P_{hfrA}$). [18]

In addition, advantage was taken of the fact that all strains derived from Ty2 are naturally inactivated at the rpoS locus [24] in order to integrate a third copy of $P_{ompC}$-14cbd/a into the chromosome of CVD 910 without further attenuation of the live vector vaccine. Integration of $P_{ompC}$-14cbd/a into rpoS resulted in expression of 14CBD/A antigen controlled by osmolarity ($P_{ompC}$) and entry of growing vaccine organisms into stationary phase ($P_{rpoS}$) [25]. Additional primers used to construct the rpoS-targeted integration cassettes are listed below in Table 4.

TABLE 4

Primers used in the construction and testing of live vector strains expressing chromosomally encoded 14CBD/A from the rpoS locus.

| Primer (SEQ ID NO:) | Sequence[a] |
|---|---|
| 5rpoS-for SEQ ID NO: 25 | 5'- AAGCTTGAATTCCGTATTCTGAGGGCTCAGGTGAACAAAGTGC -3' |
| 5rpoS-rev SEQ ID NO: 26 | 5'- CCTAGGCAATTGACCCGTGATCCCTTGACGGAACTAGCAAGTC -3' |
| 3rpoS-for SEQ ID NO: 27 | 5'- GGATCCGGTTCGGTATCGCGCCAGGTATACAGACAATGC -3' |
| 3rpoS-rev SEQ ID NO: 28 | 5'- CTCGAGCCGGAAGTGCAGGCGGTAAACGCTATGTACAC -3' |
| rpoS PCR-for SEQ ID NO: 29 | 5'- ATGCAGCACAGCAAGGAGTTGTGACCA -3' |
| rpoS PCR-rev SEQ ID NO: 30 | 5'- GGTGCGTATCGATAAGGTCTCTTACCACAGC -3' |

[a]Relevant restriction sites are underlined.

Successful integration of $P_{ompC}$-14cbd/a into guaBA, htrA, and rpoS, creating the live vector strain CVD 910-3A, was verified by direct chromosomal sequencing and listed here as SEQ ID NO:31, SEQ ID NO:32, and SEQ ID NO:33; the protein amino acid sequence for 14CBD/A is listed as SEQ ID NO:34. In all chromosomal sequences presented, the location of the $P_{ompC}$ promoter region, sequences encoding 14CBD/A, and residual FRT chromosomal scar sequences (left behind after removal of the kanamycin resistance marker) shown in Table 5. The location of key restriction sites (BamHI: GGATCC and XbaI: TCTAGA) are also shown in the Table as points of reference to be related back to the chromosomal integration strategy shown in FIG. 3.

TABLE 5

| | $P_{ompC}$ promoter region | Antigen coding region | residual FRT chromosomal scar sequences | BamHI: GGATCC site | XbaI: TCTAGA site | NheI: GCTAGC site |
|---|---|---|---|---|---|---|
| SEQ ID NO: 23 | | 10-984 14CBD/A | | 991-996 | | 13-18 |
| SEQ ID NO: 24 | | 10-1617 CBD/B | | 1624-1629 | | 13-18 |
| SEQ ID NO: 31 | 876-1361 | 1388-2362 14CBD/A | 2437-2470 | 1362-1367; 2486-2491 | 2152-2157 | |
| SEQ ID NO: 32 | 830-1315 | 1342-2316 14CBD/A | 2391-2424 | 1316-1321; 2440-2445 | 2406-2411 | |
| SEQ ID NO: 33 | 655-1140 | 1167-2141 14CBD/A | 2231-2264 | 1141-1146; 2280-2285 | 2246-2251 | |
| SEQ ID NO: 34 | | 1-325 14CBD/A | | | | |
| SEQ ID NO: 35 | | 1431-3029 14CBD/A | 699-732 | | 714-719 | |
| SEQ ID NO: 36 | 1-489 | 1431-3029 14CBD/A | 516-1430 | 490-495; 3084-3089 | | 1425-1430 |
| SEQ ID NO: 37 | | 306-838 14CBD/A | 1-305 | | | |

Figure 4:
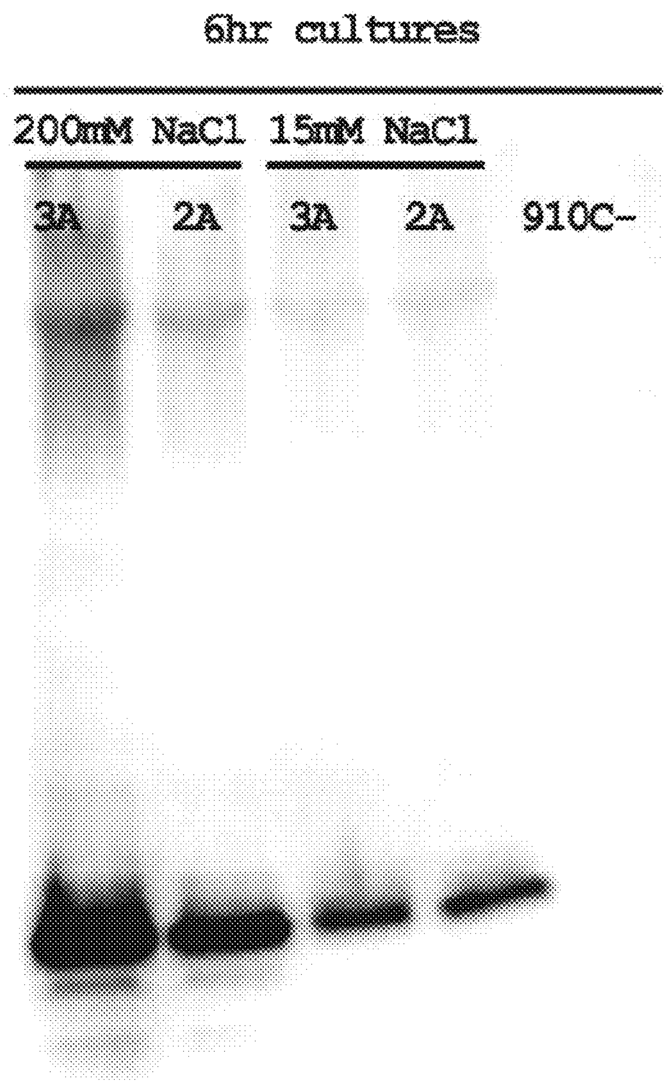
FIG. 4. Western immunoblot analysis. Six hour liquid broth cultures of CVD 910-2A ("2A") were compared to cultures of CVD 910-3A ("3A") under either inducing (200 mM NaCl to activate $P_{ompC}$) or non-inducing (15 mM NaCl) conditions.

Copy number-dependent osmotically controlled expression of 14CBD/A was confirmed by western immunoblot analysis. As shown in FIG. 4, six hour liquid broth cultures of CVD 910-2A (carrying $P_{ompC}$-14cbd/a integrated into guaBA and htrA) were compared to cultures of CVD 910-3A (carrying $P_{ompC}$-14cbd/a integrated into guaBA, htrA, and rpoS). All cultures were grown at 37° C. under either inducing (200 mM NaCl to activate $P_{ompC}$) or non-inducing (15 mM NaCl) conditions. Induction of 14CBD/A synthesis is clearly observed, with maximum expression confirmed for CVD 910-3A induced with high osmolarity.

Construction of CVD 910-3Assb(pSEC10-CBD/B).

Figure 5:
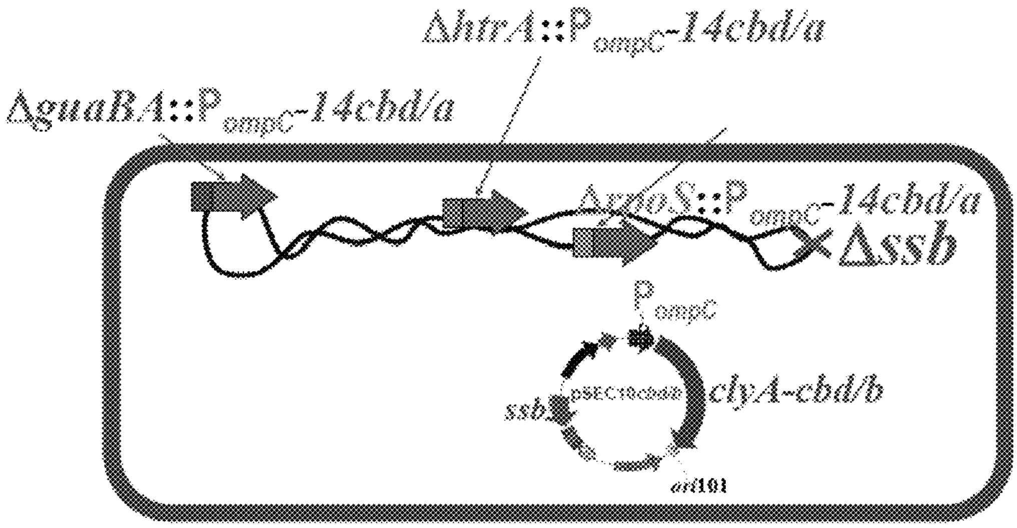
FIG. 5. Schematical depiction of live vaccine strain CVD 910-3Assb(pSEC10-CBD/B).

A chromosomal deletion of ssb was introduced into CVD 910-3A as previously described [3], accompanied by introduction of the non-antibiotic SSB-stabilized expression plasmid pSEC10 into which a synthetic codon-optimized gene cassette encoding the cell binding domain of *C. difficile* toxin B was inserted. The resulting live vaccine strain, designated CVD 910-3Assb(pSEC10-CBD/B) is depicted schematically in FIG. 5. Confirmation of the chromosomal deletion of ssb as intended was confirmed by direct chromosomal sequencing as listed in SEQ ID NO:35; the integrity of the plasmid-based $P_{ompC}$-clyA-cbd/b cassette was also confirmed by direct sequencing as listed in SEQ ID NO:36, with the predicted amino acid sequence of ClyA-CBD/B listed in SEQ ID NO:37. Here again, for SEQ ID NO:35, the location of the residual FRT chromosomal scar sequences (replacing the deleted ssb gene) is shown in Table 5 along with the location of the internal XbaI site (TCTAGA). For the SEQ ID NO:36 sequence encoding ClyA-CBD/B, the location of the $P_{ompC}$ promoter region is also shown in Table 5 along with the locations of the sequence encoding CBD/B and the key restriction sites (BamHI: GGATCC, NheI: GCTAGC, and AvrII: CCTAGG).

Proof-of-Principle Immunogenicity and Challenge Experiment Using a CVD 910 Bivalent Plague Vaccine.

The strategy for development of CVD 910-3Assb (pSEC10-CBD/B) was informed by a critical proof-of-principle experiment in which a bivalent live vector vaccine against pulmonary plague caused by *Yersinia pestis* was constructed and tested. Using the identical genetic engineering strategy used to create CVD 910-3Assb(pSEC10-CBD/B), a bivalent CVD 910-based plague vaccine was constructed that expressed the full-length LcrV antigen (required for secretion of virulence effectors proteins and a virulence factor by itself) from the three independent guaBA, htrA, and rpoS chromosomal sites, each containing an osmotically-regulated $P_{ompC}$-lcrV cassette. The protective anti-phagocytic capsular F1 antigen was expressed from the SSB-stabilized non-antibiotic low copy expression plasmid pSEC10, creating the plasmid pSL445. The F1 antigen of pSL445 was encoded by the natural *Y. pestis* caf1 operon but engineered to be transcriptionally controlled by the in vivo-inducible sifA promoter (an *S. Typhi* promoter controlled by the *Salmonella* Pathogenicity Island 2 (SPI 2) regulon), after having determined that expression of caf1 using the $P_{ompC}$ promoter was toxic to CVD 910. For comparison, the bivalent plasmid pSL483 (again derived from pSEC10) was also constructed in which the expression of both the caf1 operon and lcrV were divergently transcribed from the $P_{sifA}$ and $P_{ompC}$ promoters respectively. SL483 was then introduced into CVD 908-htrAssb creating a bivalent plague candidate vaccine CVD 908-htrAssb (pSL483) in which foreign antigen expression was completely plasmid encoded, to be compared to CVD 910-3Lssb (pSL445) in which foreign antigen expression was balanced between the chromosome and a plasmid.

The immunogenicity of these live vector vaccine strains was evaluated using a heterologous prime-boost immunization strategy in which BALB/c mice were primed intranasally with $1\times10^9$ CFU of live vaccine on days 0 and 28, followed by a boost with a small amount (500 nanograms) of purified lcrV adsorbed to alum on day 56. All mice were challenged on day 84 (i.e., 28 days after the last immunization) with 177 LD50s of virulent *Y. pestis* strain CO92. Results are presented in Table 6.

TABLE 6

Immunogenicity of *S. Typhi* live vector candidate plague vaccines expressing LcrV and F1 and further tested for efficacy in a lethal pulmonary challenge model.

| Vaccine | Day 28 (before boost 1) | Day 42 | Day 56 (before boost 2) | Day 84 (4 weeks post boost 2) | Percent survival (14 days post challenge) |
|---|---|---|---|---|---|
| F1-specific serum IgG | | | | | |
| CVD 910 | 12.5 | 12.5 | 12.5 | 12.5 | 40% |
| CVD 910-3L | 212.5 | 12.5 | 12.5 | 12.5 | 70% |
| CVD 910-3Lssb(pSL445) | 2,268.3 | 33,810.9 | 16,613.2 | 21,778.3 | 100% |
| CVD 908-htrAssb(pSL483) | 445.2 | 11,056.1 | 1,706.5 | 3,684.7 | 100% |
| PBS prime-LcrV boost | 12.5 | 12.5 | 12.5 | 12.5 | 20% |
| PBS | 12.5 | 12.5 | 12.5 | 12.5 | 0% |
| LcrV-specific serum IgG | | | | | |
| CVD 910 | 49.4 | 125.0 | 12.5 | 78,994.1 | |
| CVD 910FL | 93.9 | 224.6 | 12.5 | 86,968.7 | |
| CVD 910-3Lssb(pSL445) | 25.0 | 75.4 | 12.5 | 228,230.1 | |
| CVD 908-htrAssb(pSL483) | 25.0 | 20,008.9 | 21,267.3 | 407,085.8 | |
| PBS prime-LcrV boost | 25.0 | 51.3 | 12.5 | 28,855.7 | |
| PBS | 25.0 | 25.0 | 12.5 | 12.5 | |
| *Typhi* LPS-specific serum IgG | | | | | |
| CVD 910 | 168.5 | 3,570.8 | Pending | 30,192.9 | |
| CVD 910-3L | 311.8 | 7,088.0 | 18,754.0 | 52,266.0 | |
| CVD 910-3Lssb(pSL445) | 171.5 | 1,366.9 | Pending | 18,917.4 | |
| CVD 908-htrAssb(pSL483) | 135.3 | 1,248.5 | Pending | 1,968.6 | |
| PBS prime-LcrV boost | 157.8 | 121.3 | 307.0 | 244.2 | |
| PBS | 150.9 | 116.5 | 297.6 | 188.7 | |

These results clearly show that when expression of foreign antigens is balanced between inducible multilocus chromosomal expression and inducible plasmid-based expression, serum antibody responses against both foreign antigens LcrV and F1 were equivalent to that observed when both antigens were expressed from a single stabilized expression plasmid. Perhaps more importantly, when examining live vector-specific LPS responses, serum IgG responses 10 fold higher were observed in mice immunized with CVD 910-3Lssb(pSL445) versus responses in mice immunized with CVD 908-htrAssb(pSL483) (day 84 GMT=18,917.4 versus 1,968.6 respectively). These results strongly support the hypothesis that the metabolic burden associated with expression of multiple foreign antigens in attenuated multivalent live vector vaccines can be reduced or even eliminated by engineering appropriately balanced levels of antigen expression, accomplished by strategic distribution of foreign genes between multiple chromosomal loci and genetically stabilized low copy plasmids.

Construction of a Multivalent CVD 910 Live Vector Vaccine Targeting Enterotoxins and a Putative Colonization Factor of *C. difficile*.

Enterotoxins A (TcdA) and B (TcdB) are the primary virulence factors of *C. difficile*. However, epidemic strains of *C. difficile* invariably carry an additional toxin affecting the actin cytoskeleton of intestinal cells called *C. difficile* transferase (Cdt); this toxin has also been called binary toxin (BT) because it is composed of a catalytic A subunit and a cell-binding B subunit (30, 31). The activity of BT causes rearrangement of the actin cytoskeleton of intestinal epithelial cells, disrupting tight junctions and potentially allowing better penetration of enterotoxins into gastrointestinal tissue (32), thereby enhancing the virulence of epidemic strains. It was recently discovered that BT also appears to enhance colonization of the intestinal tract by inducing microtubule-based protrusions which enhance the adherence of *C. difficile* (33). Based on available data, it was hypothesized that binary toxin acts to enhance the virulence of epidemic strains carrying all three toxins by promoting better colonization of *C. difficile* and possibly improving the penetration and binding of enterotoxins A and B. Recent animal studies suggest that immunization against enterotoxins alone does not prevent colonization of the gastrointestinal tract by *C. difficile* (34), and that strains producing only binary toxin are able to colonize susceptible animals (35). Therefore, live vector-mediated mucosal immunity against *C. difficile* disease will be targeted at three levels: 1] by blocking the binding of both enterotoxins through targeting of serum immunity to their cell-binding domains, 2] by inducing mucosal immunity to the cell binding domain of BT (designated here as CBD-BT) to reduce penetration of toxins A and B by maintaining the integrity of intestinal epithelial tissue, and 3] by targeting mucosal immunity against CBD-BT to reduce intestinal colonization, recurrent infection, and environmental transmission in a clinical setting.

Towards this goal of constructing a trivalent live vaccine against *C. difficile* infections in which mucosal immunity is targeted against enterotoxins A, B, and binary toxin, CVD 910-3A was first modified to express CBD/A from one further chromosomal locus, namely the clyA locus. This modification serves to avoid loss of expression of chromosomally encoded 14CBD/A from the three chromosomal loci of CVD 910-3A. Integration of $P_{ompC}$-14cbd/a into the clyA locus was completed using the method described above in the paragraph entitled "Construction and testing of CVD 910-3A"; this integration cassette was integrated such that only the open reading frame encoded by clyA was replaced, while preserving the original clyA promoter, as depicted schematically in the chromosomal integration strategy of FIG. 3.

The resulting monovalent vaccine strain, CVD 910-4A, was then further modified to contain and express CBD-BT fused to the carboxyl terminus of ClyA in the manner routinely used in low copy number SSB-stabilized expression plasmids; as with other expression cassettes constructed in these plasmids and later moved into chromosomal integration modules, this clyA::cbd-bt gene fusion was again transcriptionally controlled by the osmotically regulated promoter $P_{ompC}$. In order to take advantage of the previously constructed integration modules in which incoming expression cassettes encoding foreign antigens were inserted as EcoRI-AvrII fragments, it was necessary to create a new synthetic gene encoding ClyA in which the internal naturally occurring EcoRI site was removed; the resulting synthetic gene (designated clyA*) was then re-inserted into pSEC10 to create pSEC10S2 (SEQ ID NO:45). In addition to the EcoRI site (base 1034, T to C), other commonly used restriction sites in pSEC10S2 (SEQ ID NO:45) were removed, including BglII (base 590, T to C), two HindIII sites (base 686, A to G; base 1043, A to G), HpaI (base 978, T to C; base 980, A to G) and MfeI (base 1262, A to G).

A synthetic 2655 bp codon-optimized gene encoding the 878 residues of CBD-BT (SEQ ID NO:46) was then synthesized as a NheI-AwII fragment (SEQ ID NO:47). However, insertion of this cassette into pSEC10S2 cleaved with NheI was unsuccessful. A smaller gene cassette encoding residues 212-878 of CBD-BT (designated B2; SEQ ID NO:46) was amplified using the forward primer 5'-AG-ATCTaaaataaggaggaaaaaaaaATG<u>GCTAGC</u>CTGATGT CTGATTGGGAAGATGAAG-3' (NheI site underlined; SEQ ID NO:51) and the reverse primer 5-AAGCTT <u>CCTAGG</u>TTATTAATCCACACTCAGAACCAGCAG TTCG-3' (AvrII site underlined; SEQ ID NO:52); this decision was based on a report by Sundriyal et al. (36) demonstrating the biological activity of this truncated portion of CBD-BT which results naturally from proteolytic cleavage of the full-length 98.8 kDa CBD-BT, removing a 20 kDa N-terminal fragment, and resulting in a soluble 74.9 kDa protein. The resulting 2054 bp synthetic gene (SEQ ID NO:48) was then successfully inserted as a NheI-AvrII fragment into pSEC10S2 cleaved with NheI to create pSEC10S2-B2 encoding a 972 residue 108.6 kDa ClyA-CBD-BT fusion protein (SEQ ID NO:49). This plasmid was then introduced into CVD 910-4A to create the bivalent vaccine CVD 910-4Assb(pSEC10S2-B2).

Figure 6:
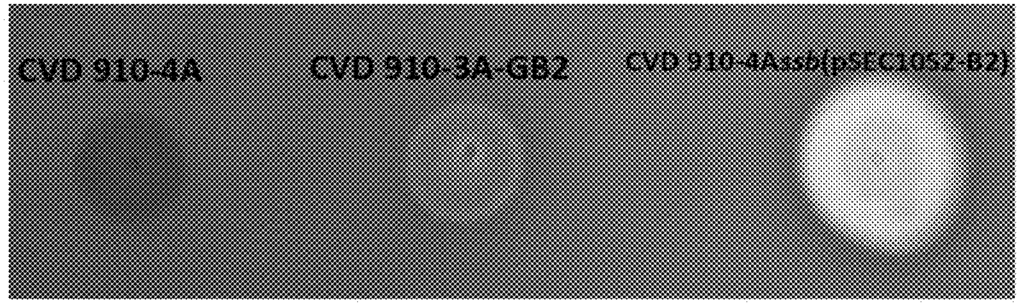
FIG. 6. Comparison of hemolytic activity of fusion proteins expressed in CVD 910-4A, CVD 910-3A-GB2 and CVD 910-4Assb(pSEC10S2-B2). The noted strains were grown on trypticase soy agar with 5% sheep red blood cells under conditions of incubation at 37° C. for 24 hours. The plates were then photographed without magnification.

The $P_{ompC}$-clyA*-b2 expression cassette was then excised from pSEC10S2-B2 as a 3491 bp EcoRI-AvrII fragment (SEQ ID NO:50), inserted into the guaBA integration module cleaved with MfeI-NheI, and then integrated into the guaBA locus of CVD 910-4A, replacing the previously integrated $P_{ompC}$-14cbd/a cassette to create the bivalent live vaccine CVD 910-3A-GB2 in which 14CBD/A is chromosomally expressed from the htrA, rpoS, and clyA loci, and CBD-BT is expressed from the guaBA locus. When export of the protein fusion was compared for hemolytic activity with plasmid-encoded fusion protein expressed in CVD 910-4Assb(pSEC10S2-B2), proper export of the fusion protein was observed in both strains, although plasmid-encoded export was much higher due to copy number (FIG. 6).

Figure 7:
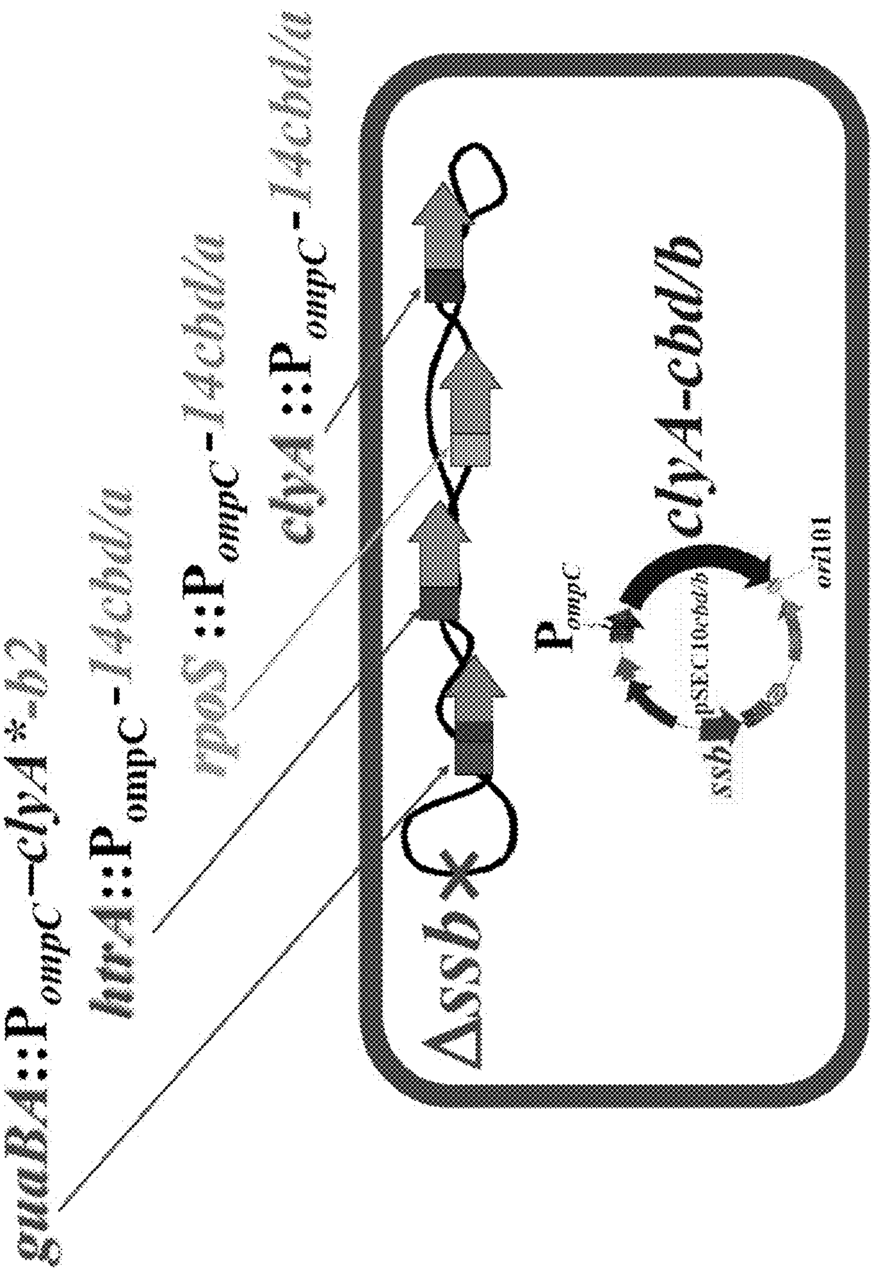
FIG. 7. Schematical depiction of live vaccine strain CVD 910-3A-GB2ssb (pSEC10-CBD/B) which contains insertions into the guaBA, htrA, rpoS and clyA loci and carries the plasmid pSEC10-CBD/B.

The SSB-stabilized plasmid encoding the cell binding domain of enterotoxin B, pSEC10-CBD/B, is introduced into CVD 910-3A-GB2 to create the trivalent live vaccine CVD 910-3A-GB2ssb(pSEC10-CBD/B) shown in FIG. 7 in which 14CBD/A is chromosomally expressed from the htrA, rpoS, and clyA loci, CBD-B2 is expressed from the guaBA locus, and CBD/B is expressed from pSEC10-CBD/B.

Alternatively, the SSB-stabilized plasmid encoding the cell binding domain of enterotoxin B, pSEC10-CBD/B, is introduced into CVD 910-2A-GRB2 to create the trivalent live vaccine CVD 910-2A-GRB2ssb(pSEC10-CBD/B) in which 14CBD/A is chromosomally expressed from the htrA and clyA loci, CBD-B2 is expressed from the guaBA locus and rpoS locus, and CBD/B is expressed from pSEC10-CBD/B.

To improve binary toxin-specific toxin neutralizing activity, a second copy of $P_{ompC}$-clyA*-b2 can be inserted into the rpoS locus of CVD 910-3A-GB2ssb(pSEC10-CBD/B).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Wang S, Li Y, Shi H, Sun W, Roland K L, Curtiss R, III. Comparison of a regulated delayed antigen synthesis system with in vivo-inducible promoters for antigen delivery by live attenuated *Salmonella* vaccines. Infect Immun 2011; 79:937-949.
2. Galen J E, Levine M M. Can a 'flawless' live vector vaccine strain be engineered? Trends in Microbiology 2001; 9:372-376.
3. Galen J E, Wang J Y, Chinchilla M, Vindurampulle C, Vogel J E, Levy H, et al. A new generation of stable, nonantibiotic, low-copy-number plasmids improves immune responses to foreign antigens in *Salmonella enterica* serovar *Typhi* live vectors. Infect Immun 2010; 78:337-347.
4. Cranenburgh R M, Lewis K S, Hanak J A. Effect of plasmid copy number and lac operator sequence on antibiotic-free plasmid selection by operator-repressor titration in *Escherichia coli*. J Mol Microbiol Biotechnol 2004; 7:197-203.
5. Nakayama K, Kelley S M, Curtiss III R. Construction of an Asd+ expression-cloning vector: stable maintenance and high level expression of cloned genes in a *Salmonella* vaccine strain. Bio/Technology 1988; 6:693-697.
6. Galen J E, Zhao L, Chinchilla M, Wang J Y, Pasetti M F, Green J, et al. Adaptation of the endogenous *Salmonella enterica* serovar *Typhi* clyA-encoded hemolysin for antigen export enhances the immunogenicity of anthrax protective antigen domain 4 expressed by the attenuated live-vector vaccine strain CVD 908-htrA. Infect Immun 2004; 72:7096-7106.
7. Galen J E, Chinchilla M, Pasetti M F, Wang J Y, Zhao L, rciniega-Martinez I, et al. Mucosal immunization with attenuated *Salmonella enterica* serovar *Typhi* expressing protective antigen of anthrax toxin (PA83) primes monkeys for accelerated serum antibody responses to parenteral PA83 vaccine. J Infect Dis 2009; 199:326-335.
8. Gentschev I, Dietrich G, Goebel W. The *E. coli* alpha-hemolysin secretion system and its use in vaccine development. Trends Microbiol 2002; 10:39-45.
9. Kang H Y, Curtiss R, III. Immune responses dependent on antigen location in recombinant attenuated *Salmonella typhimurium* vaccines following oral immunization. FEMS Immunol Med Microbiol 2003; 37:99-104.
10. Smith M A, Bidochka M J. Bacterial fitness and plasmid loss: the importance of culture conditions and plasmid size. Can J Microbiol 1998; 44:351-355.
11. Gonzalez C, Hone D M, Noriega F, Tacket C O, Davis J R, Losonsky G, et al. *Salmonella typhi* vaccine strain CVD 908 expressing the circumsporozoite protein of *Plasmodium falciparum*: strain construction and safety and immunogenicity in humans. J Infect Dis 1994; 169: 927-931.
12. Hohmann E L, Oletta C A, Loomis W P, Miller S I. Macrophage-inducible expression of a model antigen in *Salmonella typhimurium* enhances immunogenicity. Proc Natl Acad Sci USA 1995; 92:2904-2908.
13. Tacket C O, Sztein M, Wasserman S S, Losonsky G, Kotloff K, Wyant T L, et al. Phase 2 clinical trial of attenuated *Salmonella enterica* serovar *Typhi* oral live vector vaccine CVD 908-htrA in U.S. volunteers. Infect Immun 2000; 68:1196-1201.
14. Wang J Y, Pasetti M F, Noriega F, Anderson R J, Wasserman S S, Galen J E, et al. Construction, genotypic and phenotypic characterization, and immunogenicity of attenuated ΔguaBA *Salmonella enterica* serovar *Typhi* strain CVD 915. Infect Immun 2001; 69:4734-4741.
15. Husnain S I, Thomas M S. The U P element is necessary but not sufficient for growth rate-dependent control of the *Escherichia coli* guaB promoter. J Bacteriol 2008; 190: 2450-2457.
16. Datsenko K A, Wanner B L. One-step inactivation of chromosomal genes in *Escherichia coli* K-12 using PCR products. Proc Natl Acad Sci USA 2000; 97:6640-6645.
17. Tacket C O, Hone D M, Curtiss III R, Kelly S M, Losonsky G, Guers L, et al. Comparison of the safety and immunogenicity of ΔaroCΔaroD and ΔcyaΔcrp *Salmonella typhi* strains in adult volunteers. Infect Immun 1992; 60:536-541.
18. Lewis C, Skovierova H, Rowley G, Rezuchova B, Homerova D, Stevenson A, et al. *Salmonella enterica* serovar *Typhimurium* HtrA: regulation of expression and role of the chaperone and protease activities during infection. Microbiology 2009; 155:873-881.
19. Fuentes J A, Jofre M R, Villagra N A, Mora G C. RpoS- and Crp-dependent transcriptional control of *Salmonella Typhi* taiA and hlyE genes: role of environmental conditions. Res Microbiol 2009; 160:800-808.
20. Galen J E, Pasetti M F, Tennant S M, Olvera-Ruiz P, Sztein M B, Levine M M. *Salmonella enterica* serovar *Typhi* Live Vector Vaccines Finally Come of Age. Immunol Cell Biol 2009; 87:400-412.
21. Xu X, Husseiny M I, Goldwich A, Hensel M. Efficacy of intracellular activated promoters for generation of *Salmonella*-based vaccines. Infect Immun 2010; 78:4828-4838.
22. Everest P, Frankel G, Li J, Lund P, Chatfield S, Dougan G. Expression of LacZ from the htrA, nirB, and groE promoters in a *Salmonella* vaccine strain: influence of growth in mammalian cells. FEMS Microbiol Lett 1995; 126:97-102.
23. Galen J E, Nair J, Wang J Y, Wasserman S S, Tanner M K, Sztein M, et al. Optimization of plasmid maintenance in the attenuated live vector vaccine strain *Salmonella typhi* CVD 908-htrA. Infect Immun 1999; 67:6424-6433.
24. Robbe-Saule V, Norel F. The rpoS mutant allele of *Salmonella typhi* Ty2 is identical to that of the live typhoid vaccine Ty21a. FEMS Microbiol Lett 1999 Jan. 1; 170(1):141-3.
25. Hirsch M, Elliott T. Fis regulates transcriptional induction of RpoS in *Salmonella enterica*. J Bacteriol 2005 March; 187(5):1568-80.
26. Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.
27. Oscarsson, J., Y. Mizunoe, L. Li, X. Lai, A. Wieslander, and B. E. Uhlin. 1999. Molecular analysis of the cytolytic protein ClyA (SheA) from *Escherichia coli*. Mol. Microbiol. 32:1226-1238.
28. Galen et al. Immunol. Cell Biol. May 5, 2009, pp 1-13.
29. Metcalf et al. Conditionally replicative and conjugative plasmids carrying lacZ alpha for cloning, mutagenesis, and allele replacement in bacteria. 1996. 35(1): 1-13.
30. Perelle S, Gibert M, Bourlioux P, Corthier G, Popoff M R. 1997. Production of a complete binary toxin (actin-specific ADP-ribosyltransferase) by *Clostridium difficile* CD196. Infect. Immun. 65:1402-1407.

31. Rupnik M, Grabnar M, Geric B. 2003. Binary toxin producing *Clostridium difficile* strains. Anaerobe. 9:289-294.

32. Carter G P, Rood J I, Lyras D. 2010. The role of toxin A and toxin B in *Clostridium difficile*-associated disease. Gut Microbes 1:58-64.

33. Schwan C, Stecher B, Tzivelekidis T, van H M, Rohde M, Hardt W D, Wehland J, Aktories K. 2009. *Clostridium difficile* toxin CDT induces formation of microtubule-based protrusions and increases adherence of bacteria. PLoS. Pathog. 5:e1000626.

34. Siddiqui F, O'Connor J R, Nagaro K, Cheknis A, Sambol S P, Vedantam G, Gerding D N, Johnson S. 2012. Vaccination with parenteral toxoid B protects hamsters against lethal challenge with toxin A-negative, toxin B-positive *Clostridium difficile* but does not prevent colonization. J. Infect. Dis. 205:128-133.

35. Geric B, Carman R J, Rupnik M, Genheimer C W, Sambol S P, Lyerly D M, Gerding D N, Johnson S. 2006. Binary toxin-producing, large clostridial toxin-negative *Clostridium difficile* strains are enterotoxic but do not cause disease in hamsters. J. Infect. Dis. 193:1143-1150.

36. Sundriyal A, Roberts A K, Ling R, McGlashan J, Shone C C, Acharya K R. 2010. Expression, purification and cell cytotoxicity of actin-modifying binary toxin from *Clostridium difficile*. Protein Expr. Purif. 74:42-48.

What is claimed is:

1. An attenuated strain of *Salmonella enterica* serovar *Typhi* ("*S. Typhi*") having chromosomal disruptions in the guaBA locus, the htrA locus, the rpoS locus, and the ssb locus.

2. The attenuated strain of claim 1, wherein the attenuated strain further comprises a chromosomal-based expression system integrated into at least one location of chromosomal disruption, wherein each chromosomal-based expression system comprises an expression cassette encoding an antigen.

3. The attenuated strain of claim 2, wherein the attenuated strain comprises at least two chromosomal-based expression systems.

4. The attenuated strain of claim 3, wherein the attenuated strain comprises two different chromosomal-based expression systems.

5. The attenuated strain of claim 2, wherein the attenuated strain comprises at least three chromosomal-based expression systems.

6. The attenuated strain of claim 5, wherein the attenuated strain comprises three different chromosomal-based expression systems.

7. The attenuated strain of claim 2, wherein the attenuated strain comprises at least four chromosomal-based expression systems.

8. The attenuated strain of claim 7, wherein the attenuated strain comprises four different chromosomal-based expression systems.

9. The attenuated strain of claim 2, wherein the attenuated strain further comprises one or more plasmid-based expression systems, and wherein each plasmid-based expression system comprises an expression cassette encoding an antigen.

10. The attenuated strain of claim 9, wherein the plasmid-based expression system is an SSB-stabilized plasmid-based expression system.

11. The attenuated strain of claim 2 formulated as a pharmaceutical composition comprising a pharmaceutically-acceptable carrier or diluent.

12. The attenuated strain of claim 9 formulated as a pharmaceutical composition comprising a pharmaceutically-acceptable carrier or diluent.

13. The attenuated strain of claim 1, wherein the attenuated strain further comprises (i) a chromosomal-based expression system integrated into at least one location of chromosomal disruption, wherein each chromosomal-based expression system comprises an expression cassette encoding an antigen; and (ii) one or more plasmid-based expression systems, wherein each plasmid-based expression system comprises an expression cassette encoding an antigen.

14. The attenuated strain of claim 13 formulated as a pharmaceutical composition comprising a pharmaceutically-acceptable carrier or diluent.

* * * * *

SEQUENCE LISTING

```
<160> NUMBER OF SEQ ID NOS: 52

<210> SEQ ID NO 1
<211> LENGTH: 29
<212> TYPE: DNA
<213> ORGANISM: Artificial Sequence
<220> FEATURE:
<223> OTHER INFORMATION: Primer 5guaBA-for

<400> SEQUENCE: 1

gaattctagc tgctcatact tctgctgca                                   29


<210> SEQ ID NO 2
<211> LENGTH: 30
<212> TYPE: DNA
<213> ORGANISM: Artificial Sequence
<220> FEATURE:
<223> OTHER INFORMATION: Primer 5guaBA-rev

<400> SEQUENCE: 2

gctagccaat tggggcaata tctcacctgg                                  30


<210> SEQ ID NO 3
<211> LENGTH: 32
<212> TYPE: DNA
<213> ORGANISM: Artificial Sequence
<220> FEATURE:
<223> OTHER INFORMATION: Primer 3guaBA-for

<400> SEQUENCE: 3

ggatccacta gtgtcgataa cccttcctgt gt                               32


<210> SEQ ID NO 4
<211> LENGTH: 29
<212> TYPE: DNA
<213> ORGANISM: Artificial Sequence
<220> FEATURE:
<223> OTHER INFORMATION: Primer 3guaBA-rev

<400> SEQUENCE: 4

ctcgagacag cacctacaag tctggcatg                                   29


<210> SEQ ID NO 5
<211> LENGTH: 24
<212> TYPE: DNA
<213> ORGANISM: Artificial Sequence
<220> FEATURE:
<223> OTHER INFORMATION: Primer guaBA PCR-for

<400> SEQUENCE: 5

gcgctgacca ccggaatacg gctg                                        24
```

<210> SEQ ID NO 6
<211> LENGTH: 28
<212> TYPE: DNA
<213> ORGANISM: Artificial Sequence
<220> FEATURE:
<223> OTHER INFORMATION: Primer guaBA PCR-rev

<400> SEQUENCE: 6
catggcatgg atgaggcaac cgcgaagc 28

<210> SEQ ID NO 7
<211> LENGTH: 36
<212> TYPE: DNA
<213> ORGANISM: Artificial Sequence
<220> FEATURE:
<223> OTHER INFORMATION: Primer 5htrA-for

<400> SEQUENCE: 7
gaattcgtac cttcaatcag gcgttactgg aagatg 36

<210> SEQ ID NO 8
<211> LENGTH: 49
<212> TYPE: DNA
<213> ORGANISM: Artificial Sequence
<220> FEATURE:
<223> OTHER INFORMATION: Primer 5htrA-rev

<400> SEQUENCE: 8
gctagccaat tgcgattaac aggtaacgca aaattgctgt gtacgtcag 49

<210> SEQ ID NO 9
<211> LENGTH: 44
<212> TYPE: DNA
<213> ORGANISM: Artificial Sequence
<220> FEATURE:
<223> OTHER INFORMATION: Primer 3htrA-for

<400> SEQUENCE: 9
ggatccacta gtctgcgtaa gattctcgac agcaagccgt cggt 44

<210> SEQ ID NO 10
<211> LENGTH: 42
<212> TYPE: DNA
<213> ORGANISM: Artificial Sequence
<220> FEATURE:
<223> OTHER INFORMATION: Primer 3htrA-rev

<400> SEQUENCE: 10
ctcgagccag catcatttcg gcagtcatac acaccagttc gc 42

<210> SEQ ID NO 11
<211> LENGTH: 29
<212> TYPE: DNA
<213> ORGANISM: Artificial Sequence
<220> FEATURE:
<223> OTHER INFORMATION: Primer htrA PCR-for

<400> SEQUENCE: 11
gtgtcgccga tcttgaagac gcggtagag 29

<210> SEQ ID NO 12
<211> LENGTH: 29
<212> TYPE: DNA
<213> ORGANISM: Artificial Sequence
<220> FEATURE:
<223> OTHER INFORMATION: Primer htrA PCR-rev -continued

<400> SEQUENCE: 12
ctatcgacgc caagctggcc gctgtcgac 29

<210> SEQ ID NO 13
<211> LENGTH: 51
<212> TYPE: DNA
<213> ORGANISM: Artificial Sequence
<220> FEATURE:
<223> OTHER INFORMATION: Primer 5clyA-for

<400> SEQUENCE: 13
tagtaatgag aattcgctgg tattgatcgg ctctccggta gagattagcg a 51

<210> SEQ ID NO 14
<211> LENGTH: 49
<212> TYPE: DNA
<213> ORGANISM: Artificial Sequence
<220> FEATURE:
<223> OTHER INFORMATION: Primer 5clyA-rev

<400> SEQUENCE: 14
gctagccaat tgtgcctctt taaatatata aattgcaatt aagtacctg 49

<210> SEQ ID NO 15
<211> LENGTH: 56
<212> TYPE: DNA
<213> ORGANISM: Artificial Sequence
<220> FEATURE:
<223> OTHER INFORMATION: Primer 3clyA-for

<400> SEQUENCE: 15
ggatccacta gtgatacatt ttcattcgat ctgtgtactt ttaacgcccg atagcg 56

<210> SEQ ID NO 16
<211> LENGTH: 57
<212> TYPE: DNA
<213> ORGANISM: Artificial Sequence
<220> FEATURE:
<223> OTHER INFORMATION: Primer 3clyA-rev

<400> SEQUENCE: 16
tgatagtaac tcgagacaat ccataagaaa ggtcaggcac actgggaagg cgacatc 57

<210> SEQ ID NO 17
<211> LENGTH: 27
<212> TYPE: DNA
<213> ORGANISM: Artificial Sequence
<220> FEATURE:
<223> OTHER INFORMATION: Primer clyA PCR-for

<400> SEQUENCE: 17
catgatggta tccagtatgg cacaagc 27

<210> SEQ ID NO 18
<211> LENGTH: 27
<212> TYPE: DNA
<213> ORGANISM: Artificial Sequence
<220> FEATURE:
<223> OTHER INFORMATION: Primer clyA PCR-rev

<400> SEQUENCE: 18
gtaatcgaca acatgctaca tccatcg 27

<210> SEQ ID NO 19

<211> LENGTH: 33
<212> TYPE: DNA
<213> ORGANISM: Artificial Sequence
<220> FEATURE:
<223> OTHER INFORMATION: Primer 5FRT-aph-for

<400> SEQUENCE: 19
gaattcgcta gcgctggagc tgcttcgaag ttc 33

<210> SEQ ID NO 20
<211> LENGTH: 33
<212> TYPE: DNA
<213> ORGANISM: Artificial Sequence
<220> FEATURE:
<223> OTHER INFORMATION: Primer 3FRT-aph-rev

<400> SEQUENCE: 20
ctcgagttcc ggggatccgt cgacctgcag ttc 33

<210> SEQ ID NO 21
<211> LENGTH: 32
<212> TYPE: DNA
<213> ORGANISM: Artificial Sequence
<220> FEATURE:
<223> OTHER INFORMATION: Primer 5gfpuv

<400> SEQUENCE: 21
caattgtgtg gtagcacaga ataatgaaaa gt 32

<210> SEQ ID NO 22
<211> LENGTH: 30
<212> TYPE: DNA
<213> ORGANISM: Artificial Sequence
<220> FEATURE:
<223> OTHER INFORMATION: Primer 3gfpuv

<400> SEQUENCE: 22
gctagctcat tatttgtaga gctcatccat 30

<210> SEQ ID NO 23
<211> LENGTH: 996
<212> TYPE: DNA
<213> ORGANISM: Artificial Sequence
<220> FEATURE:
<223> OTHER INFORMATION: codon-optimized gene cassette tcdA-14CBD/A

<400> SEQUENCE: 23
tagtaatgaa tggctagcac cggctatacg agcatcaacg ggaagcattt ttatttcaat 60
accgacggca ttatgcagat cggggtgttc aaagggccca acggtttcga atactttgcg 120
ccggccaaca cggatgcgaa taacatcgaa ggtcaagcca tcctctacca gaacaaattc 180
ctgaccctca atggcaagaa atattacttc gggtccgaca gcaaggctgt cacgggtctg 240
cgcacgattg atgggaaaaa gtattacttc aacaccaata ctgccgtggc ggtcaccgga 300
tggcaaacga tcaacggcaa gaaatactac ttcaatacca acacgtccat tgcctcgacc 360
gggtatacga tcatttccgg caaacacttc tacttcaaca ccgacgggat catgcaaatc 420
ggtgtgttta aagggcccga tggcttcgag tactttgccc cggcgaatac ggacgccaat 480
aacattgaag gtcaggcaat tcggtatcag aatcgttttc tctatctgca tgacaacatc 540
tactatttcg gtaataacag caaggcggcc accgggtggg tcacgattga tggcaaccgg 600
tattacttcg agcccaatac ggcgatgggg gcgaatggtt ataaaacgat cgacaacaag 660
aatttctact ttcgcaacgg gctcccgcag attggcgtgt tcaaagggtc caacggcttt 720
gagtacttcg cccccgcgaa tacggatgcc aacaatatcg agggccaagc gattcggtat 780
caaaaccgct tcctccacct gctcgggaaa atctattact tcggcaataa ctcgaaagcc 840
gtcacgggtt ggcaaacgat taatggcaaa gtgtattact tcatgccgga tactgcaatg 900
gcagccgctg gtggattatt cgaaattgac ggcgtcatct atttctttgg cgtggatggg 960
gtcaaagccc cggggatcta tggctaatga cctagg 996

<210> SEQ ID NO 24
<211> LENGTH: 1629
<212> TYPE: DNA
<213> ORGANISM: Artificial Sequence
<220> FEATURE:
<223> OTHER INFORMATION: codon-optimized gene cassette TcdB CBD/B

<400> SEQUENCE: 24
tagtaatgaa tggctagcgg cctgatctat attaacgatt cactgtacta tttcaagccg 60
cccgtcaata acctcatcac cgggtttgtg acggtcggcg acgataaata ctacttcaat 120
ccgatcaacg gcggagccgc gagcattggg gagaccatca ttgatgacaa gaattattac 180
ttcaaccaga gtggcgtgct gcagacgggg gtcttcagta ccgaggacgg ctttaaatac 240
ttcgcccccg cgaatacgct cgatgagaac ctggaagggg aggcgattga ctttaccggc 300
aagctgatca ttgacgagaa catctactat ttcgatgaca attaccgcgg ggccgtggaa 360
tggaaggagc tcgatggcga gatgcactat tttagcccgg agacggggaa agctttcaaa 420
ggcctgaatc aaattgggga ctacaagtat tacttcaact ctgacggtgt gatgcagaag 480
gggttcgtga gtatcaatga caacaagcat tatttcgacg attctggcgt catgaaagtg 540
gggtacaccg agatcgatgg caagcacttc tactttgccg agaatggtga gatgcaaatc 600
ggcgtgttca atacggaaga cggtttaag tatttcgcgc atcataacga ggatctcggc 660
aatgaagagg gcgaagagat ctcatattcc ggaatcctca acttcaataa caagatttac 720
tactttgatg actcatttac cgccgtggtc ggctggaagg acctcgagga tgggtcaaag 780
tactatttcg acgaggatac ggcggaggcc tacatcggcc tgtcattaat caacgacggc 840
cagtattact ttaatgatga cggcatcatg caggtcgggt ttgtcaccat caacgataaa 900
gtcttctact tctctgactc tggcattatc gagagcgggg tgcagaacat cgacgataac 960
tatttctaca tcgatgacaa tggcattgtc cagatcggcg tgttcgatac gtcagacggt 1020
tataagtatt ttgcgcccgc caacaccgtc aacgataata tctacggtca agctgttgaa 1080
tatagtggtt tggtccgtgt cggtgaagac gtgtactatt tcggcgagac gtacacaatt 1140
gagacgggct ggatctatga tatggagaac gagagtgaca agtactattt caatcctgag 1200
accaagaaag catgcaaggg gatcaacctg atcgatgaca tcaagtacta tttcgacgag 1260
aagggcatta tgcgcacggg gcttatctca tttgagaata acaattatta cttcaatgag 1320
aacggggaaa tgcagtttgg gtacatcaat attgaggaca agatgttcta ttttggcgag 1380
gatggcgtca tgcagatcgg ggtgttcaac accccagatg gtttcaagta tttcgcgcat 1440
cagaatacgc tggatgagaa cttcgagggc gaatcaatca actataccgg gtggctggac 1500
ctcgatgaga agcgctacta tttcacggac gaatacattg cggccaccgg ctcagtcatc 1560
attgatggcg aggaatacta tttcgaccct gatacggcgc agctggtgat cagtgagtaa 1620
tgacctagg 1629

<210> SEQ ID NO 25

-continued

<211> LENGTH: 43
<212> TYPE: DNA
<213> ORGANISM: Artificial Sequence
<220> FEATURE:
<223> OTHER INFORMATION: Primer 5rpoS-for

<400> SEQUENCE: 25
aagcttgaat tccgtattct gagggctcag gtgaacaaag tgc 43

<210> SEQ ID NO 26
<211> LENGTH: 43
<212> TYPE: DNA
<213> ORGANISM: Artificial Sequence
<220> FEATURE:
<223> OTHER INFORMATION: Primer 5rpoS-rev

<400> SEQUENCE: 26
cctaggcaat tgacccgtga tcccttgacg gaactagcaa gtc 43

<210> SEQ ID NO 27
<211> LENGTH: 39
<212> TYPE: DNA
<213> ORGANISM: Artificial Sequence
<220> FEATURE:
<223> OTHER INFORMATION: Primer 3rpoS-for

<400> SEQUENCE: 27
ggatccggtt cggtatcgcg ccaggtatac agacaatgc 39

<210> SEQ ID NO 28
<211> LENGTH: 38
<212> TYPE: DNA
<213> ORGANISM: Artificial Sequence
<220> FEATURE:
<223> OTHER INFORMATION: Primer 3rpoS-rev

<400> SEQUENCE: 28
ctcgagccgg aagtgcaggc ggtaaacgct atgtacac 38

<210> SEQ ID NO 29
<211> LENGTH: 27
<212> TYPE: DNA
<213> ORGANISM: Artificial Sequence
<220> FEATURE:
<223> OTHER INFORMATION: Primer rpoS PCR-for

<400> SEQUENCE: 29
atgcagcaca gcaaggagtt gtgacca 27

<210> SEQ ID NO 30
<211> LENGTH: 31
<212> TYPE: DNA
<213> ORGANISM: Artificial Sequence
<220> FEATURE:
<223> OTHER INFORMATION: Primer rpoS PCR-rev

<400> SEQUENCE: 30
ggtgcgtatc gataaggtct cttaccacag c 31

<210> SEQ ID NO 31
<211> LENGTH: 3290
<212> TYPE: DNA
<213> ORGANISM: Artificial Sequence
<220> FEATURE:
<223> OTHER INFORMATION: 5guaB-PompC-14CBDA-FRT-3guaA gene cassette

<400> SEQUENCE: 31

-continued

```
gcgctgacca ccggaatacg gctggcaaaa atagcccgcg ccacgcgttc gtcgttaaaa     60
ctccacaaat cttccagcga accgccgccg cgtccgacga tcagcacgtc gcactcgccg    120
cgcgtgtttg ccagttcgat agcacgaacg atctgccccg gcgcatcgtc gccctgtacc    180
gcggttggat agataataac gggcagggat gggtcacgac gcttcaacac gtggaggata    240
tcgtgcagcg ccgcgccggt tttcgaggtg atcaccccaa cgcagtgggc cggggagggc    300
aacggctgtt tatgctgctg atcgaacaag ccttcggcat ggagtttggc ttttagctgc    360
tcatacttct gctgcaacaa gccttcgcca gccggctgca tactttcggc gatgatttga    420
taatcgccgc gcggctcgta cagcgtaatg ttggcgcgta ccagcacctg ctgcccgtgc    480
tgcgggcgga acgtcacccg gcggttgctg ttgcggaaca tcgcacagcg cacctgagcg    540
gtatcgtctt tgagcgtaaa gtaccagtgg cccgacgcag gctgcgtgaa attagaaatc    600
tcgccgctga tccatacctg tcccatctcc tgttctaaca gcagacgaac cgtctggtta    660
aggcggctta cggtaaaaat tgaggaagtt tgagaggata acatgtgagc gggatcaaat    720
tctaaatcag caggttattc aatcgatagt aacctgctca cgggggatcg caagcactat    780
ttgcaaaaaa atgtagatgc aaccgattac gttctgtata atgccgcggc aatatttatt    840
aacctcccag gtgagatatt gccccaattc gtcaattctg tggtagcaca gaataatgaa    900
aagtgtgtaa agaagggtaa aaaaaaccga atgcgaggca tccggttgaa atagggggtaa   960
acagacattc agaaatgaat gacggtaata aataaagtta atgatgatag cgggagttat   1020
tctagttgcg agtgaaggtt ttgttttgac attcagtgct gtcaaatact taagaataag   1080
ttattgattt taaccttgaa ttattattgc ttgatgttag gtgcttattt cgccattccg   1140
caataatctt aaaaagttcc cttgcattta cattttgaaa catctatagc gataaatgaa   1200
acatcttaaa agttttagta tcatattcgt gttggattat tctgcatttt tggggagaat   1260
ggacttgccg actgattaat gagggttaat cagtatgcag tggcataaaa aagcaaataa   1320
aggcatataa cagatcgatc ttaaacatcc acaggaggat gggatccaaa ataaggagga   1380
aaaaaaaatg actagcaccg gctatacgag catcaacggg aagcattttt atttcaatac   1440
cgacggcatt atgcagatcg ggggtgttcaa agggcccaac ggtttcgaat actttgcgcc   1500
ggccaacacg gatgcgaata acatcgaagg tcaagccatc ctctaccaga acaaattcct   1560
gaccctcaat ggcaagaaat attacttcgg gtccgacagc aaggctgtca cgggtctgcg   1620
cacgattgat gggaaaaagt attacttcaa caccaatact gccgtggcgg tcaccggatg   1680
gcaaacgatc aacggcaaga aatactactt caataccaac acgtccattg cctcgaccgg   1740
gtatacgatc atttccggca aacacttcta cttcaacacc gacgggatca tgcaaatcgg   1800
tgtgtttaaa gggcccgatg gcttcgagta ctttgccccg gcgaatacgg acgccaataa   1860
cattgaaggt caggcaattc ggtatcagaa tcgttttctc tatctgcatg acaacatcta   1920
ctatttcggt aataacagca aggcggccac cgggtgggtc acgattgatg gcaaccggta   1980
ttacttcgag cccaatacgg cgatgggggc gaatggttat aaaacgatcg acaacaagaa   2040
tttctacttt cgcaacgggc tcccgcagat tggcgtgttc aaagggtcca acggctttga   2100
gtacttcgcc cccgcgaata cggatgccaa caatatcgag ggccaagcga ttcggtatca   2160
aaaccgcttc ctccacctgc tcgggaaaat ctattacttc ggcaataact cgaaagccgt   2220
cacgggttgg caaacgatta atggcaaagt gtattacttc atgccggata ctgcaatggc   2280
agccgctggt ggattattcg aaattgacgg cgtcatctat ttctttggcg tggatggggt   2340
```

-continued caaagccccg gggatctatg gctaatgacc tagctgataa cctagcccgc ctaatgagcg 2400
ggcttttttt tctcggccta gcgctggagc tgcttcgaag ttcctatact ttctagagaa 2460
taggaacttc gaactgcagg tcgacggatc cactagtgtc gataaccctt cctgtgtttt 2520
catgaacagg taaaagtgaa tttaaccctc tgtttttgca gagggttttt atttatgtgc 2580
atagatgcat tttctgtgta gtgcacagct tctggcggca aagcactgca tcgacacaat 2640
agtgggtttc actggcagca cacaatcaaa tctgacagtc ggcttcgagc gaggtgcgga 2700
cattggtagc ttcaacaaca tgactggcat tgaggtgtat taatcaacgg gaagcaggtc 2760
agtttactcc gccagcccga cttttacgaa agggctacca tgactacgcg attttttgat 2820
tagcttgcca acgtataatc ctctgatttc tggtgatgcg attcgtccaa caaattctga 2880
acggttggtt tcgggggggg gatgaccaat tcccgggtaa agtattgctg agagcctgcc 2940
ttcaaccagc actgtatctc gtaaacttcc atcaccaaac cgccgtaggt ggcgtatgca 3000
aattgtaggt tttcatcttt tggtactttt gcccagacgc cacgcgtagc ttcatataat 3060
gcaagtgcac tcatgccaga cttgtaggtg ctgtttagca aaaaagcgag cccggcatgt 3120
tcaggtgcga tttccgtctc ttgcttaaga agaagatgat tgagctcatc cagcgtgatt 3180
cgccccataa gggagctgct tcctcgtact ttgttggtca gttctccaac acccaagaga 3240
tcaatacatg ttgcttcaac aagcttcgcg gttgcctcat ccatgccatg 3290

<210> SEQ ID NO 32
<211> LENGTH: 3229
<212> TYPE: DNA
<213> ORGANISM: Artificial Sequence
<220> FEATURE:
<223> OTHER INFORMATION: 5htrA-PompC-14CBDA-FRT-3htrA gene cassette

<400> SEQUENCE: 32
gtgtcgccga tcttgaagac gcggtagaga aaagaatctt tagcgttgag cagctttatc 60
accatttata tcacgcgtgg ggccaccatg agaaggattc gctgtttgag ctggtggtag 120
gaaatgcgtg ggaaaaatca cgcgccaata cattaagccg cagtaccgaa gatcagtttt 180
ttatgtattt acgggtaaat acattaaata aactggtgcc ctatgccgct cagcgtttta 240
ttgataattt gccgcagatt tttgccggta ccttcaatca ggcgttactg gaagatgcca 300
gcggttttag ccgcctgctt gaactctata agaatgtggc ggttgaacat gtgtttagcc 360
atccggatgt agaacagctt gaactacagg gataccgggt gatcagcggg ttattagata 420
tctatcagcc gctattaagc ttgtcgctta acgactttcg cgagctggtg gaaaaagaac 480
ggttgaaacg cttccctata gaatcgcgct tatttcagaa actttctacg cgccatcgtt 540
tggcctacgt ggaagtcgtc agtaaattac ccacggattc ggcggagtac ccggtactgg 600
aatattatta tcgctgtcgg ttgattcagg attatatcag cgggatgact gacctttacg 660
catgggatga atatcggcgt ttgatggcgg tcgaacagta aatggacttt tgtaaagatg 720
gacaataaat ttttactttt tccagaaact ttattccgga acttcgcgtt ataaaatgaa 780
tctgacgtac acagcaattt tgcgttacct gttaatcgca attcgtcaat tctgtggtag 840
cacagaataa tgaaaagtgt gtaaagaagg gtaaaaaaaa ccgaatgcga ggcatccggt 900
tgaaataggg gtaaacagac attcagaaat gaatgacggt aataaataaa gttaatgatg 960
atagcgggag ttattctagt tgcgagtgaa ggttttgttt tgacattcag tgctgtcaaa 1020
tacttaagaa taagttattg attttaacct tgaattatta ttgcttgatg ttaggtgctt 1080
atttcgccat tccgcaataa tcttaaaaag ttcccttgca tttacatttt gaaacatcta 1140

-continued

```
tagcgataaa tgaaacatct taaaagtttt agtatcatat tcgtgttgga ttattctgca   1200
tttttgggga gaatggactt gccgactgat taatgagggt taatcagtat gcagtggcat   1260
aaaaaagcaa ataaaggcat ataacagatc gatcttaaac atccacagga ggatgggatc   1320
caaaataagg aggaaaaaaa aatgactagc accggctata cgagcatcaa cgggaagcat   1380
ttttatttca ataccgacgg cattatgcag atcggggtgt tcaaagggcc caacggtttc   1440
gaatactttg cgccggccaa cacggatgcg aataacatcg aaggtcaagc catcctctac   1500
cagaacaaat tcctgaccct caatggcaag aaatattact tcgggtccga cagcaaggct   1560
gtcacgggtc tgcgcacgat tgatgggaaa aagtattact tcaacaccaa tactgccgtg   1620
gcggtcaccg gatggcaaac gatcaacggc aagaaatact acttcaatac caacacgtcc   1680
attgcctcga ccgggtatac gatcatttcc ggcaaacact tctacttcaa caccgacggg   1740
atcatgcaaa tcggtgtgtt taaagggccc gatggcttcg agtactttgc cccggcgaat   1800
acggacgcca ataacattga aggtcaggca attcggtatc agaatcgttt tctctatctg   1860
catgacaaca tctactattt cggtaataac agcaaggcgg ccaccgggtg ggtcacgatt   1920
gatggcaacc ggtattactt cgagcccaat acggcgatgg gggcgaatgg ttataaaacg   1980
atcgacaaca agaatttcta ctttcgcaac gggctcccgc agattggcgt gttcaaaggg   2040
tccaacggct ttgagtactt cgcccccgcg aatacggatg ccaacaatat cgagggccaa   2100
gcgattcggt atcaaaaccg cttcctccac ctgctcggga aaatctatta cttcggcaat   2160
aactcgaaag ccgtcacggg ttggcaaacg attaatggca aagtgtatta cttcatgccg   2220
gatactgcaa tggcagccgc tggtggatta ttcgaaattg acggcgtcat ctatttcttt   2280
ggcgtggatg ggtcaaagc  cccggggatc tatggctaat gacctagctg ataacctagc   2340
ccgcctaatg agcgggcttt tttttctcgg cctagcgctg gagctgcttc gaagttccta   2400
tactttctag agaataggaa cttcgaactg caggtcgacg gatccactag tctgcgtaag   2460
attctcgaca gcaagccgtc ggtgctggcg ctgaatattc agcgtggtga tagttctatt   2520
tatttgctga tgcagtaatc acctttgtcc cccttccacc acggaagggg gcaacacttt   2580
tctgtgaaac tccccacaac tccatacttc tttgcaccgt tttgtgcatt tgcacaatgt   2640
cgaggcctgt catcttcctt atgcttgtgc tctgctcaca ggagggattt atggctggct   2700
ggcatcttga taccaaaatg gcgcaggata tcgtggcgcg cactatgcgc atcatcgata   2760
ccaatatcaa cgtaatggat gcccgcgggc gtattatcgg cagcggcgat cgggaacgta   2820
ttggtgaatt gcacgaaggc gcgttgttag tgctgtcaca gggccgggtt gtggatatcg   2880
acaacgccgt ggcgcgacac ctgcacgggg tgcgtcaggg gattaatctt cccttacgcc   2940
ttgagggcga aattgttggc gtgatcggtc tcaccggcga accagagcat ctgcgtaaat   3000
atggcgaact ggtgtgtatg actgccgaaa tgatgctgga acagtcgcgg ttaatgcacc   3060
ttttggcgca ggatagccgt ttgcgtgaag agctggtgat gaacctgatt caggccgaag   3120
aaaatacgcc ggcgctggtg gaatgggcac agcgtttagg gatcgatttg aaccagccgc   3180
gtgtggcggc ggtggtggaa gtcgacagcg gccagcttgg cgtcgatag               3229
```

<210> SEQ ID NO 33
<211> LENGTH: 2982
<212> TYPE: DNA
<213> ORGANISM: Artificial Sequence
<220> FEATURE:
<223> OTHER INFORMATION: 5rpoS-PompC-14CBDA-FRT-3rpoS gene cassette -continued

<400> SEQUENCE: 33
atgcagcaca gcaaggagtt gtgaccaggt ctgcacaaaa ttccaccgtt gcagttgcgt 60
ctcaaccaac aattacgtat tctgagggct caggtgaaca aagtgctaac aaaatgttgc 120
caaacaacaa gcctgctggg acggttgtca cagcgcctgt aacggcacca acggtaagca 180
cgaccgaacc aaatgcaagc agtacgtcaa ccagcgcgcc gatttccgca tggcgctggc 240
cgacggatgg caaagtgatc gaaaactttg gcgcttccga agggggcaat aaagggatcg 300
acattgcagg cagtaaggga caggctatcg tcgcaaccgc tgatgggcgc gtcgtatatg 360
ccggtaacgc actgcgtggt tacggtaatc ttattatcat caaacataac gatgattacc 420
tgagtgccta cgcccataat gatacgatgc tggtccggga acaacaggaa gttaaggcgg 480
ggcaaaaaat cgctactatg ggtagcaccg gcaccagctc tacacgcttg cattttgaaa 540
ttcgttacaa ggggaaatcc gtaaacccgc tgcgttattt accgcagcga taaagcggcg 600
gaaccaggct ttgacttgct agttccgtca agggatcacg ggtcaattcg tcaattctgt 660
ggtagcacag aataatgaaa agtgtgtaaa gaagggtaaa aaaaaccgaa tgcgaggcat 720
ccggttgaaa taggggtaaa cagacattca gaaatgaatg acggtaataa ataaagttaa 780
tgatgatagc gggagttatt ctagttgcga gtgaaggttt tgttttgaca ttcagtgctg 840
tcaaatactt aagaataagt tattgatttt aaccttgaat tattattgct tgatgttagg 900
tgcttatttc gccattccgc aataatctta aaaagttccc ttgcatttac attttgaaac 960
atctatagcg ataaatgaaa catcttaaaa gttttagtat catattcgtg ttggattatt 1020
ctgcattttt ggggagaatg gacttgccga ctgattaatg agggttaatc agtatgcagt 1080
ggcataaaaa agcaaataaa ggcatataac agatcgatct taaacatcca caggaggatg 1140
ggatccaaaa taaggaggaa aaaaaaatga ctagcaccgg ctatacgagc atcaacggga 1200
agcattttta tttcaatacc gacggcatta tgcagatcgg ggtgttcaaa gggcccaacg 1260
gtttcgaata ctttgcgccg gccaacacgg atgcgaataa catcgaaggt caagccatcc 1320
tctaccagaa caaattcctg accctcaatg gcaagaaata ttacttcggg tccgacagca 1380
aggctgtcac gggtctgcgc acgattgatg ggaaaaagta ttacttcaac accaatactg 1440
ccgtggcggt caccggatgg caaacgatca acggcaagaa atactacttc aataccaaca 1500
cgtccattgc ctcgaccggg tatacgatca tttccggcaa acacttctac ttcaacaccg 1560
acgggatcat gcaaatcggt gtgtttaaag ggcccgatgg cttcgagtac tttgccccgg 1620
cgaatacgga cgccaataac attgaaggtc aggcaattcg gtatcagaat cgttttctct 1680
atctgcatga caacatctac tatttcggta ataacagcaa ggcggccacc gggtgggtca 1740
cgattgatgg caaccggtat tacttcgagc ccaatacggc gatgggggcg aatggttata 1800
aaacgatcga caacaagaat ttctactttc gcaacgggct cccgcagatt ggcgtgttca 1860
aagggtccaa cggctttgag tacttcgccc ccgcgaatac ggatgccaac aatatcgagg 1920
gccaagcgat tcggtatcaa aaccgcttcc tccacctgct cgggaaaatc tattacttcg 1980
gcaataactc gaaagccgtc acgggttggc aaacgattaa tggcaaagtg tattacttca 2040
tgccggatac tgcaatggca gccgctggtg gattattcga aattgacggc gtcatctatt 2100
tctttggcgt ggatggggtc aaagccccgg ggatctatgg ctaatgacct agctgataac 2160
ctagcccgcc taatgagcgg gcttttttt ctcggcctag cgacgaattg cctagcgctg 2220
gagctgcttc gaagttccta tactttctag agaataggaa cttcgaactg caggtcgacg 2280
gatccggttc ggtatcgcgc caggtataca gacaatgctg acactgatat accgtccaga 2340

-continued ctccttttac cggcgaagtc gccatgagtt caatatgtgc atcggcacag cgtggacaaa 2400
tcatcggtta ctccttattt acggttggcc agcatggcgg tcagcttttc agcccaggct 2460
ttagtttccg gtaaatccac aaccggctgg ctatagtgac cacggttatc tggcgcaacc 2520
ggcgtggtag cgtcaatgat cagtttgtcg gtaatccccg ccgggcttga acccgggtcc 2580
agttccagga cggacatatt cggtagctgt accagatcgc ctgccggatt cactttcgac 2640
gacaacgccc acatcacctg tggcagatta aatggatcga catcttcatc aaccatgatc 2700
accatcttca catatcccag accgtgcggc gtcgtcatcg cgcgcaggcc caccgcacgg 2760
gcaaagccgc cgtagcgttt tttggtcgag atgatggcca gcaagccgtg ggtgtacata 2820
gcgtttaccg cctgcacttc cggaaattcg gctttcagct gttgatacag tggcacacag 2880
gtcgccggcc ccatcaggta gtcgatttcc gtccacggca tccccaaata gagcgattca 2940
aaaatgggtt tgctgtggta agagacctta tcgatacgca cc 2982

<210> SEQ ID NO 34
<211> LENGTH: 325
<212> TYPE: PRT
<213> ORGANISM: Clostridium difficile

<400> SEQUENCE: 34

Met Thr Ser Thr Gly Tyr Thr Ser Ile Asn Gly Lys His Phe Tyr Phe
1 5 10 15

Asn Thr Asp Gly Ile Met Gln Ile Gly Val Phe Lys Gly Pro Asn Gly
20 25 30

Phe Glu Tyr Phe Ala Pro Ala Asn Thr Asp Ala Asn Asn Ile Glu Gly
35 40 45

Gln Ala Ile Leu Tyr Gln Asn Lys Phe Leu Thr Leu Asn Gly Lys Lys
50 55 60

Tyr Tyr Phe Gly Ser Asp Ser Lys Ala Val Thr Gly Leu Arg Thr Ile
65 70 75 80

Asp Gly Lys Lys Tyr Tyr Phe Asn Thr Asn Thr Ala Val Ala Val Thr
85 90 95

Gly Trp Gln Thr Ile Asn Gly Lys Lys Tyr Tyr Phe Asn Thr Asn Thr
100 105 110

Ser Ile Ala Ser Thr Gly Tyr Thr Ile Ile Ser Gly Lys His Phe Tyr
115 120 125

Phe Asn Thr Asp Gly Ile Met Gln Ile Gly Val Phe Lys Gly Pro Asp
130 135 140

Gly Phe Glu Tyr Phe Ala Pro Ala Asn Thr Asp Ala Asn Asn Ile Glu
145 150 155 160

Gly Gln Ala Ile Arg Tyr Gln Asn Arg Phe Leu Tyr Leu His Asp Asn
165 170 175

Ile Tyr Tyr Phe Gly Asn Asn Ser Lys Ala Ala Thr Gly Trp Val Thr
180 185 190

Ile Asp Gly Asn Arg Tyr Tyr Phe Glu Pro Asn Thr Ala Met Gly Ala
195 200 205

Asn Gly Tyr Lys Thr Ile Asp Asn Lys Asn Phe Tyr Phe Arg Asn Gly
210 215 220

Leu Pro Gln Ile Gly Val Phe Lys Gly Ser Asn Gly Phe Glu Tyr Phe
225 230 235 240

Ala Pro Ala Asn Thr Asp Ala Asn Asn Ile Glu Gly Gln Ala Ile Arg
245 250 255

-continued

```
Tyr Gln Asn Arg Phe Leu His Leu Leu Gly Lys Ile Tyr Tyr Phe Gly
            260                 265                 270

Asn Asn Ser Lys Ala Val Thr Gly Trp Gln Thr Ile Asn Gly Lys Val
        275                 280                 285

Tyr Tyr Phe Met Pro Asp Thr Ala Met Ala Ala Ala Gly Gly Leu Phe
    290                 295                 300

Glu Ile Asp Gly Val Ile Tyr Phe Phe Gly Val Asp Gly Val Lys Ala
305                 310                 315                 320

Pro Gly Ile Tyr Gly
                325
```

<210> SEQ ID NO 35
<211> LENGTH: 1542
<212> TYPE: DNA
<213> ORGANISM: Artificial Sequence
<220> FEATURE:
<223> OTHER INFORMATION: ssb region of chromosomal deletion

<400> SEQUENCE: 35

```
ttcggcggat cggagagatc gcagacttcg ccgtcaatac gggcgcgaat gtaaccctgg     60

cttgccagat tttccagcgt tttggtgtgt tcgcctttac gctctttaat aatcggcgcc    120

agcagcatca ggcgtttgcc ttccggctgc gacagcacgt tatcgaccat ctggctaacg    180

gtttgcgccg ccagcggcac gtcatggtcc ggacaacgcg gctcgcccac gcgggcaaac    240

agcaggcgca ggtagtcgtg gatctcggta atagtaccca ccgtagagcg cgggttgtgc    300

gatgtcgatt tctgttcaat tgagatcgcg ggcgatagcc cctcaatatg gtcgacatcc    360

ggtttttcca tgagcgacaa aaactgccgc gcgtaagcgg agagcgattc aacgtaacga    420

cgctgccctt cggcatacag agtgtcgaaa gccagtgagg atttgcctga acccgaaagc    480

ccggtcacga caatcagttt gtcgcggggg atgacgaggt taatattttt gagattatgg    540

gtgcgggcgc cccgaacttc gatcttatcc attcaccttt cccggtagag actcggatgc    600

ctggtttgtt tgaaggacaa acggcagaaa cggctaatta tgacacaatt taacctgttt    660

gaatatacag tagctagcgt gtaggctgga gctgcttcga agttcctata ctttctagag    720

aataggaact tcggaatagg aactaaggag gatattcata tgcattttcg ctatagttct    780

cgtctgctga aatgcctggt gtaaaccagg cattttatta cctggtatta ttgtcttagt    840

atccctttca aaaaagagaa gcgcatatct cacggaatga cttacggaaa aatgtcgctt    900

atcgcctctg gccgactcgc ctcggcacat cattatccag ccgaagttca taaatgtact    960

gcaataaccc ggattgtctt aaatatgaaa gagaaatctc atctgcaaaa tatataattt   1020

atagccattt tttgacaaca aaaagatatt ataaaataac ggtagagaat ggtcggtatt   1080

atcaatagtt aattaaatgc ttgctttagc ttgtgatgag ctcaaatatg atatgtgtat   1140

cttgctttat ttttaattgc tgaagataaa attgttactt atagctggct ttatataaaa   1200

aatggtttta tttgtgtatt tttttacaca attctgattt tttactcccc acttattata   1260

ttttcaatga tttaagttat attgaagtcc ctatgaccct atgttttaat tgtgaaaatt   1320

cattttatcc tctggaggca aatttattaa atacgtatgg ttataacgcg tattaaaaag   1380

aaatatgtcc ttaaaatgat ttagagtttc aatgattagc taacaaatct atttatcggc   1440

gggtggtttt aatttgctga tgactatttt ttatttatga gctgagagct tatgcgatac   1500

ctattattgg ggaagatata gttagtgcaa taattgatgt ct                      1542
```

<210> SEQ ID NO 36

<211> LENGTH: 8045
<212> TYPE: DNA
<213> ORGANISM: Artificial Sequence
<220> FEATURE:
<223> OTHER INFORMATION: PompC-clyA-cbd/b cassette

<400> SEQUENCE: 36
gaattctgtg gtagcacaga ataatgaaaa gtgtgtaaag aagggtaaaa aaaaccgaat 60
gcgaggcatc cggttgaaat aggggtaaac agacattcag aaatgaatga cggtaataaa 120
taaagttaat gatgatagcg ggagttattc tagttgcgag tgaaggtttt gttttgacat 180
tcagtgctgt caaatactta agaataagtt attgatttta accttgaatt attattgctt 240
gatgttaggt gcttatttcg ccattccgca ataatcttaa aaagttccct tgcatttaca 300
ttttgaaaca tctatagcga taaatgaaac atcttaaaag ttttagtatc atattcgtgt 360
tggattattc tgcatttttg gggagaatgg acttgccgac tgattaatga gggttaatca 420
gtatgcagtg gcataaaaaa gcaaataaag gcatataaca gatcgatctt aaacatccac 480
aggaggatgg gatccaaaat aaggaggaaa aaaaaatgac tagtattttt gcagaacaaa 540
ctgtagaggt agttaaaagc gcgatcgaaa ccgcagatgg ggcattagat ctttataaca 600
aatacctcga ccaggtcatc ccctggaaga cctttgatga aaccataaaa gagttaagcc 660
gttttaaaca ggagtactcg caggaagctt ctgttttagt tggtgatatt aaagttttgc 720
ttatggacag ccaggacaag tattttgaag cgacacaaac tgtttatgaa tggtgtggtg 780
tcgtgacgca attactctca gcgtatattt tactatttga tgaatataat gagaaaaaag 840
catcagccca gaaagacatt ctcattagga tattagatga tggtgtcaag aaactgaatg 900
aagcgcaaaa atctctcctg acaagttcac aaagtttcaa caacgcttcc ggaaaactgc 960
tggcattaga tagccagtta actaatgatt tttcggaaaa aagtagttat ttccagtcac 1020
aggtggatag aattcgtaag gaagcttatg ccggtgctgc agccggcata gtcgccggtc 1080
cgtttggatt aattatttcc tattctattg ctgcgggcgt gattgaaggg aaattgattc 1140
cagaattgaa taacaggcta aaaacagtgc aaaatttctt tactagctta tcagctacag 1200
tgaaacaagc gaataaagat atcgatgcgg caaaattgaa attagccact gaaatagcag 1260
caattgggga gataaaaacg gaaaccgaaa caaccagatt ctacgttgat tatgatgatt 1320
taatgctttc tttattaaaa ggagctgcaa agaaaatgat taacacctgt aatgaatacc 1380
aacaacgtca tggtaagaag acgcttttcg aggttcctga cgtcgctagc ggcctgatct 1440
atattaacga ttcactgtac tatttcaagc cgcccgtcaa taacctcatc accgggtttg 1500
tgacggtcgg cgacgataaa tactacttca atccgatcaa cggcggagcc gcgagcattg 1560
gggagaccat cattgatgac aagaattatt acttcaacca gagtggcgtg ctgcagacgg 1620
gggtcttcag taccgaggac ggctttaaat acttcgcccc cgcgaatacg ctcgatgaga 1680
acctggaagg ggaggcgatt gactttaccg gcaagctgat cattgacgag aacatctact 1740
atttcgatga caattaccgc ggggccgtgg aatggaagga gctcgatggc gagatgcact 1800
attttagccc ggagacgggg aaagctttca aaggcctgaa tcaaattggg gactacaagt 1860
attacttcaa ctctgacggt gtgatgcaga aggggttcgt gagtatcaat gacaacaagc 1920
attatttcga cgattctggc gtcatgaaag tggggtacac cgagatcgat ggcaagcact 1980
tctactttgc cgagaatggt gagatgcaaa tcggcgtgtt caatacggaa gacgggttta 2040
agtatttcgc gcatcataac gaggatctcg gcaatgaaga gggcgaagag atctcatatt 2100
ccggaatcct caacttcaat aacaagattt actactttga tgactcattt accgccgtgg 2160

-continued

```
tcggctggaa ggacctcgag gatgggtcaa agtactattt cgacgaggat acggcggagg   2220
cctacatcgg cctgtcatta atcaacgacg gccagtatta ctttaatgat gacggcatca   2280
tgcaggtcgg gtttgtcacc atcaacgata aagtcttcta cttctctgac tctggcatta   2340
tcgagagcgg ggtgcagaac atcgacgata actatttcta catcgatgac aatggcattg   2400
tccagatcgg cgtgttcgat acgtcagacg gttataagta ttttgcgccc gccaacaccg   2460
tcaacgataa tatctacggt caagctgttg aatatagtgg tttggtccgt gtcggtgaag   2520
acgtgtacta tttcggcgag acgtacacaa ttgagacggg ctggatctat gatatggaga   2580
acgagagtga caagtactat ttcaatcctg agaccaagaa agcatgcaag gggatcaacc   2640
tgatcgatga catcaagtac tatttcgacg agaagggcat tatgcgcacg gggcttatct   2700
catttgagaa taacaattat tacttcaatg agaacgggga aatgcagttt gggtacatca   2760
atattgagga caagatgttc tattttggcg aggatggcgt catgcagatc ggggtgttca   2820
acaccccaga tggtttcaag tatttcgcgc atcagaatac gctggatgag aacttcgagg   2880
gcgaatcaat caactatacc gggtggctgg acctcgatga gaagcgctac tatttcacgg   2940
acgaatacat tgcggccacc ggctcagtca tcattgatgg cgaggaatac tatttcgacc   3000
ctgatacggc gcagctggtg atcagtgagt aatgacctag ctgataacct agcccgccta   3060
atgagcgggc tttttttct cggcctaggt ttcacctgtt ctattaggtg ttacatgctg    3120
ttcatctgtt acattgtcga tctgttcatg gtgaacagct ttaaatgcac caaaaactcg   3180
taaaagctct gatgtatcta tctttttac accgttttca tctgtgcata tggacagttt    3240
tccctttgat atctaacggt gaacagttgt tctacttttg tttgttagtc ttgatgcttc   3300
actgatagat acaagagcca taagaacctc agatccttcc gtatttagcc agtatgttct   3360
ctagtgtggt tcgttgtttt tgcgtgagcc atgagaacga accattgaga tcatgcttac   3420
tttgcatgtc actcaaaaat tttgcctcaa aactggtgag ctgaattttt gcagttaaag   3480
catcgtgtag tgtttttctt agtccgttac gtaggtagga atctgatgta atggttgttg   3540
gtattttgtc accattcatt tttatctggt tgttctcaag ttcggttacg agatccattt   3600
gtctatctag ttcaacttgg aaaatcaacg tatcagtcgg gcggcctcgc ttatcaacca   3660
ccaatttcat attgctgtaa gtgtttaaat ctttacttat tggtttcaaa acccattggt   3720
taagcctttt aaactcatgg tagttatttt caagcattaa catgaactta aattcatcaa   3780
ggctaatctc tatatttgcc ttgtgagttt tcttttgtgt tagttctttt aataaccact   3840
cataaatcct catagagtat ttgttttcaa aagacttaac atgttccaga ttatatttta   3900
tgaatttttt taactggaaa agataaggca atatctcttc actaaaaact aattctaatt   3960
tttcgcttga gaacttggca tagtttgtcc actggaaaat ctcaaagcct ttaaccaaag   4020
gattcctgat ttccacagtt ctcgtcatca gctctctggt tgctttagct aatacaccat   4080
aagcattttc cctactgatg ttcatcatct gagcgtattg gttataagtg aacgataccg   4140
tccgttcttt ccttgtaggg ttttcaatcg tggggttgag tagtgccaca cagcataaaa   4200
ttagcttggt ttcatgctcc gttaagtcat agcgactaat cgctagttca tttgctttga   4260
aaacaactaa ttcagacata catctcaatt ggtctaggtg attttaatca ctataccaat   4320
tgagatgggc tagtcaatga taattactag ctagtccttt tcctttgagt tgtgggtatc   4380
tgtaaattct gctagacctt tgctggaaaa cttgtaaatt ctgctagacc ctctgtaaat   4440
tccgctagac ctttgtgtgt tttttttgtt tatattcaag tggttataat ttatagaata   4500
```

```
aagaaagaat aaaaaaagat aaaaagaata gatcccagcc ctgtgtataa ctcactactt   4560
tagtcagttc cgcagtatta caaaaggatg tcgcaaacgc tgtttgctcc tctacaaaac   4620
agaccttaaa accctaaagg cttaagtagc accctcgcaa gctcgggcaa atcgctgaat   4680
attccttttg tctccgacca tcaggcacct gagtcgctgt ctttttcgtg acattcagtt   4740
cgctgcgctc acggctctgg cagtgaatgg gggtaaatgg cactacaggc gccttttatg   4800
gattcatgca aggaaactac ccataataca agaaaagccc gtcacgggct tctcagggcg   4860
ttttatggcg ggtctgctat gtggtgctat ctgacttttt gctgttcagc agttcctgcc   4920
ctctgatttt ccagtctgac cacttcggat tatcccgtga caggtcattc agactggcta   4980
atgcacccag taaggcagcg gtatcatcaa caggcttacc cgtcttactg tcaaccggat   5040
ctaaaacact aggcccaaga gtttgtagaa acgcaaaaag gccatccgtc aggatggcct   5100
tctgcttaat ttgatgcctg gcagtttatg gcgggcgtcc tgcccgccac cctccgggcc   5160
gttgcttcgc aacgttcaaa tccgctcccg gcggatttgt cctactcagg agagcgttca   5220
ccgacaaaca acagataaaa cgaaaggccc agtctttcga ctgagccttt cgttttattt   5280
gatgcctggc agttccctac tctcgcatgg ggagacccca cactaccatc ggcgctacgg   5340
cgtttcactt ctgagttcgg catggggtca ggtgggacca ccgcgctact gccgccaggc   5400
aaattctgtt ttatcagacc gcttctgcgt tctgatttaa tctgtatcag gctgaaaatc   5460
ttctctcatc cgccaaaaca gccaagctgg atctaaaaca ctagctctag ctattgtttt   5520
aatgacaaat cagaacggaa tgtcatcatc aaagtccatc ggcggctcgt tagacggcgc   5580
tgccggagcg gactgctgcg ggcgagactg cgcgccgccg ctgaactgat tgccaccctg   5640
cggctgctga ggctgacccc aaccgccctg cggctgacca ccaccgatat tgccacctgc   5700
cggagcgcca ccaccctgac gaccacccag catctgcatg gtgccgccaa cgttcaccac   5760
gacttctgtg gtgtagcgat cctgaccgga ttgatcggtc catttacggg tacgcagctg   5820
accttcgata taaacctgag aacctttacg cagatattcg ctcgccactt ctgccagttt   5880
gccgaacagc acaacgcggt gccattcagt ctgttctttc atctcgccgg tcgctttatc   5940
acgccaggat tcggaagtag ccagcgtaat gttggcaact gcgccaccat ttggcatgta   6000
gcgtacttcc gggtcctgac ccagattacc aacgagaata accttgttta cgcctctgct   6060
ggccatgttc gtgtctcctg aaaaaaatcg ttctgaataa gtgtaaacgc gcgattgtac   6120
cattaccaat agcgctttta ctatgttgtg acctcggttc cgggaaacaa acctggccag   6180
acattgttac acaacactcc ggataatgca ttccaatact gtatattcat tcaggtcaat   6240
catatgaagg gcgaattctg cagatatcca tcacactggc ggccgccagt gtgatggata   6300
tctgcagaat tcgcccttga gaagttccta ttctatatat agtataggaa cttctctaga   6360
acttttgtta cccgccaaac aaaacccaaa aacaacccat acccaaccca ataaaacacc   6420
aaaacaagac aaataatcat tgattgatgg ttgaaatggg gtaaacttga caaacaaacc   6480
cacttaaaac ccaaaacata cccaaacaca caccaaaaaa acaccataag gagttttata   6540
aatgttggta ttcattgatg acggttcaac aaacatcaaa ctacagtggc aggaaagcga   6600
cggaacaatt aaacagcaca ttagcccgaa cagcttcaaa cgcgagtggg cagtctcttt   6660
tggtgataaa aaggtcttta actacacact gaacggcgaa cagtattcat ttgatccaat   6720
cagcccggat gctgtagtca caaccaatat cgcatggcaa tacagcgacg ttaatgtcgt   6780
tgcagtgcat cacgccttac tgaccagtgg tctgccggta agcgaagtgg atattgtttg   6840
cacacttcct ctgacagagt attacgacag aaataaccaa cccaatacgg aaaatattga   6900
```

```
gcgtaagaaa gcaaacttcc ggaaaaaaat tacattaaat ggcggggata cattcacaat   6960

aaaagatgta aaagtcatgc ctgaatctat accggcaggt tatgaagttc tacaagaact   7020

ggatgagtta gattctttat taattataga tctcgggggc accacattag atatttctca   7080

ggtaatgggg aaattatcgg ggatcagtaa aatatacgga gactcatctc ttggtgtctc   7140

tctggttaca tctgcagtaa aagatgccct ttctcttgcg agaacaaaag gaagtagcta   7200

tcttgctgac gatataatca ttcacagaaa agataataac tatctgaagc aacgaattaa   7260

tgatgagaac aaaatatcaa tagtcaccga agcaatgaat gaagcacttc gtaaacttga   7320

gcaacgtgta ttaaatacgc tcaatgaatt ttctggttat actcatgtta tggttatagg   7380

cggtggcgca gaattaatat gcgatgcagt aaaaaaacac acacagattc gtgatgaacg   7440

ttttttcaaa accaataact ctcaatatga tttagttaac ggtatgtatc tcataggtaa   7500

ttaatgatgg acaagcgcag aaccattgcc ttcaaactaa atccagatgt aaatcaaaca   7560

gataaaattg tttgtgatac actggacagt atcccgcaag gggaacgaag ccgccttaac   7620

cgggccgcac tgacggcagg tctggcctta tacagacaag atccccggac ccctttcctt   7680

ttatgtgagc tgctgacgaa agaaaccaca ttttcagata tcgtgaatat attgagatcg   7740

ctatttccaa aagagatggc cgattttaat tcttcaatag tcactcaatc ctcttcacaa   7800

caagagcaaa aaagtgatga agagaccaaa aaaaatgcga tgaagctaat aaattaattc   7860

aattattatt gagttcccct tatccactat caggctggat aaagggaact caatcaagtt   7920

attttcttac cagtcattac ataatcgtta ttatgaaata atcgtttgca ctgtctctgt   7980

tattcaggca atttcaataa aggcacttgc tcacgctctg tcattttctg aaactcttca   8040

tgctg                                                               8045
```

```
<210> SEQ ID NO 37
<211> LENGTH: 838
<212> TYPE: PRT
<213> ORGANISM: Artificial Sequence
<220> FEATURE:
<223> OTHER INFORMATION: Amino acid sequence of ClyA-CBD/B

<400> SEQUENCE: 37

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
```

-continued

```
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser Gly Leu Ile Tyr Ile Asn Asp Ser Leu Tyr Tyr Phe Lys Pro Pro
305                 310                 315                 320

Val Asn Asn Leu Ile Thr Gly Phe Val Thr Val Gly Asp Asp Lys Tyr
                325                 330                 335

Tyr Phe Asn Pro Ile Asn Gly Gly Ala Ala Ser Ile Gly Glu Thr Ile
            340                 345                 350

Ile Asp Asp Lys Asn Tyr Tyr Phe Asn Gln Ser Gly Val Leu Gln Thr
        355                 360                 365

Gly Val Phe Ser Thr Glu Asp Gly Phe Lys Tyr Phe Ala Pro Ala Asn
    370                 375                 380

Thr Leu Asp Glu Asn Leu Glu Gly Glu Ala Ile Asp Phe Thr Gly Lys
385                 390                 395                 400

Leu Ile Ile Asp Glu Asn Ile Tyr Tyr Phe Asp Asp Asn Tyr Arg Gly
                405                 410                 415

Ala Val Glu Trp Lys Glu Leu Asp Gly Glu Met His Tyr Phe Ser Pro
            420                 425                 430

Glu Thr Gly Lys Ala Phe Lys Gly Leu Asn Gln Ile Gly Asp Tyr Lys
        435                 440                 445

Tyr Tyr Phe Asn Ser Asp Gly Val Met Gln Lys Gly Phe Val Ser Ile
    450                 455                 460

Asn Asp Asn Lys His Tyr Phe Asp Asp Ser Gly Val Met Lys Val Gly
465                 470                 475                 480

Tyr Thr Glu Ile Asp Gly Lys His Phe Tyr Phe Ala Glu Asn Gly Glu
                485                 490                 495

Met Gln Ile Gly Val Phe Asn Thr Glu Asp Gly Phe Lys Tyr Phe Ala
            500                 505                 510

His His Asn Glu Asp Leu Gly Asn Glu Glu Gly Glu Glu Ile Ser Tyr
        515                 520                 525

Ser Gly Ile Leu Asn Phe Asn Asn Lys Ile Tyr Tyr Phe Asp Asp Ser
    530                 535                 540

Phe Thr Ala Val Val Gly Trp Lys Asp Leu Glu Asp Gly Ser Lys Tyr
545                 550                 555                 560

Tyr Phe Asp Glu Asp Thr Ala Glu Ala Tyr Ile Gly Leu Ser Leu Ile
                565                 570                 575
```

-continued

Asn Asp Gly Gln Tyr Tyr Phe Asn Asp Asp Gly Ile Met Gln Val Gly
580 585 590

Phe Val Thr Ile Asn Asp Lys Val Phe Tyr Phe Ser Asp Ser Gly Ile
595 600 605

Ile Glu Ser Gly Val Gln Asn Ile Asp Asp Asn Tyr Phe Tyr Ile Asp
610 615 620

Asp Asn Gly Ile Val Gln Ile Gly Val Phe Asp Thr Ser Asp Gly Tyr
625 630 635 640

Lys Tyr Phe Ala Pro Ala Asn Thr Val Asn Asp Asn Ile Tyr Gly Gln
645 650 655

Ala Val Glu Tyr Ser Gly Leu Val Arg Val Gly Glu Asp Val Tyr Tyr
660 665 670

Phe Gly Glu Thr Tyr Thr Ile Glu Thr Gly Trp Ile Tyr Asp Met Glu
675 680 685

Asn Glu Ser Asp Lys Tyr Tyr Phe Asn Pro Glu Thr Lys Lys Ala Cys
690 695 700

Lys Gly Ile Asn Leu Ile Asp Asp Ile Lys Tyr Tyr Phe Asp Glu Lys
705 710 715 720

Gly Ile Met Arg Thr Gly Leu Ile Ser Phe Glu Asn Asn Asn Tyr Tyr
725 730 735

Phe Asn Glu Asn Gly Glu Met Gln Phe Gly Tyr Ile Asn Ile Glu Asp
740 745 750

Lys Met Phe Tyr Phe Gly Glu Asp Gly Val Met Gln Ile Gly Val Phe
755 760 765

Asn Thr Pro Asp Gly Phe Lys Tyr Phe Ala His Gln Asn Thr Leu Asp
770 775 780

Glu Asn Phe Glu Gly Glu Ser Ile Asn Tyr Thr Gly Trp Leu Asp Leu
785 790 795 800

Asp Glu Lys Arg Tyr Tyr Phe Thr Asp Glu Tyr Ile Ala Ala Thr Gly
805 810 815

Ser Val Ile Ile Asp Gly Glu Glu Tyr Tyr Phe Asp Pro Asp Thr Ala
820 825 830

Gln Leu Val Ile Ser Glu
835

<210> SEQ ID NO 38
<211> LENGTH: 305
<212> TYPE: PRT
<213> ORGANISM: Salmonella typhi

<400> SEQUENCE: 38

Met Thr Ser Ile Phe Ala Glu Gln Thr Val Glu Val Val Lys Ser Ala
1 5 10 15

Ile Glu Thr Ala Asp Gly Ala Leu Asp Leu Tyr Asn Lys Tyr Leu Asp
20 25 30

Gln Val Ile Pro Trp Lys Thr Phe Asp Glu Thr Ile Lys Glu Leu Ser
35 40 45

Arg Phe Lys Gln Glu Tyr Ser Gln Glu Ala Ser Val Leu Val Gly Asp
50 55 60

Ile Lys Val Leu Leu Met Asp Ser Gln Asp Lys Tyr Phe Glu Ala Thr
65 70 75 80

Gln Thr Val Tyr Glu Trp Cys Gly Val Val Thr Gln Leu Leu Ser Ala
85 90 95

Tyr Ile Leu Leu Phe Asp Glu Tyr Asn Glu Lys Lys Ala Ser Ala Gln

-continued 100 105 110

Lys Asp Ile Leu Ile Arg Ile Leu Asp Asp Gly Val Lys Lys Leu Asn
115 120 125

Glu Ala Gln Lys Ser Leu Leu Thr Ser Ser Gln Ser Phe Asn Asn Ala
130 135 140

Ser Gly Lys Leu Leu Ala Leu Asp Ser Gln Leu Thr Asn Asp Phe Ser
145 150 155 160

Glu Lys Ser Ser Tyr Phe Gln Ser Gln Val Asp Arg Ile Arg Lys Glu
165 170 175

Ala Tyr Ala Gly Ala Ala Ala Gly Ile Val Ala Gly Pro Phe Gly Leu
180 185 190

Ile Ile Ser Tyr Ser Ile Ala Ala Gly Val Ile Glu Gly Lys Leu Ile
195 200 205

Pro Glu Leu Asn Asn Arg Leu Lys Thr Val Gln Asn Phe Phe Thr Ser
210 215 220

Leu Ser Ala Thr Val Lys Gln Ala Asn Lys Asp Ile Asp Ala Ala Lys
225 230 235 240

Leu Lys Leu Ala Thr Glu Ile Ala Ala Ile Gly Glu Ile Lys Thr Glu
245 250 255

Thr Glu Thr Thr Arg Phe Tyr Val Asp Tyr Asp Asp Leu Met Leu Ser
260 265 270

Leu Leu Lys Gly Ala Ala Lys Lys Met Ile Asn Thr Cys Asn Glu Tyr
275 280 285

Gln Gln Arg His Gly Lys Lys Thr Leu Phe Glu Val Pro Asp Val Ala
290 295 300

Ser
305

<210> SEQ ID NO 39
<211> LENGTH: 921
<212> TYPE: DNA
<213> ORGANISM: Salmonella typhi

<400> SEQUENCE: 39
atgactagta tttttgcaga acaaactgta gaggtagtta aaagcgcgat cgaaaccgca 60
gatggggcat tagatcttta taacaaatac ctcgaccagg tcatccccctg gaagaccttt 120 gatgaaacca taaaagagtt aagccgtttt aaacaggagt actcgcagga agcttctgtt 180
ttagttggtg atattaaagt tttgcttatg gacagccagg acaagtattt tgaagcgaca 240
caaactgttt atgaatggtg tggtgtcgtg acgcaattac tctcagcgta tattttacta 300
tttgatgaat ataatgagaa aaaagcatca gcccagaaag acattctcat taggatatta 360
gatgatggtg tcaagaaact gaatgaagcg caaaaatctc tcctgacaag ttcacaaagt 420
ttcaacaacg cttccggaaa actgctggca ttagatagcc agttaactaa tgatttttcg 480
gaaaaaagta gttatttcca gtcacaggtg gatagaattc gtaaggaagc ttatgccggt 540
gctgcagccg gcatagtcgc cggtccgttt ggattaatta tttcctattc tattgctgcg 600
ggcgtgattg aagggaaatt gattccagaa ttgaataaca ggctaaaaac agtgcaaaat 660
ttctttacta gcttatcagc tacagtgaaa caagcgaata aagatatcga tgcggcaaaa 720
ttgaaattag ccactgaaat agcagcaatt ggggagataa aaacggaaac cgaaacaacc 780
agattctacg ttgattatga tgatttaatg ctttctttat taaaaggagc tgcaaagaaa 840
atgattaaca cctgtaatga ataccaacaa cgtcatggta agaagacgct tttcgaggtt 900
cctgacgtcg ctagctgata a 921

<210> SEQ ID NO 40
<211> LENGTH: 909
<212> TYPE: DNA
<213> ORGANISM: Artificial Sequence
<220> FEATURE:
<223> OTHER INFORMATION: chemically-synthesized codon-optimized S. Typhi clyA polynucleotide sequence

<400> SEQUENCE: 40
atgactagta tttttgcgga acagaccgtg gaagtggtta aaagcgcgat cgaaaccgcg 60
gatggcgcgt tagatcttta taacaaatat ctggatcagg tgattccgtg gaaaaccttt 120
gatgaaacca ttaaagaact gagccgtttt aaacaggaat atagccagga agcgagcgtg 180
ctggtgggcg atattaaagt gctgctgatg gatagccagg ataaatattt tgaagcgacc 240
cagaccgtgt atgaatggtg cggcgtggtt acccagctgc tgagcgcgta tatcctgctg 300
tttgatgaat ataacgaaaa gaaagcgagc gctcagaaag atattctgat tcgtattctg 360
gatgacggcg tgaaaaaact gaacgaagcg cagaaaagcc tgctgaccag cagccagagc 420
tttaacaatg cgtccggaaa actgctggcg ctggatagcc agctgaccaa cgattttagc 480
gaaaaaagca gctattttca gagccaggtg gatagaattc gtaaagaagc ctatgccggc 540
gctgcagccg gcattgtggc tggtccgttt ggcctgatta tcagctatag cattgccgcg 600
ggcgttattg aaggcaaact gattccggaa ctgaataacc gtctgaaaac cgttcagaat 660
ttctttacaa gcttaagcgc gaccgtgaaa caggcgaaca aagatatcga tgcggcaaaa 720
ctgaaactgg cgaccgaaat tgcggctatt ggcgaaatta aaaccgaaac cgaaaccacc 780
cgtttttatg tggattatga tgacctgatg ctgagcctgc tgaaaggcgc ggcaaagaaa 840
atgattaaca cctgcaacga atatcagcag cgtcatggca agaaaaccct gtttgaagtg 900
ccggatgtg 909

<210> SEQ ID NO 41
<211> LENGTH: 1102
<212> TYPE: DNA
<213> ORGANISM: Salmonella typhi

<400> SEQUENCE: 41
ggaggtaata ggtaagaata ctttataaaa caggtactta attgcaattt atatatttaa 60
agaggcaaat gattatgacc ggaatatttg cagaacaaac tgtagaggta gttaaaagcg 120
cgatcgaaac cgcagatggg gcattagatc tttataacaa atacctcgac caggtcatcc 180
cctggaagac ctttgatgaa accataaaag agttaagccg ttttaaacag gagtactcgc 240
aggaagcttc tgttttagtt ggtgatatta aagttttgct tatggacagc caggacaagt 300
attttgaagc gacacaaact gtttatgaat ggtgtggtgt cgtgacgcaa ttactctcag 360
cgtatatttt actatttgat gaatataatg agaaaaaagc atcagcccag aaagacattc 420
tcattaggat attagatgat ggtgtcaaga aactgaatga agcgcaaaaa tctctcctga 480
caagttcaca aagtttcaac aacgcttccg gaaaactgct ggcattagat agccagttaa 540
ctaatgattt ttcggaaaaa agtagttatt tccagtcaca ggtggataga attcgtaagg 600
aagcttatgc cggtgctgca gccggcatag tcgccggtcc gtttggatta attatttcct 660
attctattgc tgcgggcgtg attgaaggga aattgattcc agaattgaat aacaggctaa 720
aaacagtgca aaatttcttt actagcttat cagctacagt gaaacaagcg aataaagata 780

-continued

```
tcgatgcggc aaaattgaaa ttagccactg aaatagcagc aattggggag ataaaaacgg    840

aaaccgaaac aaccagattc tacgttgatt atgatgattt aatgctttct ttattaaaag    900

gagctgcaaa gaaaatgatt aacacctgta atgaatacca acaaagacac ggtaagaaga    960

cgcttttcga ggttcctgac gtctgataca ttttcattcg atctgtgtac ttttaacgcc   1020

cgatagcgta aagaaaatga gagacggaga aaaagcgata ttcaacagcc cgataaacaa   1080

gagtcgttac cgggctgacg ag                                            1102
```

```
<210> SEQ ID NO 42
<211> LENGTH: 1102
<212> TYPE: DNA
<213> ORGANISM: Salmonella paratyphi

<400> SEQUENCE: 42

ggaggcaata ggtaggaata agttataaaa caatagctta attgcaattt atatatttaa     60

agaggcaaat gattatgact ggaatatttg cagaacaaac tgtagaggta gttaaaagcg    120

cgatcgaaac cgcagatggg gcattagatt tttataacaa atacctcgac caggttatcc    180

cctggaagac ctttgatgaa accataaaag agttaagccg ttttaaacag gagtactcgc    240

aggaagcttc tgttttagtt ggtgatatta aagttttgct tatggacagc caggataagt    300

attttgaagc gacacaaact gtttatgaat ggtgtggtgt cgtgacgcaa ttactctcag    360

cgtatatttt actatttgat gaatataatg agaaaaaagc atcagcgcag aaagacattc    420

tcatcaggat attagatgat ggcgtcaata aactgaatga agcgcaaaaa tctctcctgg    480

gaagttcaca aagtttcaac aacgcttcag gaaaactgct ggcattagat agccagttaa    540

ctaatgattt ctcggaaaaa agtagttatt tccagtcaca ggtggataga attcgtaagg    600

aagcttatgc cggtgctgca gcaggcatag tcgccggtcc gtttggatta attatttcct    660

attctattgc tgcgggcgtg attgaaggga aattgattcc agaattgaat gacaggctaa    720

aagcagtgca aaatttcttt actagcttat cagtcacagt gaaacaagcg aataaagata    780

tcgatgcggc aaaattgaaa ttagccactg aaatagcagc aattggggag ataaaaacgg    840

aaaccgaaac aaccagattc tacgttgatt atgatgattt aatgctttct ttactaaaag    900

gagctgcaaa gaaaatgatt aacacctgta atgaatacca acaaaggcac ggtaagaaga    960

cgcttctcga ggttcctgac atctgataca ttttcattcg ctctgtttac ttttaacgcc   1020

cgatagcgtg aagaaaatga gagacggaga aaaagcgata ttcaacagcc cgataaacaa   1080

gagtcgttac cgggctggcg ag                                            1102
```

```
<210> SEQ ID NO 43
<211> LENGTH: 904
<212> TYPE: DNA
<213> ORGANISM: Shigella flexneri

<400> SEQUENCE: 43

atgactgaaa tcgttgcaga taaaacggta gaagtagtta aaaacgcaat cgaaaccgca     60

gatggagcat tagatcttta taataaatat ctcgatcagg tcatcccctg gcagaccttt    120

gatgaaacca taaaagagtt aagtcgcttt aaacaggagt attcacaggc agcctccgtt    180

ttagtcggcg atattaaaac cttacttatg gatagccagg ataagtattt tgaagcaacc    240

caaacagtgt atgaatggtg tggtgttgcg acgcaattgc tcgcagcgta tattttgcta    300

tttgatgagt acaatgagaa gaaagcatcc gcccctcatt aaggtactgg atgacggcat    360

cacgaagctg aatgaagcgc aaaattccct gctggtaagc tcacaaagtt tcaacaacgc    420
```

-continued ttccgggaaa ctgctggcgt tagatagcca gttaaccaat gatttttcag aaaaaagcag 480
ctatttccag tcacaggtag ataaaatcag gaaggaagcg tatgccggtg ccgcagccgg 540
tgtcgtcgcc ggtccatttg gtttaatcat ttcctattct attgctgcgg gcgtagttga 600
agggaaactg attccagaat tgaagaacaa gttaaaatct gtgcagagtt tctttaccac 660
cctgtctaac acggttaaac aagcgaataa agatatcgat gccgccaaat tgaaattaac 720
caccgaaata gccgccatcg gggagataaa aacggaaact gaaaccacca gattctatgt 780
tgattatgat gatttaatgc tttctttgct aaaagcagcg gccaaaaaaa tgattaacac 840
ctgtaatgag tatcagaaaa gacacggtaa aaagacactc tttgaggtac ctgaagtctg 900
ataa 904

<210> SEQ ID NO 44
<211> LENGTH: 1080
<212> TYPE: DNA
<213> ORGANISM: Escherichia coli

<400> SEQUENCE: 44
agaaataaag acattgacgc atcccgcccg gctaactatg aattagatga agtaaaattt 60
attaatagtt gtaaaacagg agtttcatta caatttatat atttaaagag gcgaatgatt 120
atgactgaaa tcgttgcaga taaaacggta gaagtagtta aaaacgcaat cgaaaccgca 180
gatggagcat tagatcttta taataaatat ctcgatcagg tcatcccctg gcagaccttt 240
gatgaaacca taaaagagtt aagtcgcttt aaacaggagt attcacaggc agcctccgtt 300
ttagtcggcg atattaaaac cttacttatg gatagccagg ataagtattt tgaagcaacc 360
caaacagtgt atgaatggtg tggtgttgcg acgcaattgc tcgcagcgta tattttgcta 420
tttgatgagt acaatgagaa gaaagcatcc gcccagaaag acattctcat taaggtactg 480
gatgacggca tcacgaagct gaatgaagcg caaaaatccc tgctggtaag ctcacaaagt 540
ttcaacaacg cttccgggaa actgctggcg ttagatagcc agttaaccaa tgatttttca 600
gaaaaaagca gctatttcca gtcacaggta gataaaatca ggaaggaagc atatgccggt 660
gccgcagccg gtgtcgtcgc cggtccattt ggattaatca tttcctattc tattgctgcg 720
ggcgtagttg aaggaaaact gattccagaa ttgaagaaca agttaaaatc tgtgcagaat 780
ttctttacca ccctgtctaa cacggttaaa caagcgaata aagatatcga tgccgccaaa 840
ttgaaattaa ccaccgaaat agccgccatc ggtgagataa aaacggaaac tgaaacaacc 900
agattctacg ttgattatga tgatttaatg ctttctttgc taaaagaagc ggccaaaaaa 960
atgattaaca cctgtaatga gtatcagaaa agacacggta aaaagacact ctttgaggta 1020
cctgaagtct gataagcgat tattctctcc atgtactcaa ggtataaggt ttatcacatt 1080

<210> SEQ ID NO 45
<211> LENGTH: 7200
<212> TYPE: DNA
<213> ORGANISM: Artificial Sequence
<220> FEATURE:
<223> OTHER INFORMATION: pSEC10S2 expression plasmid

<400> SEQUENCE: 45
gaattctgtg gtagcacaga ataatgaaaa gtgtgtaaag aagggtaaaa aaaaccgaat 60
gcgaggcatc cggttgaaat aggggtaaac agacattcag aaatgaatga cggtaataaa 120
taaagttaat gatgatagcg ggagttattc tagttgcgag tgaaggtttt gttttgacat 180

```
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcatttttg gggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaaatgac tagtattttt gcagaacaaa    540
ctgtagaggt agttaaaagc gcgatcgaaa ccgcagatgg ggcattagac ctttataaca    600
aatacctcga ccaggtcatc ccctggaaga cctttgatga aaccataaaa gagttaagcc    660
gttttaaaca ggagtactcg caggaggctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagatga tggtgtcaag aaactgaatg    900
aagcgcaaaa atctctcctg acaagttcac aaagtttcaa caacgcttcc ggaaaactgc    960
tggcattaga tagccagctg actaatgatt tttcggaaaa aagtagttat ttccagtcac   1020
aggtggatag aatccgtaag gaggcttatg ccggtgctgc agccggcata gtcgccggtc   1080
cgtttggatt aattatttcc tattctattg ctgcgggcgt gattgaaggg aaattgattc   1140
cagaattgaa taacaggcta aaaacagtgc aaaatttctt tactagctta tcagctacag   1200
tgaaacaagc gaataaagat atcgatgcgg caaaattgaa attagccact gaaatagcag   1260
cgattgggga gataaaaacg gaaaccgaaa caaccagatt ctacgttgat tatgatgatt   1320
taatgctttc tttattaaaa ggagctgcaa agaaaatgat taacacctgt aatgaatacc   1380
aacaacgtca tggtaagaag acgcttttcg aggttcctga cgtcgctagc tgataaccta   1440
gcccgcctaa tgagcgggct tttttttctc ggcctaggtt tcacctgttc tattaggtgt   1500
tacatgctgt tcatctgtta cattgtcgat ctgttcatgg tgaacagctt taaatgcacc   1560
aaaaactcgt aaaagctctg atgtatctat cttttttaca ccgttttcat ctgtgcatat   1620
ggacagtttt ccctttgata tctaacggtg aacagttgtt ctacttttgt ttgttagtct   1680
tgatgcttca ctgatagata caagagccat aagaacctca gatccttccg tatttagcca   1740
gtatgttctc tagtgtggtt cgttgttttt gcgtgagcca tgagaacgaa ccattgagat   1800
catgcttact ttgcatgtca ctcaaaaatt ttgcctcaaa actggtgagc tgaatttttg   1860
cagttaaagc atcgtgtagt gtttttctta gtccgttacg taggtaggaa tctgatgtaa   1920
tggttgttgg tattttgtca ccattcattt ttatctggtt gttctcaagt tcggttacga   1980
gatccatttg tctatctagt tcaacttgga aaatcaacgt atcagtcggg cggcctcgct   2040
tatcaaccac caatttcata ttgctgtaag tgtttaaatc tttacttatt ggtttcaaaa   2100
cccattggtt aagcctttta aactcatggt agttattttc aagcattaac atgaacttaa   2160
attcatcaag gctaatctct atatttgcct tgtgagtttt cttttgtgtt agttctttta   2220
ataaccactc ataaatcctc atagagtatt tgttttcaaa agacttaaca tgttccagat   2280
tatattttat gaattttttt aactggaaaa gataaggcaa tatctcttca ctaaaaacta   2340
attctaattt ttcgcttgag aacttggcat agtttgtcca ctggaaaatc tcaaagcctt   2400
taaccaaagg attcctgatt tccacagttc tcgtcatcag ctctctggtt gctttagcta   2460
atacaccata agcattttcc ctactgatgt tcatcatctg agcgtattgg ttataagtga   2520
acgataccgt ccgttctttc cttgtagggt tttcaatcgt ggggttgagt agtgccacac   2580
```

-continued

```
agcataaaat tagcttggtt tcatgctccg ttaagtcata gcgactaatc gctagttcat   2640
ttgctttgaa aacaactaat tcagacatac atctcaattg gtctaggtga ttttaatcac   2700
tataccaatt gagatgggct agtcaatgat aattactagt ccttttcctt tgagttgtgg   2760
gtatctgtaa attctgctag acctttgctg gaaaacttgt aaattctgct agaccctctg   2820
taaattccgc tagacctttg tgtgtttttt ttgtttatat tcaagtggtt ataatttata   2880
gaataaagaa agaataaaaa aagataaaaa gaatagatcc cagccctgtg tataactcac   2940
tactttagtc agttccgcag tattacaaaa ggatgtcgca aacgctgttt gctcctctac   3000
aaaacagacc ttaaaaccct aaaggcttaa gtagcaccct cgcaagctcg ggcaaatcgc   3060
tgaatattcc ttttgtctcc gaccatcagg cacctgagtc gctgtctttt tcgtgacatt   3120
cagttcgctg cgctcacggc tctggcagtg aatgggggta aatggcacta caggcgcctt   3180
ttatggattc atgcaaggaa actacccata atacaagaaa agcccgtcac gggcttctca   3240
gggcgtttta tggcgggtct gctatgtggt gctatctgac tttttgctgt tcagcagttc   3300
ctgccctctg attttccagt ctgaccactt cggattatcc cgtgacaggt cattcagact   3360
ggctaatgca cccagtaagg cagcggtatc atcaacaggc ttacccgtct tactgtcaac   3420
cggatctaaa acactaggcc caagagtttg tagaaacgca aaaaggccat ccgtcaggat   3480
ggccttctgc ttaatttgat gcctggcagt ttatggcggg cgtcctgccc gccaccctcc   3540
gggccgttgc ttcgcaacgt tcaaatccgc tcccggcgga tttgtcctac tcaggagagc   3600
gttcaccgac aaacaacaga taaaacgaaa ggcccagtct ttcgactgag cctttcgttt   3660
tatttgatgc ctggcagttc cctactctcg catggggaga ccccacacta ccatcggcgc   3720
tacggcgttt cacttctgag ttcggcatgg ggtcaggtgg gaccaccgcg ctactgccgc   3780
caggcaaatt ctgttttatc agaccgcttc tgcgttctga tttaatctgt atcaggctga   3840
aaatcttctc tcatccgcca aaacagccaa gctggatcta aaacactagc ccaacctttc   3900
atagaaggcg gcggtggaat cgaaatctcg tgatggcagg ttgggcgtcg cttggtcggt   3960
catttcgaac cccagagtcc cgctcagaag aactcgtcaa gaaggcgata gaaggcgatg   4020
cgctgcgaat cgggagcggc gataccgtaa agcacgagga agcggtcagc ccattcgccg   4080
ccaagctctt cagcaatatc acgggtagcc aacgctatgt cctgatagcg gtccgccaca   4140
cccagccggc cacagtcgat gaatccagaa aagcggccat tttccaccat gatattcggc   4200
aagcaggcat cgccatgggt cacgacgaga tcctcgccgt cgggcatgcg cgccttgagc   4260
ctggcgaaca gttcggctgg cgcgagcccc tgatgctctt cgtccagatc atcctgatcg   4320
acaagaccgg cttccatccg agtacgtgct cgctcgatgc gatgtttcgc ttggtggtcg   4380
aatgggcagg tagccggatc aagcgtatgc agccgccgca ttgcatcagc catgatggat   4440
actttctcgg caggagcaag gtgagatgac aggagatcct gccccggcac ttcgcccaat   4500
agcagccagt cccttcccgc ttcagtgaca acgtcgagca cagctgcgca aggaacgccc   4560
gtcgtggcca gccacgatag ccgcgctgcc tcgtcctgca gttcattcag ggcaccggac   4620
aggtcggtct tgacaaaaag aaccgggcgc ccctgcgctg acagccggaa cacggcggca   4680
tcagagcagc cgattgtctg ttgtgcccag tcatagccga atagcctctc cacccaagcg   4740
gccggagaac ctgcgtgcaa tccatcttgt tcaatcatgc gaaacgatcc tcatcctgtc   4800
tcttgatcag atcttgatcc cctgcgccat cagatccttg gcggcaagaa agccatccag   4860
tttactttgc agggcttccc aaccttacca gagggcgccc cagccgtggc aattccggtt   4920
```

-continued

```
cgctgctaga caacatcagc aaggagaaag gggctaccgg cgaaccagca gcccctttat   4980
aaaggcgctt cagtagtcag accagcatca gtcctgaaaa ggcgggcctg cgcccgcctc   5040
caggttgcta cttaccggat tcgtaagcca tgaaagccgc cacctccctg tgtccgtctc   5100
tgtaacgaat ctcgcacagc gattttcgtg tcagataagt gaatatcaac agtgtgagac   5160
acacgatcaa cacacaccag acaagggaac ttcgtggtag tttcatggcc ttcttctcct   5220
tgcgcaaagc gcggtaagag gctatcctga tgtggactag acatagggat gcctcgtggt   5280
ggttaatgaa aattaactta ctacggggct atcttctttc tgccacacaa cacggcaaca   5340
aaccaccttc acgtcatgag gcagaaagcc tcaagcgccg ggcacatcat agcccatata   5400
cctgcacgct gaccacactc actttccctg aaaataatcc gctcattcag accgttcacg   5460
ggaaatccgt gtgattgttg ccgcatcacg ctgcctcccg gagtttgtct cgagcacttt   5520
tgttacccgc caaacaaaac ccaaaaacaa cccataccca acccaataaa acaccaaaac   5580
aagacaaata atcattgatt gatggttgaa atggggtaaa cttgacaaac aaacccactt   5640
aaaacccaaa acatacccaa acacacacca aaaaaacacc ataaggagtt ttataaatgt   5700
tggtattcat tgatgacggt tcaacaaaca tcaaactaca gtggcaggaa agcgacggaa   5760
caattaaaca gcacattagc ccgaacagct tcaaacgcga gtgggcagtc tcttttggtg   5820
ataaaaaggt ctttaactac acactgaacg gcgaacagta ttcatttgat ccaatcagcc   5880
cggatgctgt agtcacaacc aatatcgcat ggcaatacag cgacgttaat gtcgttgcag   5940
tgcatcacgc cttactgacc agtggtctgc cggtaagcga agtggatatt gtttgcacac   6000
ttcctctgac agagtattac gacagaaata accaacccaa tacggaaaat attgagcgta   6060
agaaagcaaa cttccggaaa aaaattacat taaatggcgg ggatacattc acaataaaag   6120
atgtaaaagt catgcctgaa tctataccgg caggttatga agttctacaa gaactggatg   6180
agttagattc tttattaatt atagatctcg gggcaccac attagatatt tctcaggtaa   6240
tggggaaatt atcggggatc agtaaaatat acggagactc atctcttggt gtctctctgg   6300
ttacatctgc agtaaaagat gccctttctc ttgcgagaac aaaaggaagt agctatcttg   6360
ctgacgatat aatcattcac agaaaagata ataactatct gaagcaacga attaatgatg   6420
agaacaaaat atcaatagtc accgaagcaa tgaatgaagc acttcgtaaa cttgagcaac   6480
gtgtattaaa tacgctcaat gaattttctg gttatactca tgttatggtt ataggcggtg   6540
gcgcagaatt aatatgcgat gcagtaaaaa aacacacaca gattcgtgat gaacgttttt   6600
tcaaaaccaa taactctcaa tatgatttag ttaacggtat gtatctcata ggtaattaat   6660
gatggacaag cgcagaacca ttgccttcaa actaaatcca gatgtaaatc aaacagataa   6720
aattgtttgt gatacactgg acagtatccc gcaaggggaa cgaagccgcc ttaaccgggc   6780
cgcactgacg gcaggtctgg ccttatacag acaagatccc cggacccctt tccttttatg   6840
tgagctgctg acgaaagaaa ccacattttc agatatcgtg aatatattga gatcgctatt   6900
tccaaaagag atggccgatt ttaattcttc aatagtcact caatcctctt cacaacaaga   6960
gcaaaaaagt gatgaagaga ccaaaaaaaa tgcgatgaag ctaataaatt aattcaatta   7020
ttattgagtt ccctttatcc actatcaggc tggataaagg gaactcaatc aagttatttt   7080
cttaccagtc attacataat cgttattatg aaataatcgt ttgcactgtc tctgttattc   7140
aggcaatttc aataaaggca cttgctcacg ctctgtcatt ttctgaaact cttcatgctg   7200
```

<210> SEQ ID NO 46
<211> LENGTH: 878

-continued

<212> TYPE: PRT
<213> ORGANISM: Clostridium difficile

<400> SEQUENCE: 46

Met Ala Ser Lys Ile Gln Met Arg Asn Lys Lys Val Leu Ser Phe Leu
1 5 10 15

Thr Leu Thr Ala Ile Val Ser Gln Ala Leu Val Tyr Pro Val Tyr Ala
20 25 30

Gln Thr Ser Thr Ser Asn His Ser Asn Lys Lys Lys Glu Ile Val Asn
35 40 45

Glu Asp Ile Leu Pro Asn Asn Gly Leu Met Gly Tyr Tyr Phe Thr Asp
50 55 60

Glu His Phe Lys Asp Leu Lys Leu Met Ala Pro Ile Lys Asp Gly Asn
65 70 75 80

Leu Lys Phe Glu Glu Lys Lys Val Asp Lys Leu Leu Asp Lys Asp Lys
85 90 95

Ser Asp Val Lys Ser Ile Arg Trp Thr Gly Arg Ile Ile Pro Ser Lys
100 105 110

Asp Gly Glu Tyr Thr Leu Ser Thr Asp Arg Asp Asp Val Leu Met Gln
115 120 125

Val Asn Thr Glu Ser Thr Ile Ser Asn Thr Leu Lys Val Asn Met Lys
130 135 140

Lys Gly Lys Glu Tyr Lys Val Arg Ile Glu Leu Gln Asp Lys Asn Leu
145 150 155 160

Gly Ser Ile Asp Asn Leu Ser Ser Pro Asn Leu Tyr Trp Glu Leu Asp
165 170 175

Gly Met Lys Lys Ile Ile Pro Glu Glu Asn Leu Phe Leu Arg Asp Tyr
180 185 190

Ser Asn Ile Glu Lys Asp Asp Pro Phe Ile Pro Asn Asn Asn Phe Phe
195 200 205

Asp Pro Lys Leu Met Ser Asp Trp Glu Asp Glu Asp Leu Asp Thr Asp
210 215 220

Asn Asp Asn Ile Pro Asp Ser Tyr Glu Arg Asn Gly Tyr Thr Ile Lys
225 230 235 240

Asp Leu Ile Ala Val Lys Trp Glu Asp Ser Phe Ala Glu Gln Gly Tyr
245 250 255

Lys Lys Tyr Val Ser Asn Tyr Leu Glu Ser Asn Thr Ala Gly Asp Pro
260 265 270

Tyr Thr Asp Tyr Glu Lys Ala Ser Gly Ser Phe Asp Lys Ala Ile Lys
275 280 285

Thr Glu Ala Arg Asp Pro Leu Val Ala Ala Tyr Pro Ile Val Gly Val
290 295 300

Gly Met Glu Lys Leu Ile Ile Ser Thr Asn Glu His Ala Ser Thr Asp
305 310 315 320

Gln Gly Lys Thr Val Ser Arg Ala Thr Thr Asn Ser Lys Thr Glu Ser
325 330 335

Asn Thr Ala Gly Val Ser Val Asn Val Gly Tyr Gln Asn Gly Phe Thr
340 345 350

Ala Asn Val Thr Thr Asn Tyr Ser His Thr Thr Asp Asn Ser Thr Ala
355 360 365

Val Gln Asp Ser Asn Gly Glu Ser Trp Asn Thr Gly Leu Ser Ile Asn
370 375 380

Lys Gly Glu Ser Ala Tyr Ile Asn Ala Asn Val Arg Tyr Tyr Asn Thr
385 390 395 400

-continued

```
Gly Thr Ala Pro Met Tyr Lys Val Thr Pro Thr Thr Asn Leu Val Leu
                405                 410                 415

Asp Gly Asp Thr Leu Ser Thr Ile Lys Ala Gln Glu Asn Gln Ile Gly
            420                 425                 430

Asn Asn Leu Ser Pro Gly Asp Thr Tyr Pro Lys Lys Gly Leu Ser Pro
        435                 440                 445

Leu Ala Leu Asn Thr Met Asp Gln Phe Ser Ser Arg Leu Ile Pro Ile
    450                 455                 460

Asn Tyr Asp Gln Leu Lys Lys Leu Asp Ala Gly Lys Gln Ile Lys Leu
465                 470                 475                 480

Glu Thr Thr Gln Val Ser Gly Asn Phe Gly Thr Lys Asn Ser Ser Gly
                485                 490                 495

Gln Ile Val Thr Glu Gly Asn Ser Trp Ser Asp Tyr Ile Ser Gln Ile
            500                 505                 510

Asp Ser Ile Ser Ala Ser Ile Ile Leu Asp Thr Glu Asn Glu Ser Tyr
        515                 520                 525

Glu Arg Arg Val Thr Ala Lys Asn Leu Gln Asp Pro Glu Asp Lys Thr
    530                 535                 540

Pro Glu Leu Thr Ile Gly Glu Ala Ile Glu Lys Ala Phe Gly Ala Thr
545                 550                 555                 560

Lys Lys Asp Gly Leu Leu Tyr Phe Asn Asp Ile Pro Ile Asp Glu Ser
                565                 570                 575

Cys Val Glu Leu Ile Phe Asp Asp Asn Thr Ala Asn Lys Ile Lys Asp
            580                 585                 590

Ser Leu Lys Thr Leu Ser Asp Lys Lys Ile Tyr Asn Val Lys Leu Glu
        595                 600                 605

Arg Gly Met Asn Ile Leu Ile Lys Thr Pro Thr Tyr Phe Thr Asn Phe
    610                 615                 620

Asp Asp Tyr Asn Asn Tyr Pro Ser Thr Trp Ser Asn Val Asn Thr Thr
625                 630                 635                 640

Asn Gln Asp Gly Leu Gln Gly Ser Ala Asn Lys Leu Asn Gly Glu Thr
                645                 650                 655

Lys Ile Lys Ile Pro Met Ser Glu Leu Lys Pro Tyr Lys Arg Tyr Val
            660                 665                 670

Phe Ser Gly Tyr Ser Lys Asp Pro Leu Thr Ser Asn Ser Ile Ile Val
        675                 680                 685

Lys Ile Lys Ala Lys Glu Glu Lys Thr Asp Tyr Leu Val Pro Glu Gln
    690                 695                 700

Gly Tyr Thr Lys Phe Ser Tyr Glu Phe Glu Thr Thr Glu Lys Asp Ser
705                 710                 715                 720

Ser Asn Ile Glu Ile Thr Leu Ile Gly Ser Gly Thr Thr Tyr Leu Asp
                725                 730                 735

Asn Leu Ser Ile Thr Glu Leu Asn Ser Thr Pro Glu Ile Leu Asp Glu
            740                 745                 750

Pro Glu Val Lys Ile Pro Thr Asp Gln Glu Ile Met Asp Ala His Lys
        755                 760                 765

Ile Tyr Phe Ala Asp Leu Asn Phe Asn Pro Ser Thr Gly Asn Thr Tyr
    770                 775                 780

Ile Asn Gly Met Tyr Phe Ala Pro Thr Gln Thr Asn Lys Glu Ala Leu
785                 790                 795                 800

Asp Tyr Ile Gln Lys Tyr Arg Val Glu Ala Thr Leu Gln Tyr Ser Gly
                805                 810                 815
```

-continued

Phe Lys Asp Ile Gly Thr Lys Asp Lys Glu Met Arg Asn Tyr Leu Gly
820 825 830

Asp Pro Asn Gln Pro Lys Thr Asn Tyr Val Asn Leu Arg Ser Tyr Phe
835 840 845

Thr Gly Gly Glu Asn Ile Met Thr Tyr Lys Lys Leu Arg Ile Tyr Ala
850 855 860

Ile Thr Pro Asp Asp Arg Glu Leu Leu Val Leu Ser Val Asp
865 870 875

<210> SEQ ID NO 47
<211> LENGTH: 2054
<212> TYPE: DNA
<213> ORGANISM: Artificial Sequence
<220> FEATURE:
<223> OTHER INFORMATION: Synthetic CBD-BT gene

<400> SEQUENCE: 47
agatctaaaa taaggaggaa aaaaaaatgg ctagcctgat gtctgattgg gaagatgaag 60
acctggatac cgataatgat aacattccgg atagttatga acgcaatggt tacaccatca 120
aagacctgat tgcggttaaa tgggaagata gctttgccga acagggctac aaaaaatacg 180
tgagcaacta cctggaatct aacaccgccg gtgatccgta tacggattac gaaaaagcaa 240
gcggctcttt cgataaagca attaaaaccg aagcgcgtga tccgctggtt gcggcctatc 300
cgatcgtggg cgttggtatg gaaaaactga ttatctctac caacgaacat gcgagtaccg 360
atcagggtaa aaccgtgagt cgcgccacca cgaatagtaa aaccgaaagc aacacggcag 420
gcgtgagcgt taatgtgggc tatcagaacg gttttaccgc gaatgttacc acgaactaca 480
gccacaccac ggataattct accgccgtgc aggattctaa tggcgaaagt tggaacacgg 540
gtctgagtat taacaaaggc gaaagcgcct acatcaacgc aaacgttcgt tactacaaca 600
ccggtacggc cccgatgtac aaagttaccc cgaccacgaa cctggtgctg gatggcgata 660
ccctgagcac gattaaagca caggaaaacc agatcggtaa taacctgtct ccgggcgata 720
cctatccgaa aaaaggtctg agtccgctgg cgctgaatac catggatcag tttagtagcc 780
gcctgattcc gatcaactac gatcagctga aaaaactgga tgccggcaaa cagattaaac 840
tggaaaccac gcaagttagc ggcaatttcg gtaccaaaaa ctctagtggt cagatcgtga 900
cggaaggcaa tagttggagc gattatatta gccagatcga ttctattagt gcaagcatta 960
tcctggatac cgaaaatgaa tcttacgaac gtcgcgtgac ggcgaaaaac ctgcaagatc 1020
cggaagataa aaccccggaa ctgacgatcg gtgaagccat tgaaaaagca tttggtgcga 1080
ccaaaaaaga tggcctgctg tatttcaacg atattccgat cgatgaaagc tgcgttgaac 1140
tgatcttcga tgataacacc gcaaacaaaa tcaaagatag tctgaaaacg ctgagcgata 1200
agaaaattta taacgtgaaa ctggaacgtg gcatgaacat tctgatcaaa accccgacgt 1260
acttcaccaa cttcgatgat tacaacaact acccgagtac gtggagcaat gttaacacca 1320
cgaaccagga tggcctgcag ggtagcgcca acaaactgaa cggtgaaacc aaaatcaaaa 1380
tcccgatgtc tgaactgaaa ccgtataaac gctacgtgtt ttctggctat agtaaagatc 1440
cgctgacctc taatagtatc atcgttaaaa tcaaagcgaa agaagaaaaa accgattacc 1500
tggtgccgga acagggttac acgaaattca gttacgaatt tgaaaccacg gaaaaagata 1560
gctctaacat tgaaatcacc ctgattggca gcggtaccac gtatctggat aatctgtcta 1620
ttaccgaact gaacagtacg ccggaaatcc tggatgaacc ggaagtgaaa atcccgaccg 1680
atcaggaaat catggatgcc cataaaatct atttcgcgga tctgaacttc aacccgagca 1740

```
ccggtaatac gtatattaac ggcatgtact ttgcaccgac ccagacgaat aaagaagcgc   1800

tggattatat tcagaaatac cgtgttgaag ccaccctgca gtatagcggc ttcaaagata   1860

tcggtacgaa agataaagaa atgcgtaatt acctgggcga tccgaaccag ccgaaaacca   1920

attatgtgaa cctgcgctct tactttaccg gcggtgaaaa catcatgacg tacaaaaaac   1980

tgcgtatcta cgcgattacc ccggatgatc gcgaactgct ggttctgagt gtggattaat   2040

aacctaggaa gctt                                                     2054
```

<210> SEQ ID NO 48
<211> LENGTH: 2655
<212> TYPE: DNA
<213> ORGANISM: Artificial Sequence
<220> FEATURE:
<223> OTHER INFORMATION: Synthetic CDTB-GS gene

<400> SEQUENCE: 48

```
tagtaatgaa tggctagcaa aatccagatg cgtaacaaaa aagttctgag ttttctgacc     60

ctgacggcga tcgtgagcca ggccctggtt tatccggtgt acgcgcagac ctctacgagt    120

aaccatagca acaagaaaaa agaaatcgtg aacgaagata tcctgccgaa caatggcctg    180

atgggttatt actttaccga tgaacacttc aaagacctga aactgatggc gccgattaaa    240

gatggcaacc tgaaattcga agagaaaaaa gttgataaac tgctggataa agataaaagc    300

gatgtgaaat ctatccgttg gaccggtcgc attatcccga gcaaagatgg cgaatatacc    360

ctgtctacgg atcgtgatga tgttctgatg caagtgaata ccgaaagcac gatctctaac    420

accctgaaag ttaacatgaa aaagggtaaa gaatacaaag tgcgcatcga actgcaggat    480

aaaaacctgg gctctatcga taatctgagc tctccgaacc tgtattggga actggatggt    540

atgaagaaaa ttatcccgga agaaaatctg tttctgcgtg attacagcaa cattgaaaaa    600

gatgatccgt tcatcccgaa caataacttt ttcgatccga aactgatgtc tgattgggaa    660

gatgaagacc tggataccga taatgataac attccggata gttatgaacg caatggttac    720

accatcaaag acctgattgc ggttaaatgg gaagatagct ttgccgaaca gggctacaaa    780

aaatacgtga gcaactacct ggaatctaac accgccggtg atccgtatac ggattacgaa    840

aaagcaagcg gctctttcga taaagcaatt aaaaccgaag cgcgtgatcc gctggttgcg    900

gcctatccga tcgtgggcgt tggtatggaa aaactgatta tctctaccaa cgaacatgcg    960

agtaccgatc agggtaaaac cgtgagtcgc gccaccacga atagtaaaac cgaaagcaac   1020

acggcaggcg tgagcgttaa tgtgggctat cagaacggtt ttaccgcgaa tgttaccacg   1080

aactacagcc acaccacgga taattctacc gccgtgcagg attctaatgg cgaaagttgg   1140

aacacgggtc tgagtattaa caaaggcgaa agcgcctaca tcaacgcaaa cgttcgttac   1200

tacaacaccg gtacggcccc gatgtacaaa gttaccccga ccacgaacct ggtgctggat   1260

ggcgataccc tgagcacgat taaagcacag gaaaaccaga tcggtaataa cctgtctccg   1320

ggcgatacct atccgaaaaa aggtctgagt ccgctggcgc tgaataccat ggatcagttt   1380

agtagccgcc tgattccgat caactacgat cagctgaaaa aactggatgc cggcaaacag   1440

attaaactgg aaaccacgca agttagcggc aatttcggta ccaaaaactc tagtggtcag   1500

atcgtgacgg aaggcaatag ttggagcgat tatattagcc agatcgattc tattagtgca   1560

agcattatcc tggataccga aaatgaatct tacgaacgtc gcgtgacggc gaaaaacctg   1620

caagatccgg aagataaaac cccggaactg acgatcggtg aagccattga aaaagcattt   1680
```

-continued

```
ggtgcgacca aaaaagatgg cctgctgtat ttcaacgata ttccgatcga tgaaagctgc   1740

gttgaactga tcttcgatga taacaccgca aacaaaatca aagatagtct gaaaacgctg   1800

agcgataaga aaatttataa cgtgaaactg gaacgtggca tgaacattct gatcaaaacc   1860

ccgacgtact tcaccaactt cgatgattac aacaactacc cgagtacgtg gagcaatgtt   1920

aacaccacga accaggatgg cctgcagggt agcgccaaca aactgaacgg tgaaaccaaa   1980

atcaaaatcc cgatgtctga actgaaaccg tataaacgct acgtgttttc tggctatagt   2040

aaagatccgc tgacctctaa tagtatcatc gttaaaatca aagcgaaaga agaaaaaacc   2100

gattacctgg tgccggaaca gggttacacg aaattcagtt acgaatttga aaccacggaa   2160

aaagatagct ctaacattga aatcaccctg attggcagcg gtaccacgta tctggataat   2220

ctgtctatta ccgaactgaa cagtacgccg gaaatcctgg atgaaccgga agtgaaaatc   2280

ccgaccgatc aggaaatcat ggatgcccat aaaatctatt tcgcggatct gaacttcaac   2340

ccgagcaccg gtaatacgta tattaacggc atgtactttg caccgaccca gacgaataaa   2400

gaagcgctgg attatattca gaaataccgt gttgaagcca ccctgcagta tagcggcttc   2460

aaagatatcg gtacgaaaga taaagaaatg cgtaattacc tgggcgatcc gaaccagccg   2520

aaaaccaatt atgtgaacct gcgctcttac tttaccggcg gtgaaaacat catgacgtac   2580

aaaaaactgc gtatctacgc gattaccccg gatgatcgcg aactgctggt tctgagtgtg   2640

gattaataac ctagg                                                    2655
```

<210> SEQ ID NO 49
<211> LENGTH: 972
<212> TYPE: PRT
<213> ORGANISM: Artificial Sequence
<220> FEATURE:
<223> OTHER INFORMATION: ClyA-CBD-BT fusion protein

<400> SEQUENCE: 49

```
Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190
```

-continued

```
Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser Leu Met Ser Asp Trp Glu Asp Glu Asp Leu Asp Thr Asp Asn Asp
305                 310                 315                 320

Asn Ile Pro Asp Ser Tyr Glu Arg Asn Gly Tyr Thr Ile Lys Asp Leu
                325                 330                 335

Ile Ala Val Lys Trp Glu Asp Ser Phe Ala Glu Gln Gly Tyr Lys Lys
            340                 345                 350

Tyr Val Ser Asn Tyr Leu Glu Ser Asn Thr Ala Gly Asp Pro Tyr Thr
        355                 360                 365

Asp Tyr Glu Lys Ala Ser Gly Ser Phe Asp Lys Ala Ile Lys Thr Glu
    370                 375                 380

Ala Arg Asp Pro Leu Val Ala Ala Tyr Pro Ile Val Gly Val Gly Met
385                 390                 395                 400

Glu Lys Leu Ile Ile Ser Thr Asn Glu His Ala Ser Thr Asp Gln Gly
                405                 410                 415

Lys Thr Val Ser Arg Ala Thr Thr Asn Ser Lys Thr Glu Ser Asn Thr
            420                 425                 430

Ala Gly Val Ser Val Asn Val Gly Tyr Gln Asn Gly Phe Thr Ala Asn
        435                 440                 445

Val Thr Thr Asn Tyr Ser His Thr Thr Asp Asn Ser Thr Ala Val Gln
    450                 455                 460

Asp Ser Asn Gly Glu Ser Trp Asn Thr Gly Leu Ser Ile Asn Lys Gly
465                 470                 475                 480

Glu Ser Ala Tyr Ile Asn Ala Asn Val Arg Tyr Tyr Asn Thr Gly Thr
                485                 490                 495

Ala Pro Met Tyr Lys Val Thr Pro Thr Thr Asn Leu Val Leu Asp Gly
            500                 505                 510

Asp Thr Leu Ser Thr Ile Lys Ala Gln Glu Asn Gln Ile Gly Asn Asn
        515                 520                 525

Leu Ser Pro Gly Asp Thr Tyr Pro Lys Lys Gly Leu Ser Pro Leu Ala
    530                 535                 540

Leu Asn Thr Met Asp Gln Phe Ser Ser Arg Leu Ile Pro Ile Asn Tyr
545                 550                 555                 560

Asp Gln Leu Lys Lys Leu Asp Ala Gly Lys Gln Ile Lys Leu Glu Thr
                565                 570                 575

Thr Gln Val Ser Gly Asn Phe Gly Thr Lys Asn Ser Ser Gly Gln Ile
            580                 585                 590

Val Thr Glu Gly Asn Ser Trp Ser Asp Tyr Ile Ser Gln Ile Asp Ser
        595                 600                 605
```

```
Ile Ser Ala Ser Ile Ile Leu Asp Thr Glu Asn Glu Ser Tyr Glu Arg
    610                 615                 620

Arg Val Thr Ala Lys Asn Leu Gln Asp Pro Glu Asp Lys Thr Pro Glu
625                 630                 635                 640

Leu Thr Ile Gly Glu Ala Ile Glu Lys Ala Phe Gly Ala Thr Lys Lys
                645                 650                 655

Asp Gly Leu Leu Tyr Phe Asn Asp Ile Pro Ile Asp Glu Ser Cys Val
            660                 665                 670

Glu Leu Ile Phe Asp Asp Asn Thr Ala Asn Lys Ile Lys Asp Ser Leu
        675                 680                 685

Lys Thr Leu Ser Asp Lys Lys Ile Tyr Asn Val Lys Leu Glu Arg Gly
    690                 695                 700

Met Asn Ile Leu Ile Lys Thr Pro Thr Tyr Phe Thr Asn Phe Asp Asp
705                 710                 715                 720

Tyr Asn Asn Tyr Pro Ser Thr Trp Ser Asn Val Asn Thr Thr Asn Gln
                725                 730                 735

Asp Gly Leu Gln Gly Ser Ala Asn Lys Leu Asn Gly Glu Thr Lys Ile
            740                 745                 750

Lys Ile Pro Met Ser Glu Leu Lys Pro Tyr Lys Arg Tyr Val Phe Ser
        755                 760                 765

Gly Tyr Ser Lys Asp Pro Leu Thr Ser Asn Ser Ile Ile Val Lys Ile
    770                 775                 780

Lys Ala Lys Glu Glu Lys Thr Asp Tyr Leu Val Pro Glu Gln Gly Tyr
785                 790                 795                 800

Thr Lys Phe Ser Tyr Glu Phe Glu Thr Thr Glu Lys Asp Ser Ser Asn
                805                 810                 815

Ile Glu Ile Thr Leu Ile Gly Ser Gly Thr Thr Tyr Leu Asp Asn Leu
            820                 825                 830

Ser Ile Thr Glu Leu Asn Ser Thr Pro Glu Ile Leu Asp Glu Pro Glu
        835                 840                 845

Val Lys Ile Pro Thr Asp Gln Glu Ile Met Asp Ala His Lys Ile Tyr
    850                 855                 860

Phe Ala Asp Leu Asn Phe Asn Pro Ser Thr Gly Asn Thr Tyr Ile Asn
865                 870                 875                 880

Gly Met Tyr Phe Ala Pro Thr Gln Thr Asn Lys Glu Ala Leu Asp Tyr
                885                 890                 895

Ile Gln Lys Tyr Arg Val Glu Ala Thr Leu Gln Tyr Ser Gly Phe Lys
            900                 905                 910

Asp Ile Gly Thr Lys Asp Lys Glu Met Arg Asn Tyr Leu Gly Asp Pro
        915                 920                 925

Asn Gln Pro Lys Thr Asn Tyr Val Asn Leu Arg Ser Tyr Phe Thr Gly
    930                 935                 940

Gly Glu Asn Ile Met Thr Tyr Lys Lys Leu Arg Ile Tyr Ala Ile Thr
945                 950                 955                 960

Pro Asp Asp Arg Glu Leu Leu Val Leu Ser Val Asp
                965                 970
```

<210> SEQ ID NO 50
<211> LENGTH: 3491
<212> TYPE: DNA
<213> ORGANISM: Artificial Sequence
<220> FEATURE:
<223> OTHER INFORMATION: PompC-clyA*-b2 expression cassette

<400> SEQUENCE: 50

```
gaattctgtg gtagcacaga ataatgaaaa gtgtgtaaag aagggtaaaa aaaaccgaat     60
gcgaggcatc cggttgaaat aggggtaaac agacattcag aaatgaatga cggtaataaa    120
taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcatttttg ggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaaatgac tagtattttt gcagaacaaa    540
ctgtagaggt agttaaaagc gcgatcgaaa ccgcagatgg ggcattagac ctttataaca    600
aatacctcga ccaggtcatc ccctggaaga cctttgatga aaccataaaa gagttaagcc    660
gttttaaaca ggagtactcg caggaggctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagatga tggtgtcaag aaactgaatg    900
aagcgcaaaa atctctcctg acaagttcac aaagtttcaa caacgcttcc ggaaaactgc    960
tggcattaga tagccagctg actaatgatt tttcggaaaa aagtagttat ttccagtcac   1020
aggtggatag aatccgtaag gaggcttatg ccggtgctgc agccggcata gtcgccggtc   1080
cgtttggatt aattatttcc tattctattg ctgcgggcgt gattgaaggg aaattgattc   1140
cagaattgaa taacaggcta aaaacagtgc aaaatttctt tactagctta tcagctacag   1200
tgaaacaagc gaataaagat atcgatgcgg caaaattgaa attagccact gaaatagcag   1260
cgattgggga gataaaaacg gaaaccgaaa caaccagatt ctacgttgat tatgatgatt   1320
taatgctttc tttattaaaa ggagctgcaa agaaaatgat taacacctgt aatgaatacc   1380
aacaacgtca tggtaagaag acgcttttcg aggttcctga cgtcgctagc ctgatgtctg   1440
attgggaaga tgaagacctg gataccgata atgataacat tccggatagt tatgaacgca   1500
atggttacac catcaaagac ctgattgcgg ttaaatggga agatagcttt gccgaacagg   1560
gctacaaaaa atacgtgagc aactacctgg aatctaacac cgccggtgat ccgtatacgg   1620
attacgaaaa agcaagcggc tctttcgata aagcaattaa aaccgaagcg cgtgatccgc   1680
tggttgcggc ctatccgatc gtgggcgttg gtatggaaaa actgattatc tctaccaacg   1740
aacatgcgag taccgatcag ggtaaaaccg tgagtcgcgc caccacgaat agtaaaaccg   1800
aaagcaacac ggcaggcgtg agcgttaatg tgggctatca gaacggtttt accgcgaatg   1860
ttaccacgaa ctacagccac accacggata attctaccgc cgtgcaggat tctaatggcg   1920
aaagttggaa cacgggtctg agtattaaca aaggcgaaag cgcctacatc aacgcaaacg   1980
ttcgttacta caacaccggt acggccccga tgtacaaagt taccccgacc acgaacctgg   2040
tgctggatgg cgataccctg agcacgatta aagcacagga aaaccagatc ggtaataacc   2100
tgtctccggg cgatacctat ccgaaaaaag gtctgagtcc gctggcgctg aataccatgg   2160
atcagtttag tagccgcctg attccgatca actacgatca gctgaaaaaa ctggatgccg   2220
gcaaacagat taaactggaa accacgcaag ttagcggcaa tttcggtacc aaaaactcta   2280
gtggtcagat cgtgacggaa ggcaatagtt ggagcgatta tattagccag atcgattcta   2340
ttagtgcaag cattatcctg gataccgaaa atgaatctta cgaacgtcgc gtgacggcga   2400
```

-continued

```
aaaacctgca agatccggaa gataaaaccc cggaactgac gatcggtgaa gccattgaaa   2460

aagcatttgg tgcgaccaaa aaagatggcc tgctgtattt caacgatatt ccgatcgatg   2520

aaagctgcgt tgaactgatc ttcgatgata acaccgcaaa caaaatcaaa gatagtctga   2580

aaacgctgag cgataagaaa atttataacg tgaaactgga acgtggcatg aacattctga   2640

tcaaaacccc gacgtacttc accaacttcg atgattacaa caactacccg agtacgtgga   2700

gcaatgttaa caccacgaac caggatggcc tgcagggtag cgccaacaaa ctgaacggtg   2760

aaaccaaaat caaaatcccg atgtctgaac tgaaaccgta taaacgctac gtgttttctg   2820

gctatagtaa agatccgctg acctctaata gtatcatcgt taaaatcaaa gcgaaagaag   2880

aaaaaaccga ttacctggtg ccggaacagg gttacacgaa attcagttac gaatttgaaa   2940

ccacggaaaa agatagctct aacattgaaa tcaccctgat tggcagcggt accacgtatc   3000

tggataatct gtctattacc gaactgaaca gtacgccgga aatcctggat gaaccggaag   3060

tgaaaatccc gaccgatcag gaaatcatgg atgcccataa aatctatttc gcggatctga   3120

acttcaaccc gagcaccggt aatacgtata ttaacggcat gtactttgca ccgacccaga   3180

cgaataaaga agcgctggat tatattcaga aataccgtgt tgaagccacc ctgcagtata   3240

gcggcttcaa agatatcggt acgaaagata aagaaatgcg taattacctg ggcgatccga   3300

accagccgaa aaccaattat gtgaacctgc gctcttactt taccggcggt gaaaacatca   3360

tgacgtacaa aaaactgcgt atctacgcga ttaccccgga tgatcgcgaa ctgctggttc   3420

tgagtgtgga ttaataacct agctgataac ctagcccgcc taatgagcgg gctttttttt   3480

ctcggcctag g                                                        3491

<210> SEQ ID NO 51
<211> LENGTH: 60
<212> TYPE: DNA
<213> ORGANISM: Artificial Sequence
<220> FEATURE:
<223> OTHER INFORMATION: Forward amplification primer

<400> SEQUENCE: 51

agatctaaaa taaggaggaa aaaaaaatgg ctagcctgat gtctgattgg gaagatgaag     60


<210> SEQ ID NO 52
<211> LENGTH: 43
<212> TYPE: DNA
<213> ORGANISM: Artificial Sequence
<220> FEATURE:
<223> OTHER INFORMATION: Reverse amplification primer


<400> SEQUENCE: 52

aagcttccta ggttattaat ccacactcag aaccagcagt tcg                       43
```